US008883418B2

(12) United States Patent
Pasqual et al.

(10) Patent No.: US 8,883,418 B2
(45) Date of Patent: Nov. 11, 2014

(54) MEASUREMENT OF THE IMMUNOLOGICAL DIVERSITY AND EVALUATION OF THE EFFECTS OF A TREATMENT THROUGH STUDYING V(D)J DIVERSITY

(75) Inventors: Nicolas Pasqual, Grenoble (FR); Sébastien Weisbuch, Villefontaine (FR)

(73) Assignees: ImmunID, Grenoble (FR); Commissariat a l'Energie Atomique et aux Energies Alternatives, Paris (FR)

( * ) Notice: Subject to any disclaimer, the term of this patent is extended or adjusted under 35 U.S.C. 154(b) by 710 days.

(21) Appl. No.: 12/744,853

(22) PCT Filed: Nov. 25, 2008

(86) PCT No.: PCT/FR2008/001640
§ 371 (c)(1),
(2), (4) Date: Jun. 7, 2010

(87) PCT Pub. No.: WO2009/095567
PCT Pub. Date: Aug. 6, 2009

(65) Prior Publication Data
US 2011/0003291 A1   Jan. 6, 2011

(30) Foreign Application Priority Data
Nov. 26, 2007 (EP) ..................................... 07291401

(51) Int. Cl.
*C12Q 1/68* (2006.01)
*C07H 21/04* (2006.01)
*C12P 19/34* (2006.01)

(52) U.S. Cl.
CPC .......... *C12Q 1/6883* (2013.01); *C12Q 2600/16* (2013.01); *C12Q 2600/106* (2013.01); *C12Q 2600/156* (2013.01)
USPC ....................... 435/6.12; 435/91.2; 536/24.33

(58) Field of Classification Search
USPC ............................. 435/6.12, 91.2; 536/24.33
See application file for complete search history.

(56) References Cited

U.S. PATENT DOCUMENTS 5,787,231 A * 7/1998 Johnson et al. ............... 704/260
6,410,277 B1 * 6/2002 Barnes .......................... 435/91.2
2005/0026277 A1 * 2/2005 Festoc ........................ 435/287.2
2005/0048617 A1 * 3/2005 Wu et al. ....................... 435/69.1
2005/0130172 A1 * 6/2005 Beard et al. ....................... 435/6
2006/0234234 A1 * 10/2006 Van Dongen et al. ............ 435/6
2008/0064631 A1 * 3/2008 Molldrem ....................... 514/12
2008/0166704 A1 * 7/2008 Marche et al. .................... 435/6

FOREIGN PATENT DOCUMENTS

WO   WO 2004/033728   4/2004
WO   WO 2005/056828   6/2005

OTHER PUBLICATIONS

Rowen et al., Science, 1996, vol. 5269, p. 1755-1762.*
Koop et al. Genomics, 1994, vol. 19, p. 478-493.*
Lowe et al. Nucleic acid research, 1990, vol. 18 (7), p. 1757-1761.*
The nucleic acid sequence search reports (AC: L36092, M94081, ARK95533, AEA61187, AE000521, AR025294, AEA61102, ADY35402, searched Jan. 4, 2013.*
The nucleic acid sequence search report, AC: L36092, searched Jan. 4, 2013.*
Dongen, et al., "Design and Standardization of PCR Primers and Protocols for Detection of Clonal Immunoglobulin . . . ", Leukemia, 17, pp. 2257-2317, 2003.
Pasqual, et al., "Quantitative and Qualitative Changes in V-J . . . ", J. Exp. Med., 196, pp. 1163-1173, 2002.
Database Geneseq (online), Mar. 25, 2004, "Human Vbeta Gene", ADH69807.
Database EMBL (online), Jun. 15, 1991, "Human T-cell Receprot Germline Gamma-Chain J2 Gene", M12961.
Database EMBL (online), Aug. 14, 1991, "Human J6 to Enhancer DNA of the Immunoglobulin Heavy-Chain Gene Locus", X54712.
Database Geneseq (online), Aug. 25, 2005, "Human TRG Gene Genomic Sequence SEQ ID No. 97", AEA61187.

* cited by examiner

*Primary Examiner* — Kenneth R. Horlock
*Assistant Examiner* — Joyce Tung
(74) *Attorney, Agent, or Firm* — Morgan, Lewis & Bockius LLP

(57) ABSTRACT

The invention relates to a method for analyzing the diversity of the catalogue of T and/or B lymphocytes in an individual, based on the amplification, from a sample, of genomic DNA fragments by PCR multi-n-plexes, with n≥2, carried out with a combination of at least 3 primers defining at least 2 primer couples, each of which includes a primer specifically hybridizing upstream and/or in a given V or D gene and a primer specifically hybridizing downstream and/or in a given J gene, in order to obtain the amplification of at least two fragments characteristic of two distinct V-J or D-J rearrangements from each primer couple. The invention also relates to the applications of this method, in particular in the treatment follow-up or in the diagnosis and/or prognosis of certain diseases.

51 Claims, 22 Drawing Sheets

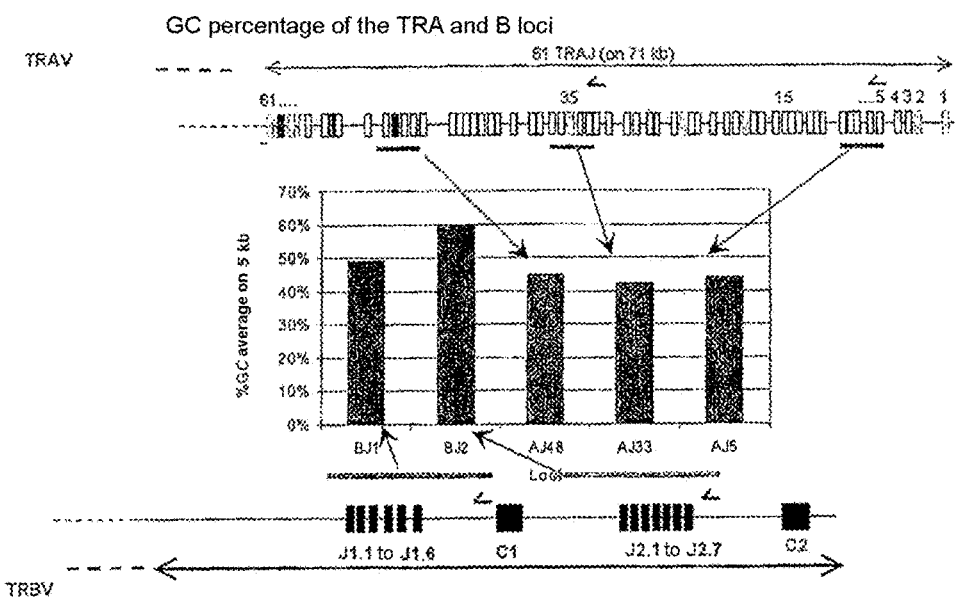
Figure 2a
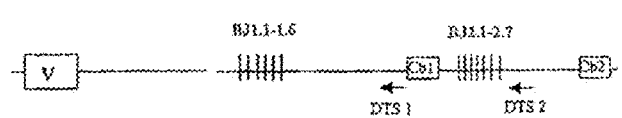 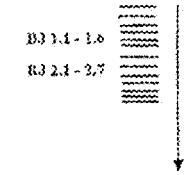
Figure 2b     Figure 2c
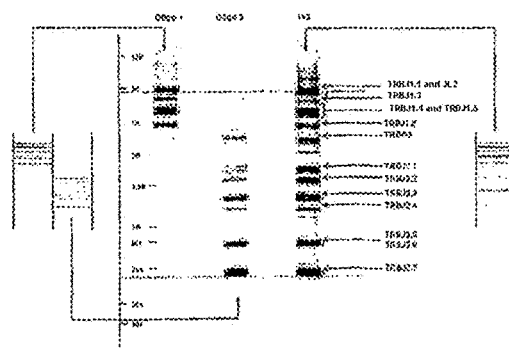
Figure 2d >95% of the TRAJ repertoire Pool of 3 lines:

Responder

Nonresponder

SEQUENCE LISTING

<160> NUMBER OF SEQ ID NOS: 119

<210> SEQ ID NO 1
<211> LENGTH: 25
<212> TYPE: DNA
<213> ORGANISM: Artificial
<220> FEATURE:
<223> OTHER INFORMATION: Synthetic primer

<400> SEQUENCE: 1
cttggtgcat ggctatgtaa tcctg                                        25

<210> SEQ ID NO 2
<211> LENGTH: 22
<212> TYPE: DNA
<213> ORGANISM: Artificial
<220> FEATURE:
<223> OTHER INFORMATION: Synthetic primer

<400> SEQUENCE: 2
ctcgccctct gctcagcttt cc                                           22

<210> SEQ ID NO 3
<211> LENGTH: 26
<212> TYPE: DNA
<213> ORGANISM: Artificial
<220> FEATURE:
<223> OTHER INFORMATION: Synthetic primer

<400> SEQUENCE: 3
cacacagatg ggacaggaag tgatct                                       26

<210> SEQ ID NO 4
<211> LENGTH: 23
<212> TYPE: DNA

<213> ORGANISM: Artificial
<220> FEATURE:
<223> OTHER INFORMATION: Synthetic primer

<400> SEQUENCE: 4
gcttctcacc tgaatgcccc aac                                            23

<210> SEQ ID NO 5
<211> LENGTH: 25
<212> TYPE: DNA
<213> ORGANISM: Artificial
<220> FEATURE:
<223> OTHER INFORMATION: Synthetic primer

<400> SEQUENCE: 5
ctgatcaaaa cgagaggaca gcaag                                          25

<210> SEQ ID NO 6
<211> LENGTH: 25
<212> TYPE: DNA
<213> ORGANISM: Artificial
<220> FEATURE:
<223> OTHER INFORMATION: Synthetic primer

<400> SEQUENCE: 6
ctgatcaaaa cgagaggaca gcacg                                          25

<210> SEQ ID NO 7
<211> LENGTH: 23
<212> TYPE: DNA
<213> ORGANISM: Artificial
<220> FEATURE:
<223> OTHER INFORMATION: Synthetic primer

<400> SEQUENCE: 7
gatcacccag gcaccaacat ctc                                            23

<210> SEQ ID NO 8
<211> LENGTH: 25
<212> TYPE: DNA
<213> ORGANISM: Artificial
<220> FEATURE:
<223> OTHER INFORMATION: Synthetic primer

<400> SEQUENCE: 8
cagatcacac aggagctgga gtctc                                          25

<210> SEQ ID NO 9
<211> LENGTH: 27
<212> TYPE: DNA
<213> ORGANISM: Artificial
<220> FEATURE:
<223> OTHER INFORMATION: Synthetic primer

<400> SEQUENCE: 9
cacagatcac gcagatactg gagtctc                                        27

<210> SEQ ID NO 10
<211> LENGTH: 23
<212> TYPE: DNA
<213> ORGANISM: Artificial
<220> FEATURE:
<223> OTHER INFORMATION: Synthetic primer

<400> SEQUENCE: 10
cgcacaacag ttccctgact tgc                                            23

<210> SEQ ID NO 11
<211> LENGTH: 27
<212> TYPE: DNA
<213> ORGANISM: Artificial
<220> FEATURE:
<223> OTHER INFORMATION: Synthetic primer

<400> SEQUENCE: 11
ttcacagttg cctaaggatc gattttc                                27

<210> SEQ ID NO 12
<211> LENGTH: 27
<212> TYPE: DNA
<213> ORGANISM: Artificial
<220> FEATURE:
<223> OTHER INFORMATION: Synthetic primer

<400> SEQUENCE: 12
ttctctggta cagacagacc tttgtgc                                27

<210> SEQ ID NO 13
<211> LENGTH: 27
<212> TYPE: DNA
<213> ORGANISM: Artificial
<220> FEATURE:
<223> OTHER INFORMATION: Synthetic primer

<400> SEQUENCE: 13
ttttctggta cagagatacc ttcgtgc                                27

<210> SEQ ID NO 14
<211> LENGTH: 25
<212> TYPE: DNA
<213> ORGANISM: Artificial
<220> FEATURE:
<223> OTHER INFORMATION: Synthetic primer

<400> SEQUENCE: 14
gttgctgaag tgtcaaactc tcccg                                  25

<210> SEQ ID NO 15
<211> LENGTH: 24
<212> TYPE: DNA
<213> ORGANISM: Artificial
<220> FEATURE:
<223> OTHER INFORMATION: Synthetic primer

<400> SEQUENCE: 15
tccccagcca cagcgtaata gaga                                   24

<210> SEQ ID NO 16
<211> LENGTH: 24
<212> TYPE: DNA
<213> ORGANISM: Artificial
<220> FEATURE:
<223> OTHER INFORMATION: Synthetic primer

<400> SEQUENCE: 16
ccccaaagct gctgttccac tact                                   24

<210> SEQ ID NO 17
<211> LENGTH: 22
<212> TYPE: DNA
<213> ORGANISM: Artificial
<220> FEATURE:

```
<223> OTHER INFORMATION: Synthetic primer

<400> SEQUENCE: 17
ctcctggtga agaagtcgcc ca                                              22

<210> SEQ ID NO 18
<211> LENGTH: 22
<212> TYPE: DNA
<213> ORGANISM: Artificial
<220> FEATURE:
<223> OTHER INFORMATION: Synthetic primer

<400> SEQUENCE: 18
tagtgcgagg agattcggca gc                                              22

<210> SEQ ID NO 19
<211> LENGTH: 23
<212> TYPE: DNA
<213> ORGANISM: Artificial
<220> FEATURE:
<223> OTHER INFORMATION: Synthetic primer

<400> SEQUENCE: 19
ctgggagcaa gtgagtcctg ggt                                             23

<210> SEQ ID NO 20
<211> LENGTH: 24
<212> TYPE: DNA
<213> ORGANISM: Artificial
<220> FEATURE:
<223> OTHER INFORMATION: Synthetic primer

<400> SEQUENCE: 20
tcatcaacca tgcaagcctg acct                                            24

<210> SEQ ID NO 21
<211> LENGTH: 24
<212> TYPE: DNA
<213> ORGANISM: Artificial
<220> FEATURE:
<223> OTHER INFORMATION: Synthetic primer

<400> SEQUENCE: 21
agtgtctctc gacaggcaca ggct                                            24

<210> SEQ ID NO 22
<211> LENGTH: 23
<212> TYPE: DNA
<213> ORGANISM: Artificial
<220> FEATURE:
<223> OTHER INFORMATION: Synthetic primer

<400> SEQUENCE: 22
cctctttgtt gggtttgtgc ctg                                             23

<210> SEQ ID NO 23
<211> LENGTH: 22
<212> TYPE: DNA
<213> ORGANISM: Artificial
<220> FEATURE:
<223> OTHER INFORMATION: Synthetic primer

<400> SEQUENCE: 23
gtccccttcc tttacaggcc cc                                              22
```

<210> SEQ ID NO 24
<211> LENGTH: 21
<212> TYPE: DNA
<213> ORGANISM: Artificial
<220> FEATURE:
<223> OTHER INFORMATION: Synthetic primer

<400> SEQUENCE: 24
ccatcagccg cccaaaccta a                                      21

<210> SEQ ID NO 25
<211> LENGTH: 26
<212> TYPE: DNA
<213> ORGANISM: Artificial
<220> FEATURE:
<223> OTHER INFORMATION: Synthetic primer

<400> SEQUENCE: 25
tgctcttcta ctccgttggt attggc                                 26

<210> SEQ ID NO 26
<211> LENGTH: 25
<212> TYPE: DNA
<213> ORGANISM: Artificial
<220> FEATURE:
<223> OTHER INFORMATION: Synthetic primer

<400> SEQUENCE: 26
ttctctataa ggacatgccc caacg                                  25

<210> SEQ ID NO 27
<211> LENGTH: 23
<212> TYPE: DNA
<213> ORGANISM: Artificial
<220> FEATURE:
<223> OTHER INFORMATION: Synthetic primer

<400> SEQUENCE: 27
ttggagaggg gtgggtactg gag                                    23

<210> SEQ ID NO 28
<211> LENGTH: 26
<212> TYPE: DNA
<213> ORGANISM: Artificial
<220> FEATURE:
<223> OTHER INFORMATION: Synthetic primer

<400> SEQUENCE: 28
ctcccaccca cttcactata aatgcc                                 26

<210> SEQ ID NO 29
<211> LENGTH: 21
<212> TYPE: DNA
<213> ORGANISM: Artificial
<220> FEATURE:
<223> OTHER INFORMATION: Synthetic primer

<400> SEQUENCE: 29
gagcaggtgg gcacagtgag c                                      21

<210> SEQ ID NO 30
<211> LENGTH: 24
<212> TYPE: DNA
<213> ORGANISM: Artificial
<220> FEATURE:
<223> OTHER INFORMATION: Synthetic primer

```
<400> SEQUENCE: 30
tcccccaagt attgcatttg gatt                                          24

<210> SEQ ID NO 31
<211> LENGTH: 25
<212> TYPE: DNA
<213> ORGANISM: Artificial
<220> FEATURE:
<223> OTHER INFORMATION: Synthetic primer

<400> SEQUENCE: 31
aactcaacag ggtccttgcc actta                                         25

<210> SEQ ID NO 32
<211> LENGTH: 28
<212> TYPE: DNA
<213> ORGANISM: Artificial
<220> FEATURE:
<223> OTHER INFORMATION: Synthetic primer

<400> SEQUENCE: 32
ccacccacat ttgatgtttt tatttctt                                      28

<210> SEQ ID NO 33
<211> LENGTH: 24
<212> TYPE: DNA
<213> ORGANISM: Artificial
<220> FEATURE:
<223> OTHER INFORMATION: Synthetic primer

<400> SEQUENCE: 33
tagtgtctcc tctcccgtgc agtc                                          24

<210> SEQ ID NO 34
<211> LENGTH: 28
<212> TYPE: DNA
<213> ORGANISM: Artificial
<220> FEATURE:
<223> OTHER INFORMATION: Synthetic primer

<400> SEQUENCE: 34
gttccagtcc caaaggttaa tttctcat                                      28

<210> SEQ ID NO 35
<211> LENGTH: 24
<212> TYPE: DNA
<213> ORGANISM: Artificial
<220> FEATURE:
<223> OTHER INFORMATION: Synthetic primer

<400> SEQUENCE: 35
agaacaagct ggaggcaact aggc                                          24

<210> SEQ ID NO 36
<211> LENGTH: 28
<212> TYPE: DNA
<213> ORGANISM: Artificial
<220> FEATURE:
<223> OTHER INFORMATION: Synthetic primer

<400> SEQUENCE: 36
aacaccagtc tgatctctca tttttgct                                      28

<210> SEQ ID NO 37
<211> LENGTH: 29
```

```
<212> TYPE: DNA
<213> ORGANISM: Artificial
<220> FEATURE:
<223> OTHER INFORMATION: Synthetic primer

<400> SEQUENCE: 37
caagactaaa ggagttaatt catctcccc                                    29

<210> SEQ ID NO 38
<211> LENGTH: 24
<212> TYPE: DNA
<213> ORGANISM: Artificial
<220> FEATURE:
<223> OTHER INFORMATION: Synthetic primer

<400> SEQUENCE: 38
aatccctctg atgggcacca tatc                                         24

<210> SEQ ID NO 39
<211> LENGTH: 20
<212> TYPE: DNA
<213> ORGANISM: Artificial
<220> FEATURE:
<223> OTHER INFORMATION: Synthetic primer

<400> SEQUENCE: 39
acatgggtgg gatggggtca                                              20

<210> SEQ ID NO 40
<211> LENGTH: 20
<212> TYPE: DNA
<213> ORGANISM: Artificial
<220> FEATURE:
<223> OTHER INFORMATION: Synthetic primer

<400> SEQUENCE: 40
tgggagtaaa gggctggggc                                              20

<210> SEQ ID NO 41
<211> LENGTH: 25
<212> TYPE: DNA
<213> ORGANISM: Artificial
<220> FEATURE:
<223> OTHER INFORMATION: Synthetic primer

<400> SEQUENCE: 41
aacctcaatt ccaggcagca gtatc                                        25

<210> SEQ ID NO 42
<211> LENGTH: 26
<212> TYPE: DNA
<213> ORGANISM: Artificial
<220> FEATURE:
<223> OTHER INFORMATION: Synthetic primer

<400> SEQUENCE: 42
ggtcgttttt cttcattcct tagtcg                                       26

<210> SEQ ID NO 43
<211> LENGTH: 22
<212> TYPE: DNA
<213> ORGANISM: Artificial
<220> FEATURE:
<223> OTHER INFORMATION: Synthetic primer

<400> SEQUENCE: 43
```

```
tccccttccc attttccact cg                                                   22

<210> SEQ ID NO 44
<211> LENGTH: 23
<212> TYPE: DNA
<213> ORGANISM: Artificial
<220> FEATURE:
<223> OTHER INFORMATION: Synthetic primer

<400> SEQUENCE: 44
ccctgtttat ccctgccgac aga                                                  23

<210> SEQ ID NO 45
<211> LENGTH: 24
<212> TYPE: DNA
<213> ORGANISM: Artificial
<220> FEATURE:
<223> OTHER INFORMATION: Synthetic primer

<400> SEQUENCE: 45
ctggatgcag acacaaagca aagc                                                 24

<210> SEQ ID NO 46
<211> LENGTH: 27
<212> TYPE: DNA
<213> ORGANISM: Artificial
<220> FEATURE:
<223> OTHER INFORMATION: Synthetic primer

<400> SEQUENCE: 46
aatgaagatg gaaggtttac agcacag                                              27

<210> SEQ ID NO 47
<211> LENGTH: 28
<212> TYPE: DNA
<213> ORGANISM: Artificial
<220> FEATURE:
<223> OTHER INFORMATION: Synthetic primer

<400> SEQUENCE: 47
acaaagaaga tggaaggttt acagcaca                                             28

<210> SEQ ID NO 48
<211> LENGTH: 22
<212> TYPE: DNA
<213> ORGANISM: Artificial
<220> FEATURE:
<223> OTHER INFORMATION: Synthetic primer

<400> SEQUENCE: 48
cgccaacctt gtcatctccg ct                                                   22

<210> SEQ ID NO 49
<211> LENGTH: 27
<212> TYPE: DNA
<213> ORGANISM: Artificial
<220> FEATURE:
<223> OTHER INFORMATION: Synthetic primer

<400> SEQUENCE: 49
ctagagagag catcaaaggc ttcactg                                              27

<210> SEQ ID NO 50
<211> LENGTH: 22
<212> TYPE: DNA
<213> ORGANISM: Artificial
```

```
<220> FEATURE:
<223> OTHER INFORMATION: Synthetic primer

<400> SEQUENCE: 50
cgggcagcag acactgcttc tt                                              22

<210> SEQ ID NO 51
<211> LENGTH: 24
<212> TYPE: DNA
<213> ORGANISM: Artificial
<220> FEATURE:
<223> OTHER INFORMATION: Synthetic primer

<400> SEQUENCE: 51
tcgtcggaac tcttttgatg agca                                            24

<210> SEQ ID NO 52
<211> LENGTH: 24
<212> TYPE: DNA
<213> ORGANISM: Artificial
<220> FEATURE:
<223> OTHER INFORMATION: Synthetic primer

<400> SEQUENCE: 52
tgcctcgctg gataaatcat cagg                                            24

<210> SEQ ID NO 53
<211> LENGTH: 21
<212> TYPE: DNA
<213> ORGANISM: Artificial
<220> FEATURE:
<223> OTHER INFORMATION: Synthetic primer

<400> SEQUENCE: 53
cccagaccac agactcaggc g                                               21

<210> SEQ ID NO 54
<211> LENGTH: 28
<212> TYPE: DNA
<213> ORGANISM: Artificial
<220> FEATURE:
<223> OTHER INFORMATION: Synthetic primer

<400> SEQUENCE: 54
cgtccagatg tgagtgaaaa gaaagaag                                        28

<210> SEQ ID NO 55
<211> LENGTH: 27
<212> TYPE: DNA
<213> ORGANISM: Artificial
<220> FEATURE:
<223> OTHER INFORMATION: Synthetic primer

<400> SEQUENCE: 55
tggacatccc gtttttttga tacagtt                                         27

<210> SEQ ID NO 56
<211> LENGTH: 27
<212> TYPE: DNA
<213> ORGANISM: Artificial
<220> FEATURE:
<223> OTHER INFORMATION: Synthetic primer

<400> SEQUENCE: 56
tggtgacagt agttacgggt ggagaag                                         27
```

```
<210> SEQ ID NO 57
<211> LENGTH: 24
<212> TYPE: DNA
<213> ORGANISM: Artificial
<220> FEATURE:
<223> OTHER INFORMATION: Synthetic primer

<400> SEQUENCE: 57
agcaaaattc accatccctg agcg                                           24

<210> SEQ ID NO 58
<211> LENGTH: 24
<212> TYPE: DNA
<213> ORGANISM: Artificial
<220> FEATURE:
<223> OTHER INFORMATION: Synthetic primer

<400> SEQUENCE: 58
tgaagggtgg agaacagaag ggtc                                           24

<210> SEQ ID NO 59
<211> LENGTH: 27
<212> TYPE: DNA
<213> ORGANISM: Artificial
<220> FEATURE:
<223> OTHER INFORMATION: Synthetic primer

<400> SEQUENCE: 59
ggctgggaag tttggtgata tagtgtc                                        27

<210> SEQ ID NO 60
<211> LENGTH: 27
<212> TYPE: DNA
<213> ORGANISM: Artificial
<220> FEATURE:
<223> OTHER INFORMATION: Synthetic primer

<400> SEQUENCE: 60
acatttttct acacaggggt gagcagt                                        27

<210> SEQ ID NO 61
<211> LENGTH: 28
<212> TYPE: DNA
<213> ORGANISM: Artificial
<220> FEATURE:
<223> OTHER INFORMATION: Synthetic primer

<400> SEQUENCE: 61
gccctcctga aaatgtgtaa agaaatgt                                       28

<210> SEQ ID NO 62
<211> LENGTH: 26
<212> TYPE: DNA
<213> ORGANISM: Artificial
<220> FEATURE:
<223> OTHER INFORMATION: Synthetic primer

<400> SEQUENCE: 62
acatatgagc cctttatgga agtccg                                         26

<210> SEQ ID NO 63
<211> LENGTH: 30
<212> TYPE: DNA
<213> ORGANISM: Artificial
<220> FEATURE:
<223> OTHER INFORMATION: Synthetic primer
```

<400> SEQUENCE: 63
tattatactt acgcaagcac aaggaacaac                                    30

<210> SEQ ID NO 64
<211> LENGTH: 28
<212> TYPE: DNA
<213> ORGANISM: Artificial
<220> FEATURE:
<223> OTHER INFORMATION: Synthetic primer

<400> SEQUENCE: 64
tgtactatga ctcctacacc tccagcgt                                      28

<210> SEQ ID NO 65
<211> LENGTH: 23
<212> TYPE: DNA
<213> ORGANISM: Artificial
<220> FEATURE:
<223> OTHER INFORMATION: Synthetic primer

<400> SEQUENCE: 65 aaggggggaac gaagtcagtc acg                                          23

<210> SEQ ID NO 66
<211> LENGTH: 26
<212> TYPE: DNA
<213> ORGANISM: Artificial
<220> FEATURE:
<223> OTHER INFORMATION: Synthetic primer

<400> SEQUENCE: 66
gtgttggaat caggaatcag tcgaga                                        26

<210> SEQ ID NO 67
<211> LENGTH: 23
<212> TYPE: DNA
<213> ORGANISM: Artificial
<220> FEATURE:
<223> OTHER INFORMATION: Synthetic primer

<400> SEQUENCE: 67
tgcctcctta gatggaggat gcc                                           23

<210> SEQ ID NO 68
<211> LENGTH: 26
<212> TYPE: DNA
<213> ORGANISM: Artificial
<220> FEATURE:
<223> OTHER INFORMATION: Synthetic primer

<400> SEQUENCE: 68
gcaaggaggc acgcatacta gttagc                                        26

<210> SEQ ID NO 69
<211> LENGTH: 28
<212> TYPE: DNA
<213> ORGANISM: Artificial
<220> FEATURE:
<223> OTHER INFORMATION: Synthetic primer

<400> SEQUENCE: 69
acaaagaaga tggaaggttt acagcaca                                      28

<210> SEQ ID NO 70

```
<211> LENGTH: 22
<212> TYPE: DNA
<213> ORGANISM: Artificial
<220> FEATURE:
<223> OTHER INFORMATION: Synthetic primer

<400> SEQUENCE: 70
cgccaacctt gtcatctccg ct                                              22

<210> SEQ ID NO 71
<211> LENGTH: 27
<212> TYPE: DNA
<213> ORGANISM: Artificial
<220> FEATURE:
<223> OTHER INFORMATION: Synthetic primer

<400> SEQUENCE: 71
ctagagagag catcaaaggc ttcactg                                         27

<210> SEQ ID NO 72
<211> LENGTH: 22
<212> TYPE: DNA
<213> ORGANISM: Artificial
<220> FEATURE:
<223> OTHER INFORMATION: Synthetic primer

<400> SEQUENCE: 72
cgggcagcag acactgcttc tt                                              22

<210> SEQ ID NO 73
<211> LENGTH: 24
<212> TYPE: DNA
<213> ORGANISM: Artificial
<220> FEATURE:
<223> OTHER INFORMATION: Synthetic primer

<400> SEQUENCE: 73
tgcctcgctg gataaatcat cagg                                            24

<210> SEQ ID NO 74
<211> LENGTH: 21
<212> TYPE: DNA
<213> ORGANISM: Artificial
<220> FEATURE:
<223> OTHER INFORMATION: Synthetic primer

<400> SEQUENCE: 74
caggagggag ccaattccac g                                               21

<210> SEQ ID NO 75
<211> LENGTH: 28
<212> TYPE: DNA
<213> ORGANISM: Artificial
<220> FEATURE:
<223> OTHER INFORMATION: Synthetic primer

<400> SEQUENCE: 75
cgtccagatg tgagtgaaaa gaaagaag                                        28

<210> SEQ ID NO 76
<211> LENGTH: 27
<212> TYPE: DNA
<213> ORGANISM: Artificial
<220> FEATURE:
<223> OTHER INFORMATION: Synthetic primer

<400> SEQUENCE: 76
```

```
tggacatccc gttttttga tacagtt                                               27

<210> SEQ ID NO 77
<211> LENGTH: 24
<212> TYPE: DNA
<213> ORGANISM: Artificial
<220> FEATURE:
<223> OTHER INFORMATION: Synthetic primer

<400> SEQUENCE: 77
agcaaaattc accatccctg agcg                                                 24

<210> SEQ ID NO 78
<211> LENGTH: 24
<212> TYPE: DNA
<213> ORGANISM: Artificial
<220> FEATURE:
<223> OTHER INFORMATION: Synthetic primer

<400> SEQUENCE: 78
tgaagggtgg agaacagaag ggtc                                                 24

<210> SEQ ID NO 79
<211> LENGTH: 27
<212> TYPE: DNA
<213> ORGANISM: Artificial
<220> FEATURE:
<223> OTHER INFORMATION: Synthetic primer

<400> SEQUENCE: 79
ggctgggaag tttggtgata tagtgtc                                              27

<210> SEQ ID NO 80
<211> LENGTH: 26
<212> TYPE: DNA
<213> ORGANISM: Artificial
<220> FEATURE:
<223> OTHER INFORMATION: Synthetic primer

<400> SEQUENCE: 80
agtgaagaca aggtggtaca aagccc                                               26

<210> SEQ ID NO 81
<211> LENGTH: 26
<212> TYPE: DNA
<213> ORGANISM: Artificial
<220> FEATURE:
<223> OTHER INFORMATION: Synthetic primer

<400> SEQUENCE: 81
gggaggaaca ggattattgg ggtaac                                               26

<210> SEQ ID NO 82
<211> LENGTH: 28
<212> TYPE: DNA
<213> ORGANISM: Artificial
<220> FEATURE:
<223> OTHER INFORMATION: Synthetic primer

<400> SEQUENCE: 82
gccctcctga aaatgtgtaa agaaatgt                                             28

<210> SEQ ID NO 83
<211> LENGTH: 25
<212> TYPE: DNA
```

```
<213> ORGANISM: Artificial
<220> FEATURE:
<223> OTHER INFORMATION: Synthetic primer

<400> SEQUENCE: 83
cagtatccat gccagtgagg aaagc                                              25

<210> SEQ ID NO 84
<211> LENGTH: 24
<212> TYPE: DNA
<213> ORGANISM: Artificial
<220> FEATURE:
<223> OTHER INFORMATION: Synthetic primer

<400> SEQUENCE: 84
gacaaagtaa cccagagttc cccg                                               24

<210> SEQ ID NO 85
<211> LENGTH: 25
<212> TYPE: DNA
<213> ORGANISM: Artificial
<220> FEATURE:
<223> OTHER INFORMATION: Synthetic primer

<400> SEQUENCE: 85
gatcttgcag tcctacagac accgc                                              25

<210> SEQ ID NO 86
<211> LENGTH: 22
<212> TYPE: DNA
<213> ORGANISM: Artificial
<220> FEATURE:
<223> OTHER INFORMATION: Synthetic primer

<400> SEQUENCE: 86
gacaagggct tgagtggatg gg                                                 22

<210> SEQ ID NO 87
<211> LENGTH: 22
<212> TYPE: DNA
<213> ORGANISM: Artificial
<220> FEATURE:
<223> OTHER INFORMATION: Synthetic primer

<400> SEQUENCE: 87
catggaccct gtggacacag cc                                                 22

<210> SEQ ID NO 88
<211> LENGTH: 24
<212> TYPE: DNA
<213> ORGANISM: Artificial
<220> FEATURE:
<223> OTHER INFORMATION: Synthetic primer

<400> SEQUENCE: 88
tgtttgcagg tgtccagtgt gagg                                               24

<210> SEQ ID NO 89
<211> LENGTH: 25
<212> TYPE: DNA
<213> ORGANISM: Artificial
<220> FEATURE:
<223> OTHER INFORMATION: Synthetic primer

<400> SEQUENCE: 89
gaaccagttc tccctgaagc tgagc                                              25
```

<210> SEQ ID NO 90
<211> LENGTH: 21
<212> TYPE: DNA
<213> ORGANISM: Artificial
<220> FEATURE:
<223> OTHER INFORMATION: Synthetic primer

<400> SEQUENCE: 90
tgcagtggag cagcctgaag g                                        21

<210> SEQ ID NO 91
<211> LENGTH: 23
<212> TYPE: DNA
<213> ORGANISM: Artificial
<220> FEATURE:
<223> OTHER INFORMATION: Synthetic primer

<400> SEQUENCE: 91
agcagcattc acagactgag ggg                                      23

<210> SEQ ID NO 92
<211> LENGTH: 23
<212> TYPE: DNA
<213> ORGANISM: Artificial
<220> FEATURE:
<223> OTHER INFORMATION: Synthetic primer

<400> SEQUENCE: 92
gattctgaac agccccgagt cac                                      23

<210> SEQ ID NO 93
<211> LENGTH: 22
<212> TYPE: DNA
<213> ORGANISM: Artificial
<220> FEATURE:
<223> OTHER INFORMATION: Synthetic primer

<400> SEQUENCE: 93
ggacaggagg attttgtggg gg                                       22

<210> SEQ ID NO 94
<211> LENGTH: 20
<212> TYPE: DNA
<213> ORGANISM: Artificial
<220> FEATURE:
<223> OTHER INFORMATION: Synthetic primer

<400> SEQUENCE: 94
aggtcagccc tggacatccc                                          20

<210> SEQ ID NO 95
<211> LENGTH: 19
<212> TYPE: DNA
<213> ORGANISM: Artificial
<220> FEATURE:
<223> OTHER INFORMATION: Synthetic primer

<400> SEQUENCE: 95
atccccagga cgcagcacc                                           19

<210> SEQ ID NO 96
<211> LENGTH: 20
<212> TYPE: DNA
<213> ORGANISM: Artificial
<220> FEATURE:

<223> OTHER INFORMATION: Synthetic primer

<400> SEQUENCE: 96
agctcctcct gacagccccg                                               20

<210> SEQ ID NO 97
<211> LENGTH: 21
<212> TYPE: DNA
<213> ORGANISM: Artificial
<220> FEATURE:
<223> OTHER INFORMATION: Synthetic primer

<400> SEQUENCE: 97
acaccagaca gaggggcagg c                                             21

<210> SEQ ID NO 98
<211> LENGTH: 20
<212> TYPE: DNA
<213> ORGANISM: Artificial
<220> FEATURE:
<223> OTHER INFORMATION: Synthetic primer

<400> SEQUENCE: 98
agaccgcagc cacatcagcc                                               20

<210> SEQ ID NO 99
<211> LENGTH: 23
<212> TYPE: DNA
<213> ORGANISM: Artificial
<220> FEATURE:
<223> OTHER INFORMATION: Synthetic primer

<400> SEQUENCE: 99
gtggctgttc actctgcgga gtc                                           23

<210> SEQ ID NO 100
<211> LENGTH: 28
<212> TYPE: DNA
<213> ORGANISM: Artificial
<220> FEATURE:
<223> OTHER INFORMATION: Synthetic primer

<400> SEQUENCE: 100
tcaaaaactt atggacaatc agactgcc                                      28

<210> SEQ ID NO 101
<211> LENGTH: 26
<212> TYPE: DNA
<213> ORGANISM: Artificial
<220> FEATURE:
<223> OTHER INFORMATION: Synthetic primer

<400> SEQUENCE: 101
caggacccaa agtcttacag atccca                                        26

<210> SEQ ID NO 102
<211> LENGTH: 25
<212> TYPE: DNA
<213> ORGANISM: Artificial
<220> FEATURE:
<223> OTHER INFORMATION: Synthetic primer

<400> SEQUENCE: 102
ttgtaaacga aacagttcca aggcg                                         25

```
<210> SEQ ID NO 103
<211> LENGTH: 24
<212> TYPE: DNA
<213> ORGANISM: Artificial
<220> FEATURE:
<223> OTHER INFORMATION: Synthetic primer

<400> SEQUENCE: 103
ttggaatgtg agcaacatct ggga                                          24

<210> SEQ ID NO 104
<211> LENGTH: 25
<212> TYPE: DNA
<213> ORGANISM: Artificial
<220> FEATURE:
<223> OTHER INFORMATION: Synthetic primer

<400> SEQUENCE: 104
cccagcagat tctcagtcca acagt                                         25

<210> SEQ ID NO 105
<211> LENGTH: 22
<212> TYPE: DNA
<213> ORGANISM: Artificial
<220> FEATURE:
<223> OTHER INFORMATION: Synthetic primer

<400> SEQUENCE: 105
tggaggctgc agtcacccaa ag                                            22

<210> SEQ ID NO 106
<211> LENGTH: 28
<212> TYPE: DNA
<213> ORGANISM: Artificial
<220> FEATURE:
<223> OTHER INFORMATION: Synthetic primer

<400> SEQUENCE: 106
gttatagata attcacagtt gccctcgg                                      28

<210> SEQ ID NO 107
<211> LENGTH: 24
<212> TYPE: DNA
<213> ORGANISM: Artificial
<220> FEATURE:
<223> OTHER INFORMATION: Synthetic primer

<400> SEQUENCE: 107
ttccgtgttc ataactccac agcg                                          24

<210> SEQ ID NO 108
<211> LENGTH: 23
<212> TYPE: DNA
<213> ORGANISM: Artificial
<220> FEATURE:
<223> OTHER INFORMATION: Synthetic primer

<400> SEQUENCE: 108
ctgaagatcc agagcacgca acc                                           23

<210> SEQ ID NO 109
<211> LENGTH: 25
<212> TYPE: DNA
<213> ORGANISM: Artificial
<220> FEATURE:
<223> OTHER INFORMATION: Synthetic primer
```

```
<400> SEQUENCE: 109
ttttgagaag ttccaatcca gtcgg                                              25

<210> SEQ ID NO 110
<211> LENGTH: 27
<212> TYPE: DNA
<213> ORGANISM: Artificial
<220> FEATURE:
<223> OTHER INFORMATION: Synthetic primer

<400> SEQUENCE: 110
cgatctatct gaaggctatg atgcgtc                                            27

<210> SEQ ID NO 111
<211> LENGTH: 25
<212> TYPE: DNA
<213> ORGANISM: Artificial
<220> FEATURE:
<223> OTHER INFORMATION: Synthetic primer

<400> SEQUENCE: 111
ctgtagcttg gtatcgtcaa tcgcc                                              25

<210> SEQ ID NO 112
<211> LENGTH: 27
<212> TYPE: DNA
<213> ORGANISM: Artificial
<220> FEATURE:
<223> OTHER INFORMATION: Synthetic primer

<400> SEQUENCE: 112
aacacaccca ataattttc cttgctg                                             27

<210> SEQ ID NO 113
<211> LENGTH: 27
<212> TYPE: DNA
<213> ORGANISM: Artificial
<220> FEATURE:
<223> OTHER INFORMATION: Synthetic primer

<400> SEQUENCE: 113
tggaaatcct atcctctgaa gaagacg                                            27

<210> SEQ ID NO 114
<211> LENGTH: 24
<212> TYPE: DNA
<213> ORGANISM: Artificial
<220> FEATURE:
<223> OTHER INFORMATION: Synthetic primer

<400> SEQUENCE: 114
tctttgacct ggagattgcc aacc                                               24

<210> SEQ ID NO 115
<211> LENGTH: 24
<212> TYPE: DNA
<213> ORGANISM: Artificial
<220> FEATURE:
<223> OTHER INFORMATION: Synthetic primer

<400> SEQUENCE: 115
atacagggtc tcacggaaga agcg                                               24

<210> SEQ ID NO 116
<211> LENGTH: 23
```

```
<212> TYPE: DNA
<213> ORGANISM: Artificial
<220> FEATURE:
<223> OTHER INFORMATION: Synthetic primer

<400> SEQUENCE: 116
atggcaactg caaatgaagg ctc                                    23

<210> SEQ ID NO 117
<211> LENGTH: 24
<212> TYPE: DNA
<213> ORGANISM: Artificial
<220> FEATURE:
<223> OTHER INFORMATION: Synthetic primer

<400> SEQUENCE: 117
acgaccaatt catcctaagc acgg                                   24

<210> SEQ ID NO 118
<211> LENGTH: 26
<212> TYPE: DNA
<213> ORGANISM: Artificial
<220> FEATURE:
<223> OTHER INFORMATION: Synthetic primer

<400> SEQUENCE: 118
gcatggctat ttgaaacagt ggctct                                 26

<210> SEQ ID NO 119
<211> LENGTH: 22
<212> TYPE: DNA
<213> ORGANISM: Artificial
<220> FEATURE:
<223> OTHER INFORMATION: Synthetic primer

<400> SEQUENCE: 119
ccttgtcctg gcttgcgaga ga                                     22
```

MEASUREMENT OF THE IMMUNOLOGICAL DIVERSITY AND EVALUATION OF THE EFFECTS OF A TREATMENT THROUGH STUDYING V(D)J DIVERSITY

RELATED APPLICATIONS

The present application is a U.S. National Phase Application of International Application No. PCT/FR2008/001640 (filed Nov. 25, 2008) which claims priority to European Patent Application No. 07291401.3 (filed Nov. 26, 2007) which are hereby incorporated by reference in their entirety.

SEQUENCE LISTING SUBMISSION VIA EFS-WEB

A computer readable text file, entitled "45636-5138-SeqListing.txt," created on or about May 26, 2010 with a file size of about 22 kb contains the sequence listing for this application and is hereby incorporated by reference in its entirety.

The present invention relates to the immunology field. More specifically, the present invention relates to a method for the in vitro analysis of the diversity of the T and/or B lymphocyte repertoire of an individual and to uses thereof, in particular in the follow-up of a treatment or in the diagnosis and/or prognosis of certain pathological conditions.

In order to be functional, a lymphocyte must have an antigen-specific recognition system. This parameter is essential: it defines the very function of the T or B cell. During the early stages of T-lymphocyte differentiation, the loci encoding the clonotypic chains of the TCR receptor undergo rearrangements so as to allow the expression of a functional receptor. Similarly, in B lymphocytes, the loci encoding the immunoglobulin (Ig) chains undergo rearrangements so as to allow the expression of a functional Ig.

The mechanism of V(D)J rearrangement is specific to T and B lymphocytes. The V, D and J genes encoding the TCR are distributed over long germinal portions within the various TCR loci. To give a protein, these genes must be associated in an exon by means of a gene rearrangement process, called V(D)J recombination. The principle of the recombination is based on the recognition of RSS sequences specific for the V(D)J genes, and the excision of the chromosomal region intercalated between the two rearranged genes. Each V and J gene has, at one of its ends, a recombination signal sequence (RSS). As for the D genes, they have them at both ends. RSSs are sequences recognized by the specific recombinase enzymes RAG I and RAG II, expressed specifically in lymphocytes. These proteins are the main players of rearrangement. Once associated with the HMG (high mobility group) proteins, the RAG enzymes recognize the RSS nonamer by virtue of their homeodomain and induce cleavage between the V, D, J gene segment and the heptamer, so as to generate a coding end and a signal end. Rearrangement is completed after ligation of the two V and J coding ends. This step is preceded by the action of the TdT enzyme and of a nuclease at the V-J junction. Once rearranged, the neoformed gene is transcribed and then spliced to give mRNA before being translated into a membrane protein.

A given TCR specifically recognizes a limited number of different antigenic peptides. Consequently, a vast repertoire of receptors is required in order to provide the individual's defense against the multiple infections that the latter may encounter in his or her environment. For this, the immune system has developed a mechanism of assembly of a large number of V, D, J gene segments positioned discontinuously in the genome. This "assembly" mechanism, called V(D)J recombination, is independent from one cell to the other and makes it possible to obtain a single "fragment" of gene encoding the TCR. This system makes it possible, with a modest number of genes, to generate a large number of different receptors. Each cell uses a combination of gene segments according to precise rules and obtains a potentially unique TCR chain.

Four major mechanisms contribute to generating the diversity of the repertoire: 1) a combinatorial diversity which corresponds to the first step of rearrangement between a V segment (a D segment) and a J segment; 2) a junctional diversity, generated at the junction between the rearranged gene segments; 3) somatic hypermutations in the rearranged V-J and V-D-J genes; 4) a diversity of pairing of the protein heterodimers TCRα×TCRβ or TCRγ×TCRδ.

The first step for generating diversity is based on the principle of V(D)J gene rearrangement (FIG. 1). The combinations resulting from the pairing of a fixed number of V, D and J genes form the combinatorial diversity. The calculation of this diversity consists in estimating the number of possible combinations mV×nD×pJ. The mechanism regulating V(D)J recombination is not random: it is spatiotemporally regulated during ontogenesis (Aude-Garcia et al., 2001; Jouvin-Marche et al., 1998; Pasqual et al., 2002; Rytkonen et al., 1996). Simple multiplication is not therefore sufficient to estimate the total number of expected gene combinations. This first step for generating diversity defines the order of magnitude of the repertoire. This is because, even if this step generates only a modest combination variability (of the order of a few thousand possible combinations compared with the maximum theoretical repertoire estimated at $10^{15}$ (Davis and Bjorkman, 1988)), the maximum combinatorial diversity is directly linked to the number of V, D and J genes initially available: the other two steps for generating diversity exponentially amplify the diversity of the primary repertoire.

Junction diversity makes it possible to generate a very large variability at the level of the CDR3 region of the receptor in contact with the antigenic peptide. Two mechanisms contribute to increasing the junctional diversity: 1) the first mechanism is due to the addition of P (for palindromic) nucleotides, originating from the resolution of the hairpin of the rearranged segments (Fugmann et al., 2000). The diversity generated is not as great as that originating from the second mechanism involving the terminal deoxynucleotidyl transferase enzyme; 2) TdT produces a substantial diversity, by randomly adding N nucleotides at the 3' end of each coding segment, without the need for a genomic template (Bogue et al., 1992). Studies on the TdT −/− mouse have made it possible to estimate that, in these animals, the TCRαβ repertoire represents only 5% to 10% of the normal repertoire and therefore that TdT is responsible for 90% of the generation of the total diversity of TCRαβ. In addition, these results have shown that the length of the CDR3s in the TCRβ transcripts are clearly reduced, unlike the CDR3 of the TCRα transcripts. This observation verifies, as expected, a greater contribution of TdT to V-D-J recombinations than to V-J rearrangements (Cabaniols et al., 2001).

The mechanism of secondary rearrangements contributes to "conserving" diversity: the junctional diversity represents the greatest factor of amplification of the diversity of the repertoire, but if there was not the mechanism of secondary rearrangement for saving ⅔ of the thymocytes having interrupted their reading frame, this benefit in terms of diversity would represent a considerable cost for the organism, even before the positive selection step. These nonproductive rearrangements cannot give a functional TCR protein. The cell then has the possibility of attempting a second rearrangement with the V(D)J genes still available on the locus. The property of concentric opening of the TRAD locus promotes this process, leaving the cell with the most possible chances, since the first rearrangements carried out by the cell take place between a pair of V-J genes close to one another (Huang and Kanagawa, 2001; Pasqual et al., 2002; Wang et al., 1998). If these first rearrangements are not productive, the cell has the possibility of attempting rearrangements on its second chromosome, or else of using the V and J genes available on either side of the first rearrangement. Thus, the secondary rearrangements allow the survival of a large number of cells which, at the end of a first nonproductive rearrangement, should have been eliminated.

Somatic hypermutations (SHMs) take place during B lymphocyte differentiation in the lymph nodes, when an antigen is encountered (Berek et al., 1985). The SHMs are located in "hot spot motifs" of the rearranged V-J and V(D)J genes of Igs (Chaudhuri et al., 2003; Oprea and Kepler, 1999), but also, in certain cases, in rearranged V-J and V(D)J genes of TCRs (Kotani et al., 2005). The TCR can be the target of SHMs in the variable genes, if the lymphocyte overexpresses the AID (activation-induced cytidine diaminase) enzyme which is normally specific for B lymphocytes. Under normal circumstances, the TCR does not undergo SHM since the T lymphocyte quite simply does not synthesize AID. Nevertheless, if the T lymphocyte starts to express it, the TCR is as sensitive to this enzyme as the BCR since it possesses all the sequence on which it acts. Overall, it is described in the literature that this mechanism induces an additional diversity by a factor of 1000 with the objective of increasing the chances of recognizing an antigen.

The diversity derived from the pairing between a TCRα chain and a TCRβ chain can be estimated by multiplying the number of different combinations of a TCRα chain by the number of possible combinations for the TCRβ chain. The diversity generated by this mechanism is directly dependent on the number of primary combinations that is obtained during the rearrangement. Specifically, if one examines the number of primary TCRγδ combinations in the mouse, without taking into account the junctional diversity, the result is only 40 TCRδ (=10V*2D*2J)×28TCRγ (=7V*4J)=1120 different combinations, whereas the same calculation gives $5.6 \times 10^6$ combinations for TCRαβ (calculated as follows: 102Vα*60Jα*33Vβ*2Dβ*14Jβ).

Complete sequencing of the human genome and of the mouse has recently made it possible to obtain the definitive maps of each of the TCR loci and consequently makes possible new genetic approaches for discovering the mechanisms of regulating recombination. Each cell has 4 loci capable of rearranging TCR genes. In humans and mice, the TCRα and TCRδ chains are rearranged in two associated loci on the same chromosome 14. The human TCRγ and TCRβ loci are on chromosomes 7 (or 13 in the mouse) and 7 (or 6 in the mouse), respectively (see table 1).

TABLE 1

Comparative table of the principal known characteristics of the 4 loci in humans and BALB/c mice (according to the IMGT data, MP Lefranc).

| Chain | TCRα | | TCRδ | | TCRβ | | TCRγ | |
|---|---|---|---|---|---|---|---|---|
| Species | Human | Mouse | Human | Mouse | Human | Mouse | Human | Mouse |
| Chromosome | 14q11.2 | 14c1 | 14q11.2 | 14c1 | 7q34 | 6A-C | 7p14 | 13A2-3 |
| Locus size | 1000 Kb | 1500 Kb | 1000 Kb | 1500 Kb | 620 Kb | 700 Kb | 160 Kb | 205 Kb |
| Number of V genes | 54 | 102 | 6 + nVa | 10 + nVa | 63-67 | 33 | 12-15 | 7 |
| Number of V families | 41 | 23 | 6 + nVa | 10 + nVa | 30 | 30 | 6 | 7 |
| Number of D genes | — | — | 3 | 2 | 2 | 2 | — | — |
| Number of J genes | 61 | 60 | 4 | 2 | 6 + 7 | 7 + 7 | 5 | 4 |
| Number of C genes | 1 | 1 | 1 | 1 | 2 | 2 | 2 | 4 |
| Number of pseudo V transcription rearrangement | 8 | 15 | 0 | 0 | 12-13 | 13 | — | — |
| | — | — | 0 | 0 | — | — | — | — |
| Number of pseudo J transcription rearrangement (P-R) | 8 | 6 | 0 | 0 | 2 | — | 0 | — |
| | 8 | 16 | 0 | 0 | 2 | 2 | 0 | — |
| Maximum combinatorial V(D)J without P-R | 54V * (61 J-8PR) = 2915 | 102V * (60J-16PR) = 4488 | 6V * 3D * 4J = 72 | 10V * 2D * 2J = 40 | (67V * D1 * 6J1 * 2C) + (67 * D1 * (8J2-2PR) * C1 + 67 * D2 * (8J2-2PR) * C2 = 804 + 402 + 402 = 1608 | (33V * D1 * 7J1-PR * 2C) + (33 * D1 * (7J2-1PR) * (C1 + 33 * D2 * (7J2-1PR) * C2 = 396 + 198 + 198 = 792 | 15 * 5 = 75 | 7 * 4 = 28 |

Observation #1: the dashes (-) indicate the absence of exhaustive studies for counting with certainty the number of rearrangement pseudogenes.

Observation #2: estimation of the TCRβ combinations. According to the structure of the TCRβ locus in humans, the genes rearranged on the D1 segment can rearrange on the J1.1-J1.6 segments and are then spliced with BC1 or BC2. They can also rearrange on the second set of segments J2.1-J2.8, but are then only spliced on BC2. If it is the D2 segment that is used, only the set J2.1 to J2.8 can be used, and the splicing will take place on the BC2 chain. This results in a combinatorial diversity that is fractionated according to the D1 or D2 segment chosen during the D-J rearrangement: (67V*1D1*6J1*2BC)+(67*1D1*(8J2-2PR)*1BC1)+ 67*1D2*(8J2-2PR)*1BC2=1608 possible combinations.

V(D)J gene nomenclature has changed several times over the past few years. The name of the genes, which was first of all assigned according to the order in which they were discovered, is now defined as a function of their position in the locus. The latest nomenclature is that of IMGT (http://imgt.cines.fr), which arranges the V families logically with respect to one another and intuitively classifies the members of a family on the locus. This IMGT nomenclature implies that all the V genes are known. The TRAV1 gene is the furthest from the AJ segments. It is the most upstream (on the 5' side) gene of the V region. The closer one gets to the J region, the higher the V-family number: thus, the human TRAV41 family is the closest to the AJ region. The members of a family have a name made up of the number of the family and then the number of the member. For example, TRAV8.1 is the most upstream (5') member of the TRAV8 family, whereas the TRAV8.6 member is the most downstream (3') on the V region. In the subsequent text, the IMGT nomenclature is used.

The diversity of the repertoire of immunoglobulins produced by B lymphocytes is the result of the same mechanisms as those described above for T lymphocytes.

Measurement of the immunological diversity makes it possible, inter alia, to study the mechanisms for setting up the immune repertoire, homeostasis, the T or B lymphocytes involved in an immune response, or in a leukemia, or else to evaluate the immunodeficiency induced by a treatment or, conversely, the specific immune system activation. This list is not exhaustive.

The study of the immune repertoire of a lymphocyte population has led to the development of several multiparametric approaches making it possible both to measure the degree of diversity and to identify the presence of certain specific T or B clones. Some approaches developed by immunologists for evaluating these various degrees of diversity are listed below according to the principle and the "degree" of diversity measured.

Measurement of V Diversity
  By cytometry (Van den Beemd, van Dongen et al. 2000).
  By Q-PCR at the genomic and transcriptomal level (Fuschiotti et al., 2007; Lang et al., 1997; Pasqual et al., 2002).
Measurement of CDR3 Junctional Diversity:
  By Immunoscope® (Cochet et al., 1992; Pannetier et al., 1995).
  By Q-PCR coupled to immunoscope (TcLandscape®)
  By sequencing.
  By the Amplicot method at the genomic level (Baum and McCune, 2006).
  By DNA chip (Bonarius et al., 2006).
Study of Somatic Hypermutations (SHMs):
  By PCR/sequencing (Hamblin et al., 1999).
  Indirect Measurement Via the Decrease in TREC Excision Circles
  By PCR (Douek et al., 1998).
  By Q-PCR (Pham et al., 2003).

While some of these approaches have already proved their worth in fundamental research, in particular Immunoscope® (Pannetier, C., J. Even, et al., 1995) or flow cytometry (Van den Beemd, van Dongen et al., 2000), there still remains a certain number of scientific and technical validations to be provided in order to evaluate the relevance of the use thereof as a medical biomarker. Faced with the complexity of the immune system, the scientist would need to couple complementary technological approaches in order to decode all the information contained in the immune repertoire and relevant to a given pathological condition.

Other methods, based on the use of PCR specifically amplifying nucleic acid segments characteristic of certain rearrangements, have been described.

For example, U.S. Pat. Nos. 5,296,351 and 5,418,134 present a method for detecting lymphoid leukemias or B or T lymphomas, based on the amplification of sequences encoding immunoglobulins and/or T receptors, using "consensus" primers for simultaneously amplifying several V-J rearrangements.

Application WO2005/056828 describes a method based on the use of multiplex PCRs, which are polymerase chain reactions (PCRs) in which several different fragments, corresponding to different rearrangements, are amplified, with the same pair of primers, from genomic DNA.

However, none of the methods described above makes it possible to obtain, in a reasonable amount of time, resolution of the V(D)J rearrangements of the immune repertoire, nor even resolution of all the rearrangements that have occurred in a given locus. This is because the number of multiplex PCRs to be carried out for this would be too high for it to be possible to envision routine use of these methods.

The present invention is based on several improvements of the method described in application WO2005/056828, for enabling the analysis of a larger number of V(D)J rearrangements in a reliable, easy and rapid manner. Consequently, the methods of the present invention constitute tools of choice for analyzing the diversity of the repertoire of B and/or T lymphocytes in a sample in numerous applications, such as immunomonitoring in preclinical or clinical phases, for studying the effect of a treatment on the (re)constitution of the immune system, personalized diagnosis, prognosis, in particular in oncology-hematology, etc.

The present invention therefore relates, firstly, to a method for the in vitro analysis of the diversity of the repertoire of T and/or B lymphocytes in a human or animal individual, from genomic DNA originating from a biological sample from said individual, comprising the following steps:

A) amplification of fragments of said genomic DNA by multiplex PCRs, at least one of which is a multi-n-plex PCR with ≥2, carried out with a combination of at least 3 primers, constituting at least 2 pairs of primers having the following characteristics:

(i) each pair of primers is constituted of a primer which specifically hybridizes upstream of and/or in a given V or D gene and of a primer which specifically hybridizes downstream of and/or in a given J gene, so as to allow the amplification, with each pair of primers, of at least two fragments characteristic of two distinct V-J or D-J rearrangements;

(ii) the primers (i.e. all the primers used in the same amplification reaction) are thermodynamically compatible;

(iii) the primers are chosen in such a way that the fragments amplified with the first pair of primers can be distinguished from the fragments amplified with the second pair of primers;

B) detection of the amplification products obtained in step A);
C) interpretation of the results.

For the implementation of this method, the genomic DNA is preferably purified. However, those skilled in the art can, depending on the progress in technology, choose to work on crude samples. Any biological sample that may contain lymphocytes can be used; by way of nonlimiting examples of samples that can be used, mention may be made of blood, thymus, lymph node, spleen, PBMC, liver, skin, urine, etc., samples.

The implementation of the method above requires a high-performance Taq polymerase enzyme. It is in particular preferable to use an enzyme having the ability to amplify large fragments at high speed and that can "pass" over GC-rich regions. More preferably, in order to carry out multi-n-plex PCR reactions in the context of the present invention, those skilled in the art will choose a polymerase having the following characteristics:
(i) it is capable of amplifying fragments of several tens of kb;
(ii) its elongation rate is at least 1 kb/minute;
(iii) its robustness is such that it does not introduce more than one error per kb, on average. By way of nonlimiting examples of enzymes that can be used to implement this method, mention may be made of the HerculaseII polymerase from Stratagene and the Iproof polymerase from Biorad.

In the present text, the term "multi-n-plex PCR" refers to a polymerase chain reaction having n degrees of multiplexing, i.e. using, in the same reaction, n pairs of different primers, each allowing the amplification of at least two DNA fragments characteristic of at least two different chromosomal rearrangements. For example, in the TRA locus, a multi-2-plex PCR reaction can be carried out using a "sense" primer which specifically hybridizes upstream of and/or in a given $V_x$ gene and two "antisense" primers which specifically hybridize downstream of and/or in two distinct $J_y$ and $J_z$ genes, allowing at least the amplification, in a single reaction, of fragments characteristic of the $V_xJ_y$, $V_xJ_{y+1}$, $V_xJ_z$ and $V_xJ_{z+1}$ rearrangements. Of course, a multi-n-plex PCR reaction is possible only if the primers of the n pairs used are thermodynamically compatible. The thermodynamic compatibility of primers is a notion well known to those skilled in the art, who possess algorithms for verifying it. It implies in particular that the various primers have identical or close melting temperatures (Tm). In addition, the various primers should not hybridize to one another, nor form hairpins. In the rest of this text, the constraints linked to the compatibility of the primers for their simultaneous use in a multi-n-plex PCR will not be systematically recalled, given that they are part of the general knowledge of any molecular biologist.

In the present text, a "primer which specifically hybridizes downstream of and/or in a given J gene" may be referred to, by misuse of language, as "primer specific for the J gene". Similarly, a "primer which specifically hybridizes upstream of and/or in a given V gene" may be referred to as "primer specific for the V gene". As regards the V genes, it is important to note that they are, for most of the loci, grouped together in families, according to their degree of homology. In this case, a "primer specific for a given V gene" can in reality denote a primer which specifically recognizes all the members or some members of a family of V genes. Examples of primers specific for a family of V genes are given hereinafter. Moreover, when a pair of primers makes it possible to detect the rearrangements of all the members or of some members of the same family, these rearrangements may be referred to, by misuse of language, as "the rearrangement", "the amplicon" or "the PCR product".

The method above can in particular be applied to the analysis of the combinatorial diversity of the V-J rearrangements of at least one genetic locus chosen from the loci TRA, TRB, TRG, TRD, IgH, IgK, IgL, etc.

In one particular implementation of the method according to the invention, at least one primer of each pair of primers is labeled. When a primer is common to several pairs of primers used in the same multi-n-plex PCR, the other primer of each pair will preferably be labeled. Various labels, making it possible to distinguish the products of amplification by each of the pairs, can advantageously be used. Those skilled in the art possess a large variety of labels that can be used for labeling the primers, among which mention may be made of colorimetric labels, fluorescent labels, enzymatic labels, radioactive labels, biotin, streptavidin, etc.

According to one particular implementation of the method described above, step B) comprises a step of real-time measurement of the amplification of the DNA fragments; the interpretation of the amplification curves obtained is then carried out in the following way:
(i) if one or a few curves, the number thereof being less than half the curves, and in particular equal to 1, 2 or 3, exhibit(s) a shift compared with the other curves, such that the other curves exhibit a point of inflexion at least 2 cycles after the point of inflexion of the first curve, preferably at least 3 or 4 cycles, or show(s) no amplification, the result indicates the presence of clonal or oligoclonal lymphoproliferation;
(ii) if, on the contrary, all the curves exhibit a point of inflexion at the same cycle, or within a maximum shift of 2 or 3 amplification cycles, the result makes it possible to discard the hypothesis of lymphoproliferation of a clone resulting from one of the rearrangements corresponding to the amplified fragments.

In this implementation, and according to the technology used to carry out the quantitative PCR (TaqMan®, measurement of the incorporation of a fluorescent intercalating agent such as SYBR-green®, etc.), the amplification measured is either the sum of the amplifications carried out with all the pairs of primers used in the same reaction (in the case of the use of SYBR-green®), or, on the contrary, the amplification by each of the pairs of primers, separately (in the case of the TaqMan® technology, using primers labeled differently for each of the pairs). Be that as it may, the inventors have observed that, when a given lymphocyte population is over-represented in a sample, the amplification of the fragment corresponding to the rearrangement that has occurred in these lymphocytes is efficient, whereas the amplification of the fragments corresponding to the other rearrangements results in a shifted curve, or even in a failure to amplify (flat curve).

When the amplification measurement is carried out with a fluorescent intercalating agent, the method described above may also comprise a step (optional) of confirmation of lymphoproliferation, by continuous measurement of the fluorescence in each tube during an increase in temperature between 40° C. and 95° C., the observation of a predominant peak being indicative of the presence of a predominant amplicon and therefore of a lymphoproliferation, whereas the observation of several peaks of similar sizes indicates, on the contrary, lymphocyte diversity.

This method also makes it possible to carry out a step of measurement of the molecular diversity of the rearrangements observed at the level of the genomic DNA, by measuring the molecular diversity of the amplicons. This optional step adds an additional degree of information since the "molecular diversity" results from the combination of the junctional diversity (CDR3), the combinatorial diversity (V-J) and the diversity derived from the somatic hypermutations. It is measured, according to the invention, in the following way:
(i) after dehybridization of the amplicons at 95° C., the temperature of the amplification products is rapidly brought back below 40° C., preferably to 30° C. or below; this decrease in temperature can be carried out in the thermocycler, or by placing the tube in ice for a few minutes; the drop in temperature should be carried out in a short period of time, preferably less than 2 minutes, even more preferably less than 30 seconds;
(ii) the fluorescence is measured regularly and preferably continually during the rehybridization;
(iii) a rapid rehybridization (of the order of a second) is indicative of the presence of a predominant amplicon, and therefore of clonal lymphoproliferation, whereas a slower rehybridization (of the order of several tens of seconds, or even minutes) is indicative of good molecular diversity (at least several tens of molecules, or even several thousand).

According to another preferred implementation of the method of the invention, step B) of detection of the amplification products comprises a step of separation of said products according to their size. Those skilled in the art possess several techniques for separating amplicons according to their size. By way of nonlimiting examples, mention may be made of agarose or polyacrylamide gel electrophoresis, or capillary electrophoresis, which has the advantage of being more readily automatable. The amplicons separated according to their size can be detected by any means known to those skilled in the art, in particular by virtue of labels bonded to the primers, or by using fluorescent intercalating agents such as ethidium bromide, SYBR-green®, etc. The resolution of the amplicons and the detection thereof make it possible to identify the various chromosomal rearrangements having given rise to amplification. The use of a semi-quantitative or quantitative amplification technique makes it possible, in addition, to determine the frequency, in the sample tested, of lymphocytes having undergone the V(D)J rearrangement corresponding to each of the amplicons observed. This implementation of the invention therefore makes it possible to finely evaluate the combinatorial diversity of a part of the immune repertoire, this part being all the greater the higher the number of rearrangements capable of giving rise to amplification, the latter parameter being dependent on the number of multiplex PCRs carried out, on their degree of multiplexing and on the choice of the primers.

Those skilled in the art may decide to implement the method of the invention by carrying out a first evaluation of the diversity of the lymphocyte repertoire by simple real-time measurement of the amplification of the DNA fragments, as mentioned above, and by subsequently carrying out a separation of the amplicons according to their size so as to obtain further information on the distribution of the various rearrangements in the lymphocyte population. In the case where lymphoproliferation is detected by quantitative multi-n-plex PCR, the second step, of detection, by separation of the amplicons according to their size, would make it possible in particular to identify the V(D)J rearrangement present in the proliferative clone or the few proliferative clones. It is important to note that this approach does not require additional PCRs to be carried out, since it is then sufficient to use the products of the PCRs already carried out, in order to separate the amplicons thereof according to their size. Alternatively, those skilled in the art can choose not to carry out the first step of searching for lymphoproliferation by real-time PCR, and to directly carry out the separation of the amplification products. Those skilled in the art will then directly obtain the name and the frequency (intensity) of the various V(D)J rearrangements having taken place in the lymphocyte population tested.

In this implementation of the invention, the pairs of primers used in combination in each multi-n-plex PCR reaction with n≥2 are preferably chosen in such a way that the majority of the amplicons obtained can be resolved according to their size. The term "resolved" is herein intended to mean that each of the amplicons can be observed individually, following size-separation thereof by means of an electrophoresis method or any other method. When amplicon sizes are too close, it is not always possible to discern them distinctly with separation conditions that are compatible with the conditions for "resolving" all the other amplicon sizes. The various amplicons obtained with a given pair of primers correspond to different rearrangements and are therefore of significantly different sizes. Care should therefore be taken to ensure that at least some of the products of amplification by a pair of primers have sizes different from the products of amplification by the other pair(s) of primers. Of course, the size differences for obtaining good band resolution depend on the technology used. By way of indication, size differences of 10% generally make it possible to obtain good resolution. Ideally, the primers are chosen so as to allow the resolution of all the amplicons. However, if some bands, corresponding to amplicons obtained with various pairs of primers in the same multi-n-plex PCR, are too close or overlap, other means can be used to identify and quantify the corresponding rearrangements. For example, distinct labels can be bonded to the corresponding primers (at least to one primer of each pair concerned).

In one particular implementation of the invention, at least one multi-n-plex PCR (with n≥2) is carried out using a combination of at least 3 primers constituting at least 2 pairs of primers comprising a common "sense" primer specific for a given V gene, each pair of primers also comprising an "antisense" primer specific for a given J gene. More particularly, this method may be advantageously implemented by carrying out several multi-2-plex PCRs with triplets of primers each constituted of a sense primer which specifically hybridizes upstream of and/or in a given V gene and of two antisense primers which specifically hybridize downstream of and/or in two distinct J genes.

An alternative way to combine the primers for carrying out the multi-n-plex PCRs according to the invention is to combine at least 3 primers constituting at least 2 pairs of primers comprising a common antisense primer specific for a given J gene, each pair of primers also comprising a sense primer specific for a given V gene.

The TRB locus has a particular configuration, since the J genes are arranged in two groups (or clusters) distant from one another, the first group (in the 5'→3' direction) comprising the BJ1.1 to BJ1.6 genes, and the second group comprising the BJ2.1 to BJ2.7 genes. Taking advantage of this particular configuration, the inventors have determined parameters of choice for the primers for obtaining excellent resolution of the amplicons corresponding to the rearrangement of a given V gene with all or a part of the J genes. According to this particular implementation of the invention, at least one multi-n-plex PCR reaction with n≥2 is carried out in order to analyze certain rearrangements of the TRB locus, using a combination of at least 3 primers constituting at least 2 pairs of primers having the following characteristics:
(i) the two pairs of primers comprise a common sense primer which specifically hybridizes upstream of and/or in a given V gene and each comprise an antisense primer which specifically hybridizes downstream of and/or in a given J gene;
(ii) the two antisense primers specifically hybridize downstream of and/or in two genes $J_y$ and $J_z$ belonging to two distinct groups of J genes of the TRB locus; and
(iii) the distance between the region of hybridization of the antisense primer specific for the $J_y$ gene and the start of said $J_y$ gene is greater than the distance between the region of hybridization of the antisense primer specific for the $J_z$ gene and the start of the first J gene of the group of genes of said $J_z$ gene.

In the preceding text, the "distance between the region of hybridization of the antisense primer specific for the $J_y$ gene and the beginning of said $J_y$ gene" denotes the distance between the 3' end of said region of hybridization (therefore corresponding, in the amplicon, to the 5' end of the antisense primer specific for the $J_y$ gene) and the first coding base of the $J_y$ gene (located immediately after the RSS recombination sequence).

In one preferred implementation of this aspect of the invention, $J_y=J_{1.6}$ and $J_z=J_{2.7}$. If $V=V_x$, the bands characteristic of the rearrangements $V_xJ_{2.7}$, $V_xJ_{2.6}$, $V_xJ_{2.5}$, $V_xJ_{2.4}$, $V_xJ_{2.3}$, $V_xJ_{2.2}$, $V_xJ_{2.1}$, $V_xJ_{1.6}$, $V_xJ_{1.5}$, $V_xJ_{1.4}$, $V_xJ_{1.3}$, $V_xJ_{1.2}$ and $V_xJ_{1.1}$ will therefore be seen, in increasing order of size. Where appropriate, if the polymerase used is particularly effective, a high-molecular-weight band corresponding to the $V_xJ_{1.n}$ arrangements amplified with the primer which hybridizes downstream of the $J_{2.7}$ gene will also be observed. Alternatively, the method may be implemented with $J_y=J_{2.7}$ and $J_z=J_{1.6}$, which will result in the bands characteristic of the rearrangements $V_xJ_{1.6}$, $V_xJ_{1.5}$, $V_xJ_{1.4}$, $V_xJ_{1.3}$, $V_xJ_{1.2}$, $V_xJ_{1.1}$, $V_xJ_{2.7}$, $V_xJ_{2.6}$, $V_xJ_{2.5}$, $V_xJ_{2.4}$, $V_xJ_{2.3}$, $V_xJ_{2.2}$ and $V_xJ_{2.1}$, in increasing order, being observed.

According to one preferred implementation of the method described above for analyzing certain rearrangements of the TRB locus, at least one multi-n-plex PCR reaction with n≥2 is carried out using a combination of at least 3 primers comprising the primers hTRBJ1.6 and hTRJB2.7 defined in the following way:

hTRBJ1.6 (CTTGGTGCATGGCTATGTAATCCTG, SEQ ID No 1) is an antisense oligonucleotide of 25 nucleotides which hybridizes between nucleotides 2341 and 2365 of the J1.6 gene of the TCRB locus; and hTRBJ2.7 (CTCGCCCTCTGCTCAGCTTTCC, SEQ ID No 2) is an antisense oligonucleotide of 22 nucleotides which hybridizes between nucleotides 214 and 235 of the J2.7 gene of the TCRB locus.

A method for determining the position of the various primers described in the present text, relative to various genes of the TCR or IgH loci, is explained in example 1 hereinafter. The genomic sequences disclosed in the "Ensembl Genome Browser" database can be used to identify primers that can be used in the context of the present invention.

The inventors have identified, in the TRB locus, 24 families of functional V genes. They have also shown that, by carrying out at least 23 multi-2-plex PCRs, it is possible to analyze at least 75% of the V(D)J rearrangements of the TRB locus, involving more than 85% of the V families. The invention therefore relates more particularly to a method for analyzing at least 75%, preferably at least 80% of the V(D)J rearrangements of the TRB locus by carrying out 23 or 24 multi-n-plex PCRs with n≥2 using combinations of at least 3 primers, each combination of primers comprising the hTRBJ1.6 and hTRBJ2.7 primers, defined above, and at least one hTRBV primer chosen from the primers defined in the table below:

TABLE 2

| Name of gene | Name of primer | Size (nt) | Distance between the 5' end of the primer and the end of the V gene (bp) | Sequence | SEQ ID No. |
|---|---|---|---|---|---|
| TRBV2 | hTRBV2up2 | 26 | 255 | CACACAGATGGGACAGGAAGTGATCT | 3 |
| TRBV4 | hTRBV4up_ex | 23 | 100 | GCTTCTCACCTGAATGCCCCAAC | 4 |
| TRBV5.1, 3, 4, 5, 6, 8 | hTRBV5up_ex1/2 | 25 | 256 | CTGATCAAAACGAGAGGACAGCAAG | 5 |
| TRBV5.7 | hTRBV5up_ex2/2 | 25 | 256 | CTGATCAAAACGAGAGGACAGCAAG | 6 |
| TRBV6.4 | hTRBV6up_ex2/2 | 23 | 279 | GATCACCCAGGCACCAACATCTC | 7 |
| TRBV7.2 | hTRBV7up_ex2/3 | 25 | 301 | CAGATCACACAGGAGCTGGAGTCTC | 8 |
| TRBV7.9 | hTRBV7up_ex3/3 | 27 | 303 | CACAGATCACGCAGATACTGGAGTCTC | 9 |
| TRBV9 | hTRBV9up_ex | 23 | 92 | CGCACAACAGTTCCCTGACTTGC | 10 |
| TRBV11 | hTRBV11up_ex | 27 | 120 | TTCACAGTTGCCTAAGGATCGATTTTC | 11 |
| TRBV12.1 | hTRBV12.1up1 | 27 | 196 | TTCTCTGGTACAGACAGACCTTTGTGC | 12 |
| TRBV12.2 | hTRBV12.2up1 | 27 | 196 | TTTTCTGGTACAGAGATACCTTCGTGC | 13 |

TABLE 2-continued

| Name of gene | Name of primer | Size (nt) | Distance between the 5' end of the primer and the end of the V gene (bp) | Sequence | SEQ ID No. |
|---|---|---|---|---|---|
| TRBV13 | hTRBV13up1 | 25 | 356 | GTTGCTGAAGTGTCAAACTCTCCCG | 14 |
| TRBV14 | hTRBV14up_ex | 24 | 271 | TCCCCAGCCACAGCGTAATAGAGA | 15 |
| TRBV15 | hTRBV15up_ex | 24 | 163 | CCCCAAAGCTGCTGTTCCACTACT | 16 |
| TRBV16 | hTRBV16up1 | 22 | 295 | CTCCTGGTGAAGAAGTCGCCCA | 17 |
| TRBV18 | hTRBV18up1 | 22 | 46 | TAGTGCGAGGAGATTCGGCAGC | 18 |
| TRBV19 | hTRBV19up2 | 24 | 217 | CTGGGAGCAAGTGAGTCCTGGGT | 19 |
| TRBV20 | hTRBV20-1up_ex | 24 | 91 | TCATCAACCATGCAAGCCTGACCT | 20 |
| TRBV24 | hTRBV24up_ex | 24 | 96 | AGTGTCTCTCGACAGGCACAGGCT | 21 |
| TRBV25 | hTRBV25up_int | 23 | 273 | CCTCTTTGTTGGGTTTGTGCCTG | 22 |
| TRBV27 | hTRBV27up2 | 22 | 312 | GTCCCCTTCCTTTACAGGCCCC | 23 |
| TRBV29 | hTRBV29up_G | 21 | 91 | CCATCAGCCGCCCAAACCTAA | 24 |
| TRBV30 | hTRBV30up1 | 26 | 148 | TGCTCTTCTACTCCGTTGGTATTGGC | 25 |

This implementation of the invention enables an analysis of at least 80% of the V(D)J rearrangements of the TRB locus, i.e., for more than 85% of the families of functional V genes, determination of the frequency of use of the genes of each functional V family with each functional J family of this locus (without information on the nature of the D gene used in these rearrangements, nor on the use of each member of a given V family, nor on the junctional diversity of the rearrangements, etc.). Coupling with a real-time measurement of the amplification by multi-n-plex PCR also makes it possible to estimate the molecular diversity.

According to another particular implementation of the method of the invention, this method enables the in vitro detection of incomplete D-J rearrangements in a genetic locus chosen from the TRB and IgH loci. The detection of the incomplete rearrangements is important since, even if they are nonfunctional, they constitute, in certain cases, the only signature of a lymphoproliferative population.

This method can in particular be suitable for analyzing incomplete DJ rearrangements of the human TRB locus, by carrying out at least one multi-n-plex PCR reaction with n≥2 with a combination of at least 3 primers constituting at least 2 pairs of primers having the following characteristics:
(i) the two pairs of primers comprise a common sense primer which specifically hybridizes upstream of and/or in a given D gene and each comprise an antisense primer which specifically hybridizes downstream of and/or in a given J gene;
(ii) the two antisense primers which specifically hybridize downstream of and/or in two genes $J_y$ and $J_z$ belonging to two distinct groups of J genes of the TRB locus; and
(iii) the distance between the region of hybridization of the antisense primer specific for the $J_y$ gene and the start of said $J_y$ gene is greater than the distance between the region of hybridization of the antisense primer specific for the $J_z$ gene and the start of the first J gene of the group of genes of said $J_z$ gene.

In particular, the hTRBJ1.6 and hTRBJ2.7 primers defined above can be combined with a sense primer which specifically hybridizes upstream of and/or in a given D gene, in order to carry out a multi-n-plex PCR reaction with n≥2.

Owing to the configuration of the TRB locus, it is possible to analyze all the incomplete DJ rearrangements of this locus with only 2 multi-2-plex PCRs.

Thus, it is possible to analyze all the incomplete rearrangements of the human TRB locus by carrying out (i) a multi-2-plex PCR using a triplet of primers constituted of the hTRBJ1.6 and hTRBJ2.7 primers and of an hTRBD1 primer, and (ii) a simple multiplex PCR using the pair of primers constituted of the hTRBJ2.7 primers and of an hTRBD2 primer, by choosing, for example, the hTRBD1 and hTRBD2 primers from the primers defined in the table below:

TABLE 3

| Name of gene | Oligo-nucleo-tide name | Size (nt) | Distance between the 5' end of the primer and the end of the D gene (bp) | Sequence | SEQ ID No. |
|---|---|---|---|---|---|
| TRBD1 | hTRBD1up1 | 25 | 325 | TTCTCTATAAGGACATGCCCCAACG | 26 |
| TRBD1 | hTRBD1up2 | 23 | 289 | TTGGAGAGGGGTGGGTACTGGAG | 27 |
| TRBD2 | hTRBD2up1 | 26 | 322 | CTCCCACCCACTTCACTATAAATGCC | 28 |
| TRBD2 | hTRBD2up2 | 21 | 290 | GAGCAGGTGGGCACAGTGAGC | 29 |

When the analysis of the incomplete rearrangements of the TRB locus is coupled with the analysis of other rearrangements, the multiplex PCRs described above, in particular the simple multiplex PCR, can be combined with other amplification reactions, carried out in the same tube (thus increasing the degree of multiplexing and reducing the number of reactions necessary for analyzing a given number of rearrangements).

According to one preferred implementation of the invention, the method combines the analysis of the V(D)J rearrangements of the TRB locus and that of the incomplete rearrangements of this locus, by implementation of the suitable variants described above. The primers described above for this analysis are suitable for the analysis of the rearrangements of this locus in humans, but this method can be transposed, without any difficulty, to animals, for example to mice. Primers that can be used in mice are described, by way of example, in the experimental section which follows.

According to another aspect of the invention, the method makes it possible to analyze the rearrangements of 95% of the J genes of the human TRA locus with a given V gene of the same locus, by carrying out, in step A), between 3 and 6 multi-n-plex PCRs with n≥2, with combinations of primers each constituted of a primer which hybridizes upstream of and/or in said V gene and of one or two pair(s) of antisense primers chosen from the pairs (hTRAJ56, hTRAJ41), (hTRAJ37, hTRAJ33), (hTRAJ48, hTRAJ29), (hTRAJ24, hTRAJ18), (hTRAJ53, hTRAJ11) and (hTRAJ7, hTRAJ3), said primers being defined in the table below:

TABLE 4

| Name of gene | Oligo-nucleo-tide name | Size (nt) | Distance with the start of the J gene in bp | Sequence | SEQ ID No. |
|---|---|---|---|---|---|
| hTRAJ56 | hTRAJ56do | 24 | 883 | TCCCCCAAGTATTGCATTTGGATT | 30 |
| hTRAJ41 | hTRAJ41do | 25 | 443 | AACTCAACAGGGTCCTTGCCACTTA | 31 |
| hTRAJ37 | hTRAJ37do | 28 | 351 | CCACCCACATTTGATGTTTTTATTTCTT | 32 |
| hTRAJ33 | hTRAJ33do | 24 | 98 | TAGTGTCTCCTCTCCCGTGCAGTC | 33 |
| hTRAJ48 | hTRAJ48do | 28 | 43 | GTTCCAGTCCCAAAGGTTAATTTCTCAT | 34 |
| hTRAJ29 | hTRAJ29do | 24 | 300 | AGAACAAGCTGGAGGCAACTAGGC | 35 |
| hTRAJ24 | hTRAJ24do | 28 | 227 | AACACCAGTCTGATCTCTCATTTTTGCT | 36 |
| hTRAJ18 | hTRAJ18do | 29 | 147 | CAAGACTAAAGGAGTTAATTCATCTCCCC | 37 |
| hTRAJ53 | hTRAJ53do | 24 | 200 | AATCCCTCTGATGGGCACCATATC | 38 |
| hTRAJ11 | hTRAJ11do | 20 | 88 | ACATGGGTGGGATGGGGTCA | 39 |
| hTRAJ7 | hTRAJ7do | 20 | 478 | TGGGAGTAAAGGGCTGGGGC | 40 |
| hTRAJ3 | hTRAJ3do | 25 | 329 | AACCTCAATTCCAGGCAGCAGTATC | 41 |

This analysis can in particular be carried out using 6 multi-2-plex PCRs. Alternatively, it can be carried out using 3 multi-4-plex PCRs performed with combinations of primers each comprising a sense primer specific for a V gene and a quadruplet of primers chosen from the following quadruplets: (hTRAJ56, hTRAJ41, hTRAJ37, hTRAJ33), (hTRAJ48, hTRAJ29, hTRAJ24, hTRAJ18) and (hTRAJ53, hTRAJ11, hTRAJ7, hTRAJ3). Of course, the intermediate situations (4 multi-2-plex PCRs and 1 multi-4-plex PCR; 2 multi-2-plex PCRs and 2 multi-4-plex PCRs) are also envisioned.

In order to have more comprehensive information on the rearrangements of the TRA locus, it is proposed to carry out the method described above with at least three, but preferably 4, 5, 6 or more, primers which hybridize upstream of and/or in the distinct V genes, each located in a distinct region of the locus. It is important for the TRAV genes targeted by these primers to be well distributed in the locus, in order for the combinatorial diversity observed to be actually representative of all the rearrangements of this locus. Primers that can be used for this are defined in the table below:

TABLE 5

| Name of gene | Name of oligo-nucleotide | Size (bp) | Distance with the end of the V gene (bp) | Sequence | SEQ ID No. |
|---|---|---|---|---|---|
| TRAV1 | hTRAV1up_ex | 26 | 104 | GGTCGTTTTTCTTCATTCCTTAGTCG | 42 |
| TRAV3 | hTRAV3 | 22 | 377 | TCCCCTTCCCATTTTCCACTCG | 43 |
| TRAV4 | hTRAV4up_ex_testAn1 | 23 | 96 | CCCTGTTTATCCCTGCCGACAGA | 44 |
| TRAV10 | hTRAV10upn3 | 24 | 85 | CTGGATGCAGACACAAAGCAAAGC | 45 |
| TRAV12.2, 3 | hTRAV12.2, 3up1 | 27 | 114 | AATGAAGATGGAAGGTTTACAGCACAG | 46 |
| TRAV12.1 | hTRAV12.1up1 | 28 | 112 | ACAAAGAAGATGGAAGGTTTACAGCACA | 47 |
| TRAV14 | hTRAV14upn2 | 22 | 69 | CGCCAACCTTGTCATCTCCGCT | 48 |
| TRAV16 | hTRAV16upn5 | 27 | 118 | CTAGAGAGAGCATCAAAGGCTTCACTG | 49 |
| TRAV17 | hTRAV17upn2 | 22 | 40 | CGGGCAGCAGACACTGCTTCTT | 50 |
| TRAV19 | hTRAV19up | 24 | 144 | TCGTCGGAACTCTTTTGATGAGCA | 51 |
| TRAV21 | hTRAV21up | 24 | 91 | TGCCTCGCTGGATAAATCATCAGG | 52 |
| TRAV22 | hTRAV22up | 21 | 42 | CCCAGACCACAGACTCAGGCG | 53 |
| TRAV23 | hTRAV23upn2 | 28 | 130 | CGTCCAGATGTGAGTGAAAAGAAAGAAG | 54 |
| TRAV25 | hTRAV25upn3 | 27 | 154 | TGGACATCCCGTTTTTTGATACAGTT | 55 |
| TRAV27 | hTRAV27up | 27 | 138 | TGGTGACAGTAGTTACGGGTGGAGAAG | 56 |
| TRAV29 | hTRAV29up | 24 | 267 | AGCAAAATTCACCATCCCTGAGCG | 57 |
| TRAV30 | hTRAV30upn2 | 24 | 139 | TGAAGGGTGGAGAACAGAAGGGTC | 58 |
| TRAV35 | hTRAV35_int_up | 27 | 377 | GGCTGGGAAGTTTGGTGATATAGTGTC | 59 |
| TRAV36 | hTRAV36_int_upn2 | 27 | 304 | ACATTTTCTACACAGGGGTGAGCAGT | 60 |

TABLE 5-continued

| Name of gene | Name of oligo-nucleotide | Size (bp) | Distance with the end of the V gene (bp) | Sequence | SEQ ID No. |
|---|---|---|---|---|---|
| TRAV41 | hTRAV41_int_up | 28 | 368 | GCCCTCCTGAAAATGTGTAA AGAAATGT | 61 |

The implementation of the method by carrying out, for each of the 20 TRAV primers described in this table, 6 multi-2-plex PCRs (or 3 multi-4-plex PCRs, etc.) with the combinations described above in order to observe the rearrangements of 95% of the TRAJ genes with a V gene, makes it possible to observe between 50% and 75% of all the VJ rearrangements of the TRA locus.

Of course, those skilled in the art can transpose this method to the analysis of the TRA locus of an animal, for example to the murine TRA locus.

According to another aspect, the invention relates to a method for analyzing the rearrangements of all the J genes of the human TRG locus with at least 2 given genes $V_x$ and $V_y$ of the same locus, by carrying out, in step A), at least one multi-2-plex PCR with a triplet of primers constituted of 2 sense primers which hybridize upstream of and/or in said $V_x$ and $V_y$ genes and of the antisense primer hTRGJdo2 (ACATATGAGCCCTTTATGGAAGTCCG, SEQ ID No. 62) of 26 nucleotides which hybridizes in the J2 gene of the human TRG locus.

By way of examples of primers which hybridize upstream of and/or in a V gene of the human TRG locus, that can be used for implementing this aspect of the invention, mention may be made of the primers defined in the table below:

TABLE 6

| Name of gene | Oligo-nucleotide name | Size (nt) | Distance with the end of the V gene in bp | Sequence | SEQ ID No. |
|---|---|---|---|---|---|
| TRGV1.2 | hTRGV1.2up1 | 30 | 99 | TATTATACTTACGCAAGCACAAGGAACAAC | 63 |
| TRGV1.4 | hTRGV1.4up1 | 28 | 158 | TGTACTATGACTCCTACACCTCCAGCGT | 64 |
| TRGV1.5 | hTRGV1.5up1 | 23 | 287 | AAGGGGGAACGAAGTCAGTCACG | 65 |
| TRGV1.8 | hTRGV1.8up1 | 26 | 129 | GTGTTGGAATCAGGAATCAGTCGAGA | 66 |

This analysis can in particular be carried out by performing only simple multiplex PCRs, or multi-n-plex PCRs with n≥2, with, in the same reaction, a pair of primers specific for the TRG locus and a pair of primers specific for another locus.

The diversity of the rearrangements involved in the TRD locus can also be studied by means of a method according to the invention, by carrying out, in step A), a multi-2-plex PCR with a triplet of primers constituted of a primer which hybridizes upstream of and/or in a V gene of this locus and of the antisense primers hTRDJ1do5 and hTRDJ3do2, defined as follows:

hTRDJ1do5 (TGCCTCCTTAGATGGAGGATGCC, SEQ ID No. 67) is an antisense oligonucleotide of 23 nucleotides which hybridizes between nucleotides 90 and 112 of the J1 gene of the TRD locus; and hTRDJ3do2 (GCAAGGAGGCACGCATACTAGTTAGC, SEQ ID No 68) is an antisense oligonucleotide of 26 nucleotides which hybridizes between nucleotides 448 and 473 of the J3 gene of the TRD locus.

With this combination of primers, it is possible to analyze, using a single multi-2-plex PCR, the rearrangements of all the J genes of the human TRD locus with a given V gene. The complete analysis of all the VJ rearrangements of the TRD locus can therefore be obtained by carrying out a multi-n-plex PCR with n≥2, per TRDV family. By way of examples of primers specific for TRDV genes that can be used with the antisense primers hTRDJ1do5 and hTRDJ3do2 for imple-menting this aspect of the invention, mention may be made of the primers defined in the table below:

TABLE 7

| Name of gene | Name of primer | Size (nt) | Distance between the 5' end of the primer and the end of the V gene (bp) | Sequence | SEQ ID No. |
|---|---|---|---|---|---|
| TRAV12.1 | hTRAV12.1up1 | 28 | 112 | ACAAAGAAGATGGAAGGTTTACAGCACA | 69 |
| TRAV14 (TRDV4) | hTRAV14upn2 | 22 | 69 | CGCCAACCTTGTCATCTCCGCT | 70 |
| TRAV16 | hTRAV16upn5 | 27 | 118 | CTAGAGAGAGCATCAAAGGCTTCACTG | 71 |
| TRAV17 | hTRAV17upn2 | 22 | 40 | CGGGCAGCAGACACTGCTTCTT | 72 |
| TRAV21 | hTRAV21up | 24 | 91 | TGCCTCGCTGGATAAATCATCAGG | 73 |
| TRAV22 | hTRAV22up2 | 21 | 232 | CAGGAGGGAGCCAATTCCACG | 74 |
| TRAV23 (TRDV6) | hTRAV23upn2 | 28 | 130 | CGTCCAGATGTGAGTGAAAAGAAAGAAG | 75 |
| TRAV25 | hTRAV25upn3 | 27 | 154 | TGGACATCCCGTTTTTTTGATACAGTT | 76 |
| TRAV29 (TRDV5) | hTRAV29up | 24 | 267 | AGCAAAATTCACCATCCCTGAGCG | 77 |
| TRAV30 | hTRAV30upn2 | 24 | 139 | TGAAGGGTGGAGAACAGAAGGGTC | 78 |
| TRAV35 | hTRAV35_intup | 27 | 377 | GGCTGGGAAGTTTGGTGATATAGTGTC | 79 |
| TRAV36 (TRDV7) | hTRAV36up1 | 26 | 280 | AGTGAAGACAAGGTGGTACAAAGCCC | 80 |
| TRAV39 | hTRAV39up1 | 26 | 352 | GGGAGGAACAGGATTATTGGGGTAAC | 81 |
| TRAV41 | hTRAV41_intup | 28 | 368 | GCCCTCCTGAAAATGTGTAAAGAAATGT | 82 |
| TRDV1 | hTRDV1up1 | 25 | 259 | CAGTATCCATGCCAGTGAGGAAAGC | 83 |
| TRDV3 | hTRDV3up1 | 24 | 287 | GACAAAGTAACCCAGAGTTCCCCG | 84 |

According to another variant, the invention also makes it possible to analyze the rearrangements of all the J genes of the human IgH locus with at least 2 given genes $V_x$ and $V_y$ of the same locus, by carrying out at least one multi-n-plex PCR with n≥2 (and in particular with n=2), with a combination of primers comprising 2 sense primers which hybridize upstream of and/or in said $V_x$ and $V_y$ genes and one antisense primer which hybridizes downstream of and/or in the IgHJ6 gene, for example the primer hIgHJ6do2 (GATCTTG-CAGTCCTACAGACACCGC, SEQ ID No 85), which hybridizes between base 368 and base 392 starting from the beginning of the IgHJ6 gene.

By way of primers which hybridize upstream of and/or in a V gene of the human IgH locus, that can be used according to this aspect of the invention, mention may be made of the primers defined in the table below:

TABLE 8

| Name of gene | Oligo-nucleotide name | Size (nt) | Distance with the end of the V gene in bp | Sequence | SEQ ID No. |
|---|---|---|---|---|---|
| IgHV1.2, 8, 18, 46, 69 | hIgHV1Aup1 | 25 | 172 | GACAAGGGCTTGAGTGGATGGG | 86 |
| IgHV2 | hIgHV2up1 | 22 | 44 | CATGGACCCTGTGGACACAGCC | 87 |
| IgHV3.7, 13, 15, 20, 21, 23, 48, 53, 64, 66, 72, 73, 74 | hIgHV3Aup1 | 24 | 315 for V3.7 | TGTTTGCAGGTGTCCAGTGTGAGG | 88 |
| IgHV4 | hIgHV4up1 | 25 | 69 | GAACCAGTTCTCCCTGAAGCTGAGC | 89 |
| IgHV5 | hIgHV5up1 | 21 | 55 | TGCAGTGGAGCAGCCTGAAGG | 90 |
| IgHV6 | hIgHV6up1 | 23 | 371 | AGCAGCATTCACAGACTGAGGGG | 91 |

According to one particular implementation of this method, the primers specific for the $V_x$ and $V_y$ genes of the IgH locus are chosen such that the sum of the distance between the 5' end of the region of hybridization of the primer specific for $V_x$ and the end of said $V_x$ gene, and of the distance between the 5' end of the coding sequence of the IgHJ1 gene and the 3' end of the region of hybridization of the hIgHJ antisense primer is greater than the sum of the distance between the 5' end of the region of hybridization of the primer specific for $V_y$ and the end of said $V_y$ gene, and of the distance between the 5' end of the coding sequence of the IgHJ6 gene and the 3' end of the region of hybridization of the hIgHJ6 antisense primer. This enables the amplicon corresponding to $V_x$J6 to be larger than that corresponding to $V_y$J1, so as to have resolution of the amplicons in the order $V_y$J6, $V_y$J5, ..., $V_y$J1, $V_x$J6, ..., $V_x$J1.

However, given the size of the cluster of IgHJ genes, the primers specific for the $V_x$ and $V_y$ genes of the IgH locus will preferably be chosen so as to obtain an "embedded" arrangement of the amplicons, i.e. such that at least one amplicon obtained with a first pair of primers is bordered by 2 amplicons obtained with a second pair of primers.

The method of the invention also makes it possible to analyze the incomplete rearrangements of the human IgH locus, by carrying out at least one multi-n-plex PCR reaction with n≥2, with a combination of at least 3 primers constituting at least 2 pairs of primers comprising a common antisense primer which specifically hybridizes downstream of and/or in a given J gene, such as, for example, the hIgHJ6do2 primer described above, each pair of primers also comprising a sense primer which specifically hybridizes upstream of and/or in a given D gene.

By way of examples of primers which hybridize upstream of and/or in a D gene of the human IgH locus, that can be used according to this aspect of the invention, mention may be made of the primers defined in the table below:

TABLE 9

| Name of gene | Oligo-nucleotide name | Size (bp) | Distance between the 5' end of the primer and the end of the D gene (bp) | Sequence | SEQ ID No. |
|---|---|---|---|---|---|
| hIgHD1 | hIgHD1up1 | 23 | 44 | GATTCTGAACAGCCCCGAGTCAC | 92 |
| hIgHD2 | hIgHD2up1 | 22 | 67 | GGACAGGAGGATTTTGTGGGGG | 93 |
| hIgHD3 | hIgHD3up1 | 20 | 102 | AGGTCAGCCCTGGACATCCC | 94 |
| hIgHD4 | hIgHD4up1 | 19 | 132 | ATCCCCAGGACGCAGCACC | 95 |
| hIgHD5 | hIgHD5up2 | 20 | 85 | AGCTCCTCCTGACAGCCCCG | 96 |
| hIgHD6 | hIgHD6up1 | 21 | 160 | ACACCAGACAGAGGGGCAGGC | 97 |
| hIgHD7 | hIgHD7up2 | 20 | 90 | AGACCGCAGCCACATCAGCC | 98 |

This analysis can in particular be carried out by performing only simple multiplex PCRs, or multi-n-plex PCRs with n≥2, with, in the same reaction, a pair of primers specific for the IgH locus and a pair of primers specific for another locus.

According to one preferred implementation of the invention, the method combines the analysis of the V(D)J rearrangements of the IgH locus and that of the incomplete rearrangements of this locus, by implementing the suitable variants described above. The primers described above for this analysis are suitable for the analysis of the rearrangements of this locus in humans, but this method can be transposed, without any difficulty, to animals, for example to mice.

According to another implementation of the invention, the method is suitable for analyzing the combinatorial diversity of the V(D)J rearrangements of at least two genetic loci chosen from the TRA, TRB, TRG, TRD, IgH, IgK and IgL loci, by combining the suitable variants described above. The analysis of the various loci can be carried out simultaneously or sequentially, by performing, as appropriate, multi-n-plex PCRs with, in the same reaction, at least one pair specific for one locus and another pair specific for another locus.

In particular, the combined analysis of the combinatorial diversity of the V(D)J rearrangements of the TRB locus and of the combinatorial diversity of the VJ rearrangements of the TRG locus or of the TRD locus makes it possible to have a representative view of the repertoire of T lymphocytes. By adding the analysis of the combinatorial diversity of the V(D)J rearrangements of the IgH locus, information on all the lymphocytes (B and T) is obtained.

An important aspect of the invention, illustrated in the examples hereinafter, is the possibility of identifying, by their name, the various rearrangements observed. According to one preferred implementation, step C) of the method comprises a step of processing the data obtained by separating the amplicons according to their size, said processing being carried out by means of a computer and making it possible to assign, to each amplicon observed, the name of the corresponding V(D)J rearrangement. More preferably, the data processing also integrates the intensity of the signal of each of the amplicons observed, in order to quantify the relative frequency of the corresponding V (D) J rearrangement.

This makes it possible to describe a signature of an immune diversity by classifying the VDJ rearrangements in order of intensity or in order of contribution within the immune repertoire observed. This classification of the rearrangements corresponds to a signature of the immune repertoire at an instant "t" in a sample.

In particular, the method of the invention can be such that step B) comprises the acquisition of the data concerning the size of the amplicons and, for each one, the intensity of the signal, and step C) comprises the following steps:
(i) identification of each amplicon, by determining the V(D)J rearrangement to which it corresponds, as a function of its size;
(ii) from the intensity of the signal of each amplicon, determination of the proportion of starting genomic DNA having the corresponding V(D)J rearrangement;
(iii) presentation of the results in the form of a three-dimensional graph showing the $V_x$ genes or the families of $V_x$ genes along one axis, the $J_y$ genes along another axis, and the frequency of the $V_xJ_y$ rearrangements along the third axis.

If the molecular diversity is also measured, for example by carrying out a real-time measurement of the amplifications by multi-n-plex PCR, the method makes it possible to measure an overall immune diversity by taking into account the measurement of the combinatorial diversity and of the molecular diversity.

The present invention also relates to a method for determining, in vitro, the degree of immunodeficiency of an individual, comprising the following steps:
A) using a biological sample from said individual, performing a lymphocyte count;
B) using the same sample or another sample originating from the same individual at the same time, determining the degree of combinatorial diversity of the repertoire of lymphocytes of said individual, by implementing a method as described above;
C) combining the data obtained in steps A) and B).

This method may comprise an additional step of interpreting the combination obtained in step C), from the viewpoint of a graph which assigns a level of risk at least to zones (i) to (iv), and preferably to zones (i) to (vi) hereinafter:
(i) low count (<1000 Ly/µL) and low V-J combinatorial diversity (<40%): high infectious risk, associated with a high risk of mortality;
(ii) low count (<1000 Ly/µL) but normal V-J combinatorial diversity (>65%): low infectious risk;
(iii) normal count (1000-3200 Ly/µL) and low V-J combinatorial diversity (<40%): medium infectious risk;
(iv) normal count (1000-3200 Ly/µL) and normal V-J combinatorial diversity (>65%): the immune repertoire is healthy;
(v) count above normal (>3200 Ly/µl) and low V-J combinatorial diversity (<40%): high lymphoproliferative risk;
(vi) count above normal (>3200 Ly/µl) and normal V-J combinatorial diversity (>65%): medium lymphoproliferative risk.

This determination of the degree of immunodeficiency of an individual (based not only on the count but also on the measurement of lymphocyte diversity) is essential for implementing personalized medicine, since a patient having an immune diversity of less than 40% is considered to have a diversity deficiency which implies an increased risk of mortality by infection. This method therefore makes it possible to determine, for a patient, the risk of mortality of said patient owing to the infection.

Advantageously, the clinician may conduct an immunological follow-up of his or her patient, making it possible in particular to identify whether the treatment administered has consequences that are too severe on the immune diversity of the patient, inducing a risk of mortality owing to infection. In this case, the clinician may adjust the treatment (change of molecule, of dose, of frequency, addition of supplementary antibiotic treatments, of immunostimulation with interleukin IL7, IL2 or the like, etc.) in order to reduce this risk.

The invention therefore also relates to the use of the method above, for aiding a clinician in making his or her therapeutic choices, through the choice of a treatment suitable for the level of risk of infectiousness and of mortality of a patient. Thus, a patient who is in zone (iv) defined above can, a priori, withstand an immunosuppressive treatment (for example, chemotherapy+powerful monoclonal antibodies), whereas, conversely, a patient who is in zone (i) has a very fragile "immune shield" (and therefore a high risk of mortality owing to infection), and should therefore be treated with medicaments that are less immunosuppressive. The patients in zones (ii) and (iii) are in an intermediate situation.

In one preferred implementation of a method for determining, in vitro, the degree of immunodeficiency of an individual, as described above, step B) comprises determining the degree of combinatorial diversity of the repertoire of T lymphocytes and of B lymphocytes of said individual. In this situation, it is advantageously possible to examine the data obtained by means of a three-dimensional graph showing the degree of immunoglobulin diversity on one axis, the degree of TCR diversity on another axis, and the lymphocyte count on a third axis.

Another aspect of the invention concerns a method of monitoring the change in the diversity of the repertoire of T and/or B lymphocytes of an individual, comprising the following steps:

A) measuring the diversity of the repertoire of lymphocytes of said individual, by implementing a method as described above, using two samples from said individual, taken at two different dates;
B) comparing the two samples by evaluating:
(i) the number S of rearrangements observed in the two samples;
(ii) the number A of rearrangements observed in the more recent sample but not in the older sample;
(iii) the number D of rearrangements observed in the older sample but not in the more recent sample;
(iv) the number Z of rearrangements which are not observed in either of the samples.

An example of interpretation of this graph is shown in example 11 hereinafter. This method can also be used to compare 2 samples from different individuals, for example in order to compare a donor and a recipient in the case of a transplant.

The present invention also relates to a kit for implementing one of the methods described above, comprising at least one combination of primers as defined in this text, and reagents for carrying out PCRs.

Among the reagents for carrying out PCRs, a kit according to the invention will preferably comprise a polymerase having the following characteristics:
(i) it is capable of amplifying fragments of several tens of kb;
(ii) its elongation rate is at least 1 kb/minute;
(iii) its robustness is such that it does not introduce more than one error per kb, on average.

Advantageously, a kit of the invention will comprise a multiwell plate in which each well contains a different combination of primers, in freeze-dried form or in a liquid phase. Preferably, this multiwell plate comprises all the combinations of primers necessary for amplifying at least 50%, 60%, 70%, 80% or even 95% of the V-J rearrangements of at least one locus chosen from the TRA, TRB, TRG, TRD and IgH loci.

Another aspect of the invention concerns the use of a method or of a kit as described above, for studying the setting up and/or the quality of the TCR and/or IgH repertoire of a humanized transgenic animal and/or of a culture of lymphocytes. This makes it possible in particular to verify the quality of an immune repertoire subsequent to a cell culture, for example in order to verify that the cell culture remains suitable for testing molecules or for studying biological mechanisms. In the case of monoclonal or oligoclonal T or B lines, this makes it possible to verify that the line(s) is (are) indeed the clone(s) previously identified, and thus to detect any contamination or labeling error on a tube with to run an experiment. Another important application is that of controlling quality during the production of lymphocyte cultures (regulatory T lymphocytes, for example, etc.) before reinjection (for therapeutic purposes).

The present invention also relates to the use of a method or of a kit as described above, for screening for therapeutic molecules in vitro. Examples of applications are described hereinafter.

In particular, the methods and the kits of the invention can be used to carry out a method of evaluating the efficacy of a vaccine protocol, comprising the steps of:
A) measuring the amount and the diversity of lymphocytes before and after said vaccine protocol;
B) comparing the measurements carried out in step A); and
C) interpreting the results, a decrease in lymphocyte diversity of at least 10%, preferably of at least 15%, after vaccination, indicating that the vaccination protocol was effective.

According to one preferred implementation of this method, the amount of regulatory T lymphocytes before and after vaccination is also measured in step A). In this case, interpretation step C also takes into account the change in the number of regulatory T lymphocytes, a decrease by a factor of 2 in the number of regulatory T lymphocytes following the vaccination indicating that the protocol was effective.

The invention also relates to a method for comparing the efficacy of two vaccine protocols, comprising the steps of:
A) measuring, on two groups subjected to a vaccination with two different protocols, the amount of regulatory T lymphocytes and the immune diversity, before and after vaccination;
B) comparing the results group-to-group,
in which the most effective protocol is that which induces the greatest decrease in regulatory T lymphocytes and/or the greatest decrease in lymphocyte diversity.

In addition to the above arrangements, the invention also comprises other arrangements which will emerge from the experimental examples below and from the attached figures.

EXAMPLE 1

Choice of the Position of the Primers that can be Used in the Context of the Invention Oligonucleotide Selection Criteria The primers that can be used for implementing the method of the invention are chosen according to 1) their thermodynamic properties (determined on the basis of algorithms conventionally used by those skilled in the art for identifying the ability of oligonucleotides to bind to their target sequence, in particular according to the number of hydrogen bonds); 2) their compatibility with the other primers used in the same tube, both in thermodynamic terms and in terms of the inability of the various primers to hybridize with one another; and 3) their respective position which makes it possible to obtain amplicon sizes that can be resolved.

The term "resolved" should be understood to mean that the amplicons can be observed individually, subsequent to size-separation thereof by means of an electrophoresis method or any other method. When the sizes of certain amplicons are too close, it is not possible to discern them distinctly with separation conditions that are compatible with the separation for "resolving" all the other amplicon sizes. This case is in the minority and identified. It can be solved, for example, by using labeled primers.

The oligonucleotides are defined herein by giving, in addition to their sequence, their position in the locus and also their size, in number of bases.

For the V genes, the oligonucleotides are oriented in the direction of transcription, they are called "SENSE"; they are complementary to the noncoding DNA strand.

For the J genes, the oligonucleotides are called "ANTI-SENSE"; they are complementary to the coding DNA strand and reverse (they are also referred to as being in the 3'→5' direction).

Primers Specific for V Genes

For the oligonucleotides specific for the V genes, the position is given according to the end of the V gene, i.e. the last base before the RSS. This position corresponds to the distance (including the oligonucleotide) between the $1^{st}$ base of the oligonucleotide and the last base of the V gene.

Example of position of the oligonucleotide for the TRBV gene family: if the distance is n bases from the end of the V gene and the size of the oligonucleotide is t bases, the oligonucleotide begins n bases upstream of the end of the gene (counting the last base) and ends n−t+1 bases from the end of the V gene.

The oligonucleotides were selected in such a way as to hybridize with the largest possible number of members of a V family. Two situations can be described concerning the number of V oligonucleotides necessary for monitoring an entire V family:

Case 1: existence of a region of 100% homology between all the members of a family. In this case, it is possible to find, by performing a sequence alignment, a region 100% common for all the members of the V family in question and meeting the oligonucleotide selection criteria specified above. In this case, only one V oligonucleotide is necessary for monitoring all the members of the family.

Case 2: a region of less than 100% homology. In this case, the largest region (in terms of number of bases) which meets the selection criteria is selected, and all the oligonucleotides corresponding to this position that are necessary for monitoring all the members of the family are designed. Example: for a family of 5 members having a region of 100% homology for 3 members, the other 2 members being different from one another in this region. In this case, a total of 3 different oligonucleotides corresponding to the same position are designed for monitoring all the members of this family. Three subcases are then possible:

The V oligonucleotides chosen at this position are thermodynamically compatible with one another. In this case the n V oligonucleotides (in the example above, 3 oligonucleotides) are grouped together in the same PCR tube. Since all these oligonucleotides, even if they have a few different bases, are designed at the same position, the amplicons will be of the same size.

The V oligonucleotides are not sufficiently thermodynamically compatible and they cannot be placed in the same PCR reaction since this would pose dimer problems. In this case, 2 or n PCRs can be carried out in different tubes, in order to specifically monitor the V members for which the primers are incompatible with the others.

A particular (rare) case exists in which the V genes of the same family do not have the same size. This is due to the fact that the intron of one or n member(s) of a V family has (have) a size that is different than that of the other members of said V family (observation: there is only one intron per V gene). This situation is not a problem if the V oligonucleotide is designed downstream of this "region of different size". If this is not possible, the solution implemented consists in separating the 2 or n oligonucleotides in 2 or n PCRs.

Primers Specific for J Genes

The position of a primer specific for a J gene is given by indicating its distance relative to the start of the J gene i.e. the $1^{st}$ base of the segment of J gene (coding sequence), after the RSS. This position is located downstream of the start of J and corresponds to the distance (including the oligonucleotide) between the $1^{st}$ base of the J gene and the $1^{st}$ base of the oligonucleotide (i.e. the base at the 5' end of the primer).

Example of position of the oligonucleotide for the TRBJx gene family: the distance is n bases from the start of J, the size of the oligonucleotide is t bases. Therefore, the region of hybridization of the primer (on the coding strand) ends at the $n^{th}$ base of the J gene or downstream of the start of the J gene and starts n−t+1 bases from the start of J.

Recovery of the Sequences of the TCR and Ig Loci

Several methods are possible for obtaining the sequences. Two possibilities are described hereinafter.

1st Possibility

The $1^{st}$ possibility requires logging on to the European internet site "Ensembl Genome Browser" http://www.ensembl.org and researching the locus of interest: after having chosen the species (human, mouse, etc.), it is necessary to click on the chromosome of interest, for example chromosome 14 for the TRA locus. It is then necessary to indicate, in the block provided for this purpose, the number indicating the start of the chromosomal region (for example: 21158000) and the end of the region (for example: 22125000). The Ensembl database reveals graphically the arrangement of the TCR and Ig genes present in the locus, and those skilled in the art can export (by means of a left click on the contig concerned) the DNA sequence to the EMBL or GenBANK format with all the corresponding gene annotations. They thus have at their disposal the location of all the sequences of the TCR and Ig genes, including the sequences upstream and downstream of the latter.

The chromosomal regions for the various human loci to which the present invention relates are indicated hereinafter.

*Homo sapiens* TRA/TRD: locus at 14q11.2:
http://www.ensembl.org/Homo sapiens/contigview?region=1 4&vc start=21158000&vc end=22125000

*Homo sapiens* TRB: locus at 7q34:
http://www.ensembl.org/Homo sapiens/contigview?region=7 &vc start=141640000&vc end=142275000

*Homo sapiens* TRG: locus at 7p14:
http://www.ensembl.org/Homo sapiens/contigview?region=7 &vc start=3824200&vc end=38385000

*Homo sapiens* IgH: locus at 14q32.33:
IgHV:
http://www.ensembl.org/Homo sapiens/contigview?region=1 4&vc start=105476000&vc end=106368585
IgHD and IgHJ:
http://www.ensembl.org/Homo sapiens/contigview?region=1 4&vc start=105400000&vc end=105460000
IgHC:
http://www.ensembl.org/Homo sapiens/contigview?region=1 4&vc start=105120000&vc end=105400000

*Homo sapiens* IgK: locus at 2p11.2:
IgKV (proximal cluster), IgKJ and IgKC:
http://www.ensembl.org/Homo sapiens/contigview?region=2 &vc start=88920000&vc end=89480000
IgKV (duplicated digital cluster):
http://www.ensembl.org/Homo sapiens/contigview?region=2 &vc start=89550000&vc end=89950000

*Homo sapiens* IgL: locus at 22q11.2:
http://www.ensembl.org/Homo sapiens/contigview?region=2 2&vc start=20700000&vc end=21650000.

2nd Possibility:

The $2^{nd}$ possibility presented hereinafter requires the grouping together of all the cosmids containing the sequences of a TCR or Ig locus. To do this, we identified the list of accession numbers of the cosmids for the Ig and TCR chains, in humans and mice, using the literature as a basis (Lefrancs, The Immunoglobulin Facts Book 2001 and Lefrancs The T cell receptor Facts Book 2001) or else (Baum et al., 2006; Baum et al., 2004).

TABLE 10

| Locus | EMBL-EBI accession number |
|---|---|
| Human | |
| TRAD* | AE000658 to AE000662 |
| TRB | L36092 |
| TRG | AF159056, X08084, M12950, M12960, M16016 and M12961 |
| IgH | see Lefranc., The Immunoglobulin Facts Book ISBN: 012441351X |
| MOUSE | |
| TRAD* | AE008683 to AE008686 |
| TRB | AE00063 to AE00065 |
| TRG | AF037352 and AF021335 |
| IgH | see Lefranc., The Immunoglobulin Facts Book ISBN: 012441351X |

*Reminder: the TRD locus is located in the TRA locus.

From these numbers, it is possible to recover all the information on the source sequences of the loci in the "EMBL-EBI" European reference internet site (http://www.ebi.ac.uk), by carrying out a "search", in the "nucleotide sequence" section. The "EMBL-BANK" (Europe's primary nucleotide sequence resource) results can subsequently be downloaded to the EMBL format.

The study of the sequences can be carried out on software such as NTI Vector®. Since the genes are annotated, their position is precisely indicated.

Correspondence Between the Various Nomenclatures of the Genes of the TCR and Ig Loci It is important to note that the nomenclature of the genes has changed over time. In order for those skilled in the art to find their way around the nomenclatures, they have correspondence tables for the TCRs and Igs that can be found in the two books [1] Lefranc, M.-P. and Lefranc, G., The Immunoglobulin Facts Book, Academic Press, 458 pages (2001) ISBN:012441351X [2] Lefranc, M.-P. and Lefranc, G., The T cell receptor Facts Book, Academic Press, 398 pages (2001) ISBN:0124413528. This information can also be found on the IMGT site (http://imgt.cines.fr).

EXAMPLE 2

Protocol for the Use of ImmunTraCkeR Kit

Example on the TRB Locus

The amounts necessary are optimized according to the nature of the sample (cells; PBMCs; thymus extract; etc.). For a cell sample, the amount necessary for carrying out the experiment is $10^6$ cells.

The succession of the various steps of the protocol is shown schematically in FIG. 19.

2-A. DNA Extraction

An extracted DNA of high purity is necessary for detecting the V-J rearrangements using the ImmunTraCkeR Kit. Those skilled in the art know which method or kit is suitable for this. In particular, those skilled in the art know that this extraction should be carried out without any EDTA or other product that may inhibit the PCR. The inventors recommend extracting the DNA using the High Pure PCR Preparation Template Kit from Roche®.

The recommended DNA concentration is 100 ng/µl.

2-B. Control of DNA Quality and Determination of the Amount

The absorbance of the sample at 260 nm is measured with a spectrophotometer (for example, Amersham GenQuant Pro). This measurement makes it possible to calculate the DNA concentration, the degree of extraction and the DNA/protein ratio, which gives an estimation of the quality of the DNA.

In addition, the degradation state of the DNA is controlled on an agarose gel and, subsequently, the DNA concentration is standardized by comparison with an actin control.

2-C. PCR Amplification

The ImmunTraCkeR Kit contains the combinations of primers (dehydrated or in liquid phase) already distributed into the tubes. The reaction mixture is prepared and distributed into said reaction tubes.

a) Herculase® II Fusion Optimized Protocol

Preparation of the Reaction Mixture

TABLE 13

| Component | Amount per reaction |
|---|---|
| Distilled water | 12.89 µl |
| Herculase ® II 5X reaction buffer | 5 µl |
| dNTP mix (10 mM) | 0.62 µl |
| DNA template (50 ng/µl) | 1 µl |
| Herculase ® II Fusion DNA polymerase | 0.5 µl |
| | Final volume: 20 µl |

The reaction mixture is then distributed into tubes or wells, in a proportion of 20 µl in each.

The PCR is carried out using optimized cyclic conditions. Suggested cycling parameters for carrying out PCRs with the Herculase® II Fusion DNA polymerase, using a Primus 96+ (MWG) device, are indicated below.

PCR Cyclic Parameters:

TABLE 14

| Segment | Number of cycles | Temperature | Duration |
|---|---|---|---|
| 1 | 1 | 98° C. | 3 minutes |
| 2 | 30 | 98° C. | 20 seconds |
| | | 62° C. | 20 seconds |
| | | 72° C. | 3 minutes 30 seconds |
| 3 | 1 | 72° C. | 3 minutes |

Duration of PCR: approximately 4.5 hours.

2-D. Agarose Gel Electrophoresis

A 0.8% (w/v) agarose gel is prepared in a 1×TBE buffer.

The PCR products, mixed beforehand with a loading buffer (0.25% bromophenol blue, 0.25% xylene cyanol FF, 30% Ficoll 400, in water), are loaded in a proportion of approximately 10 µl of PCR products and 2 µl of loading buffer.

A suitable DNA size marker is loaded onto each end of the gel.

A voltage is applied to the gel in a 1×TBE buffer, without recirculation of the buffer, for 1 hour 30 minutes at 250V and 120 mA.

The gel is stained with 40 µl of ethidium bromide diluted in 150 ml of 1×TBE buffer for 30 minutes.

2-E. Acquisition and Interpretation

The gel is placed on a UV transilluminator and the image is acquired by photography. The presence or the absence of the specific products of the PCR is recorded.

EXAMPLE 3

Analysis of the Rearrangements of all the Functional J Genes of the Beta Locus with One Given V Gene, in One Resolving Multi-2-Plex PCR FIG. 2a shows the analysis of the average GC content of the human TRBJ and TRAJ regions. The J2 region contains a very high GC content, with 60% against 40-45% on average.

FIG. 2b shows the particular arrangement of the J genes of the TRB locus (in 2 distinct clusters).

FIG. 2c illustrates the principle for choosing the primers, with one antisense primer close to a J cluster and a second antisense primer far from the J cluster, making it possible to position the entire J1 cluster above the J2 cluster.

FIG. 2d presents an example of a result obtained by means of this method.

This configuration makes it possible to halve the amount of biological material necessary and by the same token to reduce the cost price of the test. The amount of time for carrying out the test is also reduced. In addition, this enables a simplified reading of the lane of the gel (or of another type of separation) since the J genes are in the order of the locus and are therefore readily identifiable.

EXAMPLE 4

Analysis of Several Loci in the Same Multi-n-Plex PCR Reaction

Figure 1A:
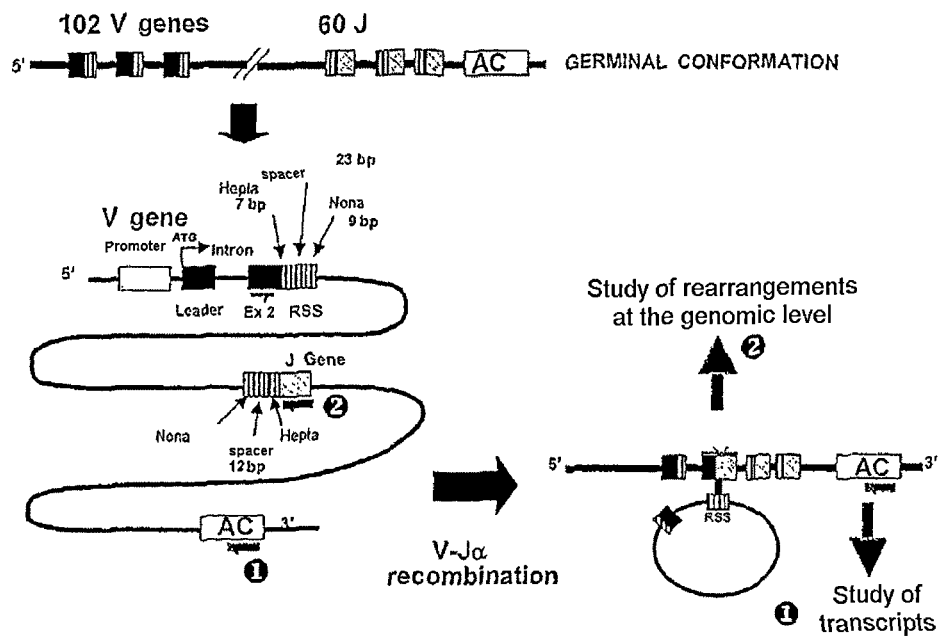
Figure 1B:
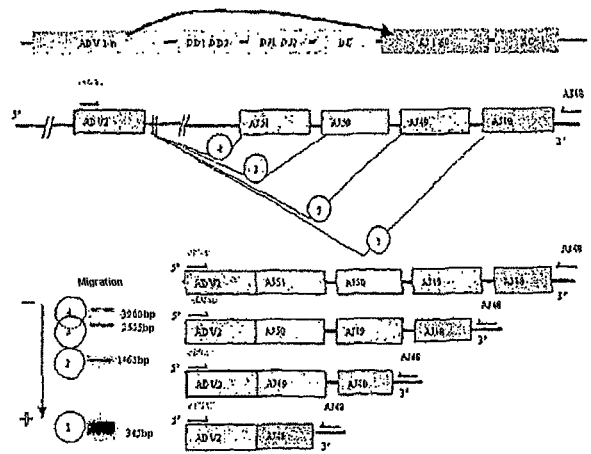
Figure 3:
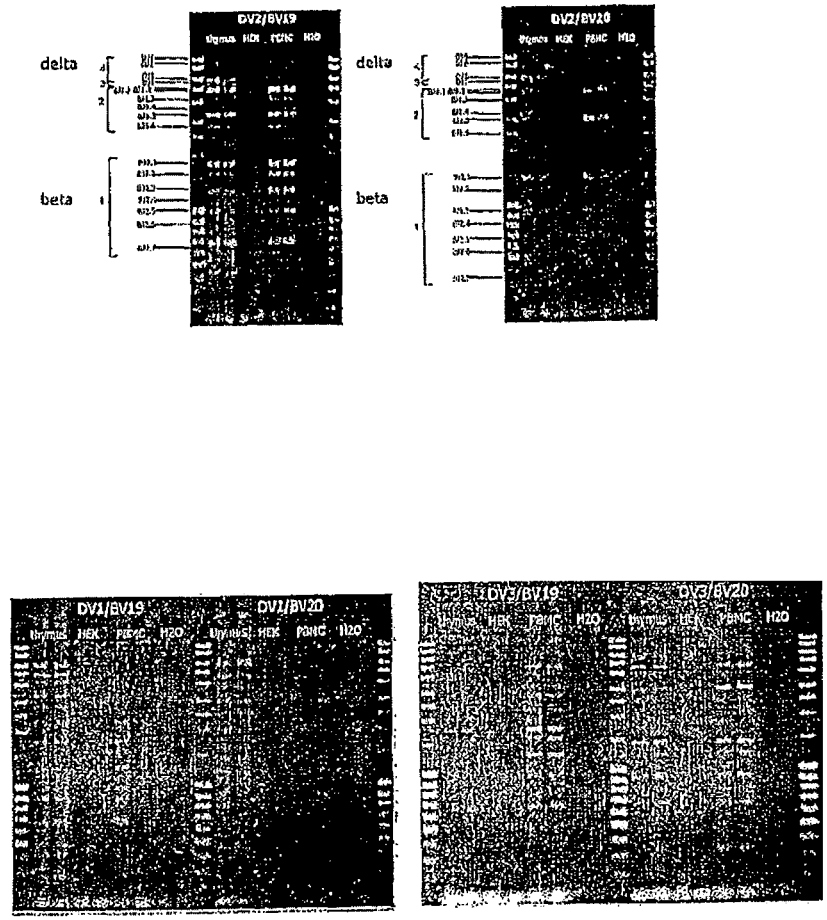

FIG. 3 illustrates the possibility of analyzing rearrangements of several loci in the same reaction, so as to reduce, by a factor of 3-4, the amount of biological material necessary for monitoring the entire immune repertoire. In this example, rearrangements of the TCRB and TCRD repertoires are observed in a single step. This makes it possible to monitor all the T alpha/beta and T gamma/delta lymphocytes.

EXAMPLE 5

Embedded Multiplex PCR

FIG. 4 illustrates the principle of "embedded" multi-n-plex PCR, i.e. in which the series of amplicons obtained with the various pairs of primers are such that an amplicon obtained with a first pair of primers can be bordered by 2 amplicons obtained with a second pair of primers.

Figure 4A:
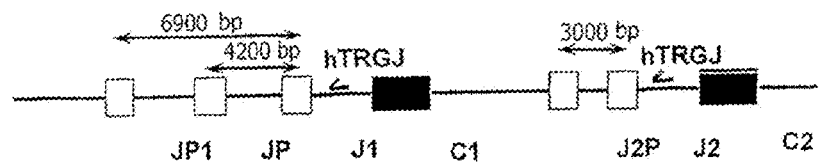

FIG. 4a gives a diagram of the TRG locus.

Figure 4B:
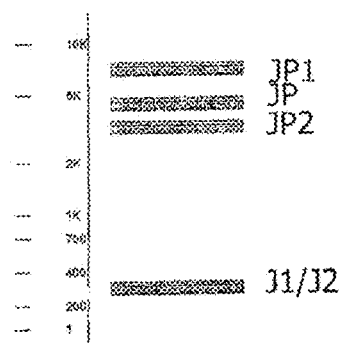

FIG. 4b shows diagrammatically the principle of resolution with an hTRGV family.

Figure 4C:
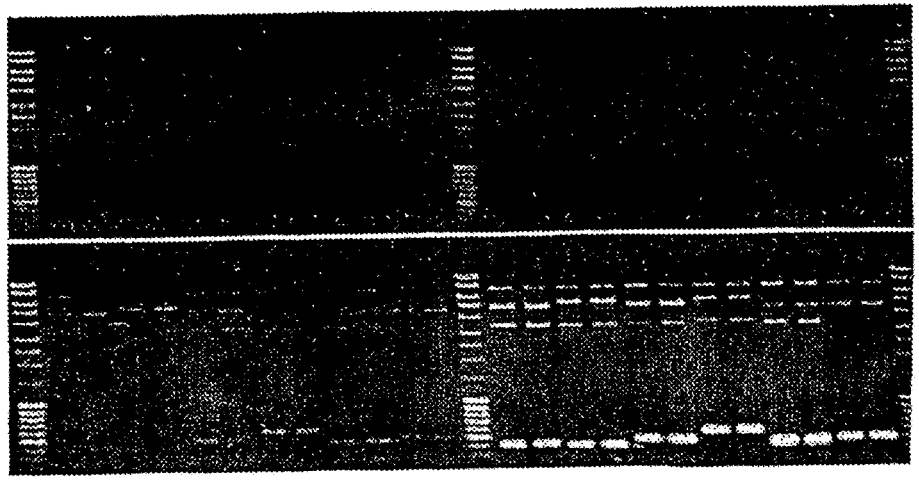

FIG. 4c shows the result of a multiplex PCR on the hTRG locus, targeting the 2 J clusters with a single J primer. The experiment was carried out on HEK and CaCO cells as negative controls and on PBMCs and thymus cells as positive controls.

It should be noted that, for the TRG locus, it is possible to monitor 2 TRGJ clusters with just one J oligonucleotide, owing to the 100% sequence homology downstream of the J1 and J2 genes.

Figure 4D:
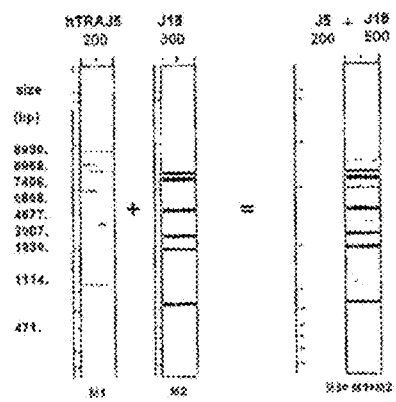

FIG. 4d shows an example of embedded multi-2-plex PCR with two TRAJ primers.

Figure 4E:
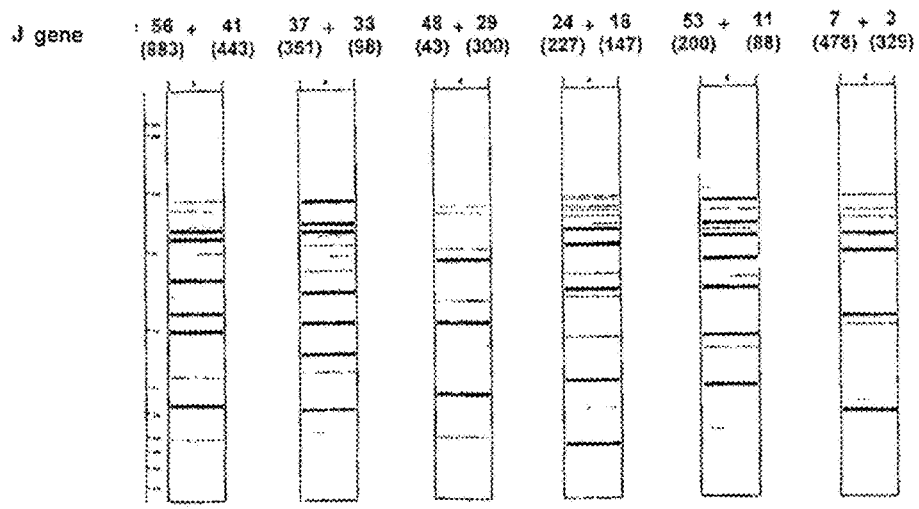

FIG. 4e shows an example of resolution of 95% of the AJ region with only 6 multi-2-plex PCRs. The position of the primers is indicated below the name of the J gene of the oligonucleotides downstream of the (start of the) J gene. This position is important. It makes it possible to be sure that the expected bands will have a size that allows them to be resolved.

EXAMPLE 6

Result of the TRBV ImmunTraCkeR Kit in Multi-2-Plex PCR

Figure 5:
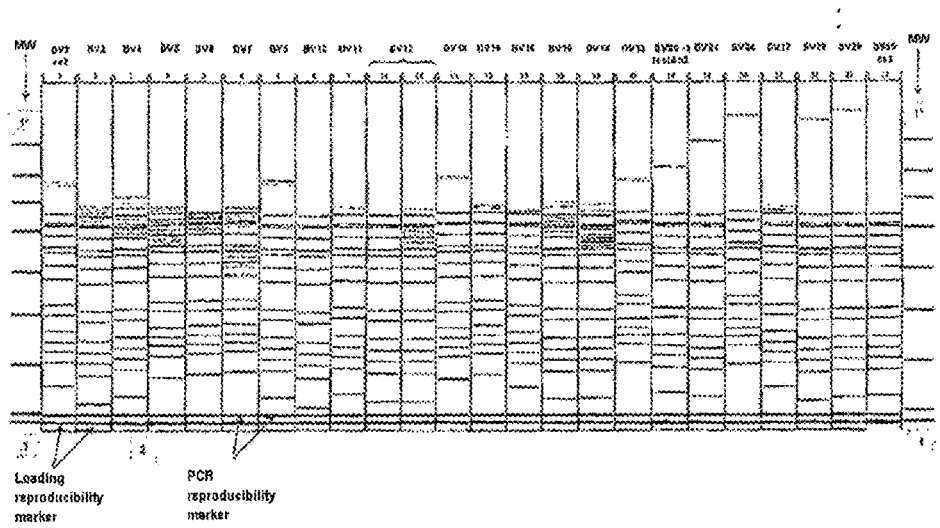
Figure 6:
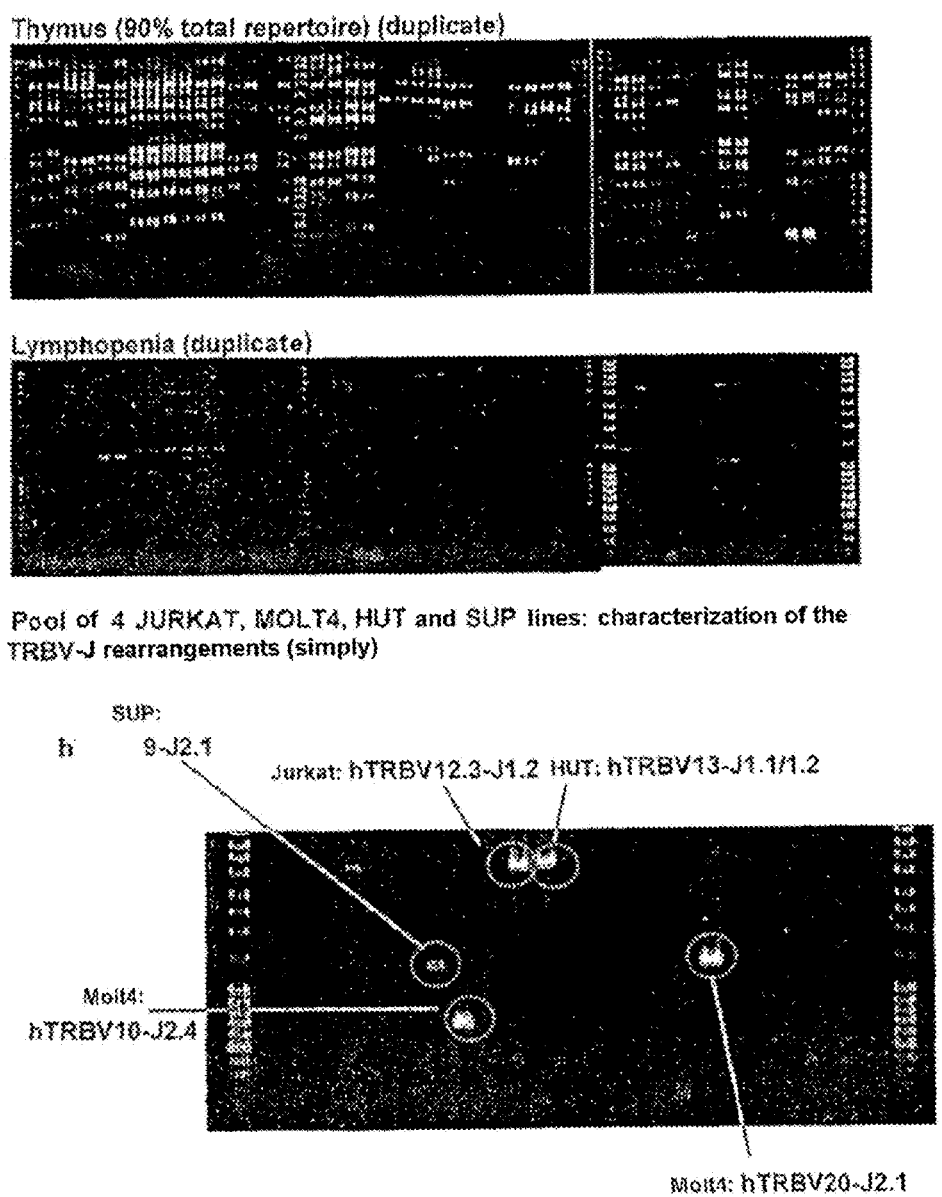

FIGS. 5 and 6 show the various bands obtained after the migration, on an agarose gel, of all the PCR products obtained by multi-n-plex PCR. FIG. 5 shows a diagrammatic representation of the theoretical result obtained with the human TRB ImmunTraCkeR kit (the representation is similar in other species: rat, mouse, monkey, etc.). Each column corresponds to one TRBV family, each band corresponds to a given V-J rearrangement. The TRBV genes were studied in the following order: BV2, BV3, BV4, BV5, BV6, BV7, BV9, BV10, BV11, BV12, BV13, BV14, BV15, BV16, BV18, BV19, BV20, BV24, BV25, BV27, BV28, BV29, BV30. FIG. 6 shows the corresponding experimental results obtained in duplicate (loaded side by side) with three types of samples: gDNA extracted from thymus, gDNA extracted from PBMCs under lymphopenic conditions and, finally, a pool of DNA of 4 T lines each comprising one or two TRBV-J rearrangements.

Having all the PCRs of the 24 TRBVs side by side allows exhaustive detection of the TRBV genes over all the BJ segments.

It is also possible to add (as an option) a loading and/or PCR reproducibility marker to each of the lanes (observation: these 2 reproducibility markers are not essential). Advantage sought: improving the standardization of the signal between the bands.

This figure illustrates the fact that the invention makes it possible to evaluate the quality of an immune repertoire by measuring both the combinatorial diversity of an image of the immune repertoire (calculation of the sum of the bands obtained) and also the intensity of the signal of all of the bands (calculation of the sum of all the signals of the amplicons of the image). In addition, the name of each V(D)J rearrangement present or absent is identified (as a function of its position in the image). The column gives the name of the V; the size of the amplicon gives the name of the J. The intensity of the signal detected gives the respective proportion of each V(D)J rearrangement. Overall, this therefore makes it possible, in a single step, to have a tool which both measures the diversity (useful for measuring the precise degree of immunodeficiency of a patient) and identifies the name of the rearrangements (therefore the TCR or Ig marker of a lymphocyte) involved in a pathological condition (leukemia, lymphoma, GVHD, etc.) or having reacted by increasing (cell multiplication) or by decreasing following a treatment.

EXAMPLE 7

Study of D-J Rearrangements by PCR Clustering

Figure 7:
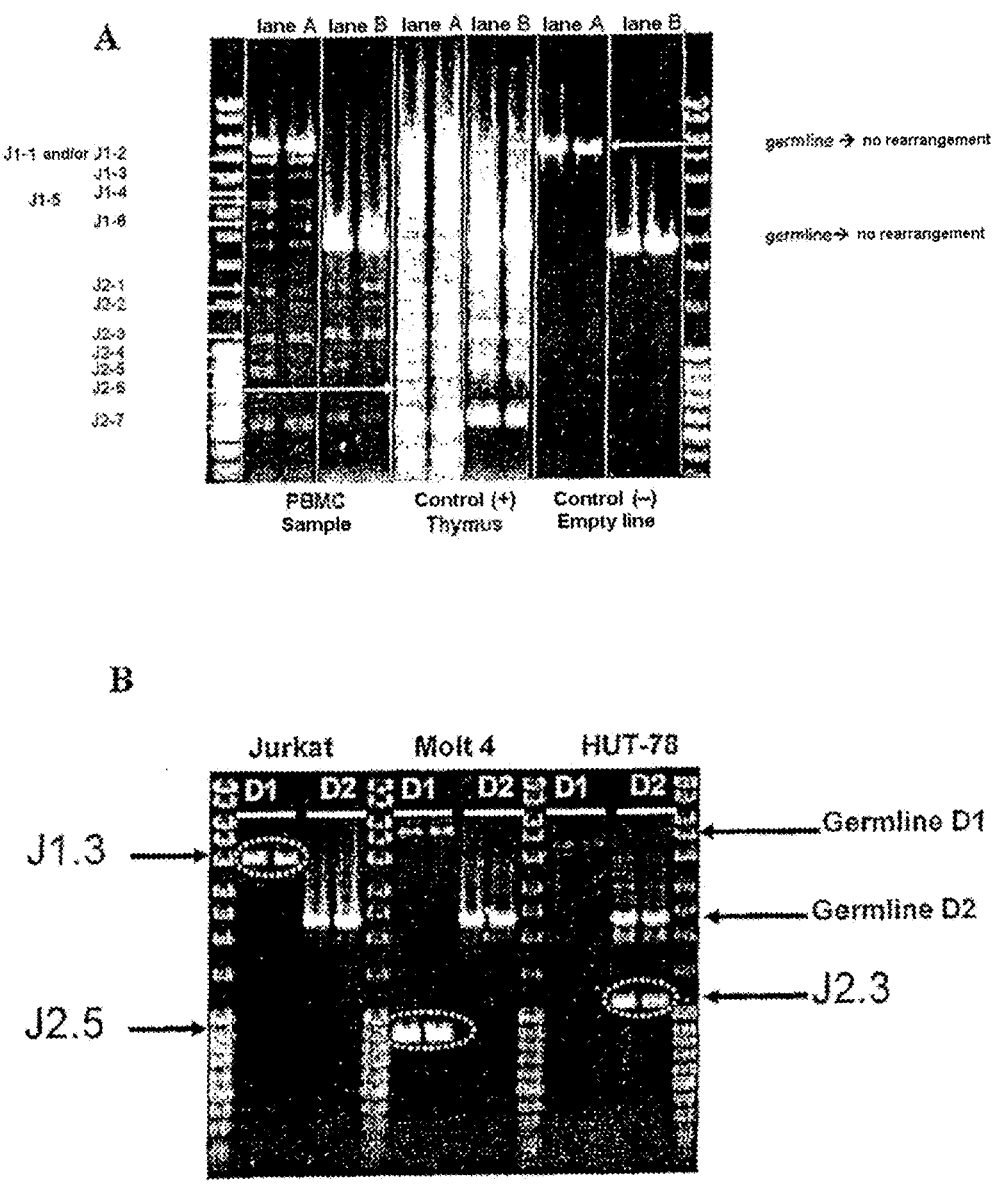

FIG. 7 shows the result of a test for detecting incomplete D-Jβ rearrangements which is both exhaustive and resolvent (lanes A: D1 rearrangements with the J1 cluster and the J2 cluster. Lanes B: D2 rearrangements with the J2 cluster). This test makes it possible to characterize a clone by specifying the name of the rearranged D and J genes.

In comparison, Biomed-2 proposes only a signal of ON/OFF type: the presence of a monoclonal population is actually detected, but this population is not characterized at the combinatorial level. It is not possible to differentiate between the rearranged V and J genes. This is because the size of the PCR products of this test varies only by a few bases, making it impossible to identify the V family in question, or the rearranged J gene. The method of the present invention therefore makes it possible to provide a higher degree of information.

Analysis of the Results:

Part A: The number of expected bands is clearly observed on positive controls (PBMCs and thymus). The bands corresponding to the rearrangements of the D1 gene with the J1.1 and J1.2 genes are fused since the resolvent limits of the technology used do not allow the separation of bands of which the size difference does not exceed 10% of the size of the largest band. Sequencing of this band, or the use of labeled primers, would be necessary for validation of this observation.

Two very strong bands appear on the negative control. These bands are not nonspecific, but correspond to the germinal DNA amplification: the characteristics of the locus coupled with the ability of the technology to amplify large fragments mean that it is not necessary for there to be a rearrangement in order to observe a product in this precise case. These two bands constitute a very good internal control for the presence and for the quality of the DNA tested, and also for the efficiency of the enzyme.

Part B: The method makes it possible to very rapidly characterize the intermediate rearrangement of T (or even B) lymphocyte lines. In the example above, the incomplete D1-J1.3 rearrangement for the T cell line called JURKAT, the incomplete D1-J2.5 rearrangement for the MOLT4 T line and the incomplete D2-J2.3 rearrangement for the HUT-78 T line were characterized without the need for further sequencing.

It is important to note that the incomplete D-J and D1-D2 rearrangements are nonfunctional, but, in certain cases, represent the only biological marker for identifying lymphoproliferation (B or T lymphoma or leukemia).

EXAMPLE 8

Examples of Representation of the Results of Mapping

Figure 8:
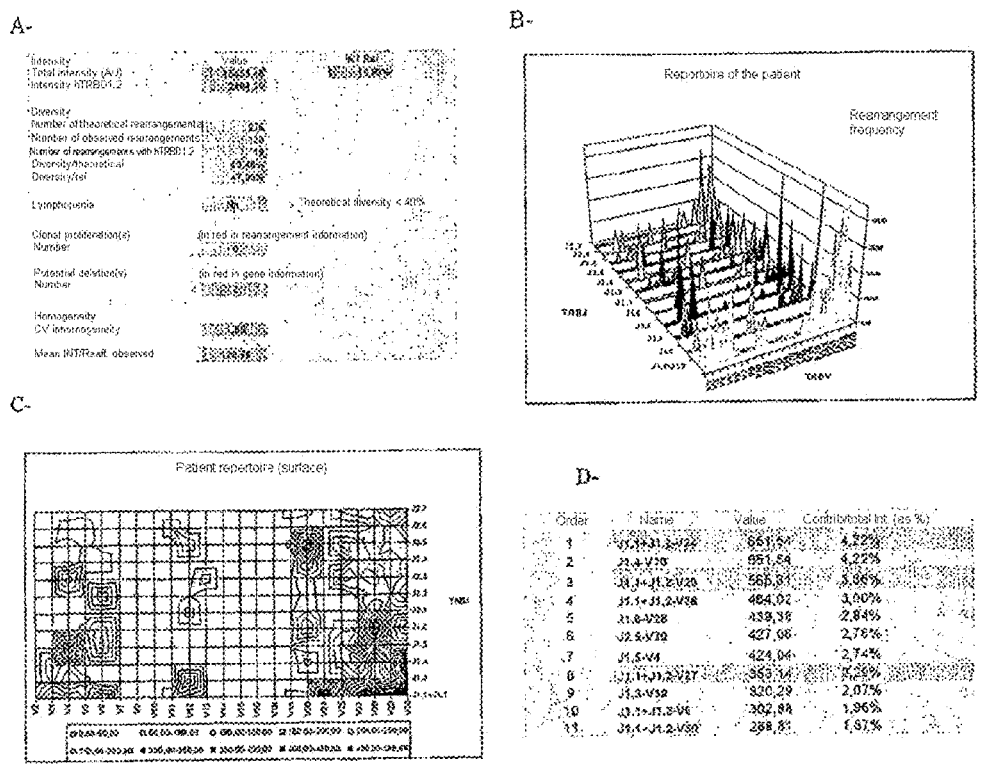

FIG. 8 illustrates a method for grouping together all the data from analysis of the immune repertoire on a single page, including in particular the count, and/or the diversity of the sample, and/or the intensity of the signal, and/or a comparison with a reference diversity originating from another patient or from the same patient, information for identifying that the patient is suffering from lymphopenia by comparing the % diversity obtained with a reference repertoire, and/or information on the number of clones detected in the image, and/or a two-dimensional and/or three-dimensional representation graphic, and/or the list of all the V-J rearrangements classified by a decreasing amount of amount of signal detected, and/or % representativeness in the image. The method, in its steps of analysis, thus makes it possible:

1—to compile the information collected regarding the clinical history of the patient and the biological history of the sample (results of counts, cytometries, sampling conditions, etc.);
2—to comb the data using statistical methods and to correlate the results of analyses of the immune repertoire (combinatorial diversity, or other approach) with the clinical and biological data. It is in particular possible to classify all the V(D)J rearrangements in order of frequency of detection (intensity of the signal of the amplicon). This order varies from one individual to the other according to the treatments and infections encountered by the lymphocyte repertoire of said individual. This makes it possible to possess the signature of the immune repertoire of an individual at an instant T. This signature may be the biological marker for a pathological condition, such as autoimmune diseases, allergies, leukemias, lymphomas, etc.

N.B.: It is important to note that this approach can also be compatible with other approaches for analyzing the immune repertoire (all approaches for analyzing the junctional diversity, pairing diversity, somaticmutation diversity, etc.).

EXAMPLE 9

Lympocyte Count/Diversity (LCD)

Figure 9:
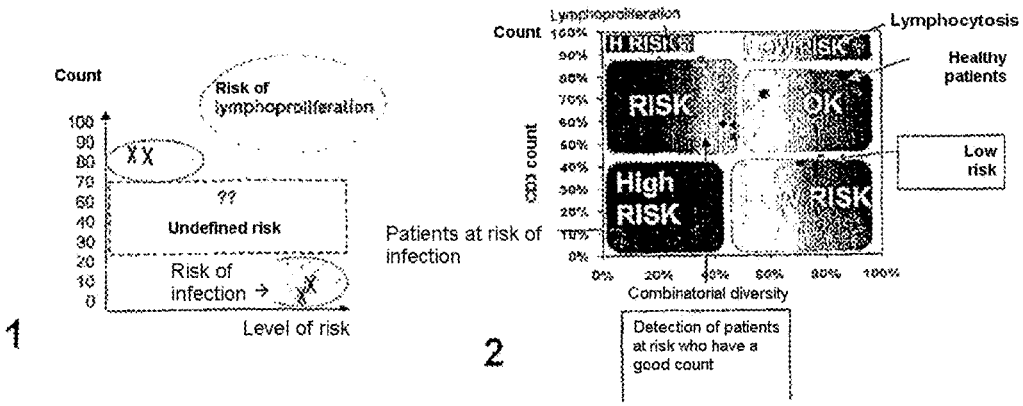

The lymphocyte count performed during a CBC or during labeling in cytrometry gives the number of lymphocytes in a sample. This number is used to verify that the patient does not show any immunodeficiency. The range of "normality" is conventionally between 1000 and 3200 lymphocytes/µL of blood. Below 1000, the patient is considered to be slightly immunodepressed; below 450, severe immunosuppression is involved. Conversely, above 3200, the patient is considered to be potentially at risk of lymphocyte expansion. There are two weak points in this approach: the first is the size of the range itself, which corresponds to a factor of 3 between the minimum and maximum values. The second point, which is even more bothersome, is that this count does not prefigure the real diversity of the immune repertoire of the patient (FIG. 9, graph 1). The present invention makes it possible to couple a conventional count with a measurement of the V-J combinatorial diversity (FIG. 9, graph 2).

This can in particular be used for selecting patients in the context of clinical trials, in order to test medicaments on a homogeneous population, making it possible to interpret the results. This also makes it possible to give a prognosis of a patient's infectious risk, and therefore to practice personalized medicine, by adjusting the immunosuppressiveness of a treatment to a patient's level of risk of mortality owing to infection.

The graph in FIG. 9 distinguishes in particular the following populations:

1. Low count (<1000 Ly/µL) and low combinatorial diversity (<40%): The patient is an immunosuppressed patient.
   Action to be taken: Do not include this patient in the clinical study. Have this patient monitored by a hematologist.
2. Low count (<1000 Ly/µL) but normal V-J combinatorial diversity (>65%): the patient has a low level of circulating lymphocytes compared with the other populations of immune cells, but the quality of said patient's specific immune defense is not especially called into question.
   Action to be taken: If the study is a study concerning elderly individuals, it would be interesting to include an arm of patients having this characteristic.
3. Normal count (1000-3200 Ly/µL) and low combinatorial diversity (<40%): there are "gaps" in the immune repertoire. This lymphocyte count, which appears to be normal, hides an immunodeficiency condition that may be associated with one or more clonal expansions. The vaccine efficacy may be called into question.
   Action to be taken: We recommend not including this patient in the clinical study. Have this patient monitored by an oncologist-hematologist.

4. Normal count (1000-3200 Ly/μL) and normal diversity (>65%): the immune repertoire is healthy.

Action to be taken: The patient can be included in the clinical study.

5. Count above normal, and low diversity: high-risk zone, the sample contains only one or a few clones of lymphocytes.

Action to be taken: Do not include this patient in the clinical study. Have this patient monitored by an oncologist-hematologist.

6. Count above normal, but normal diversity: generalized lymphocytosis, the individual's specific immune system is overactivated, but no element implies a monoclonal expansion that may be connected to a leukemia or a lymphoma.

Action to be taken: Do not include this patient in the clinical study. Have this patient monitored by an oncologist-hematologist in order to monitor the progression of the lymphocytosis.

This novel count technique, called "lympocyte count/diversity", which couples the analysis of the immune repertoire with the count (whatever the counting method) of the number of lymphocytes of the patient, is therefore much more informative than the simple lymphocyte count. It makes it possible in particular to avoid the paradox of the cell count which at times gives the impression that a patient has a lymphocyte number considered to be normal, but who, in reality, exhibits T or B clones and therefore a low immune diversity (zone 3). Conversely, this makes it possible to be sure that patients having a low count nevertheless have a "correct" immune diversity (zone 2) enabling them to defend themselves against infections and therefore making it possible not to impose on them medical monitoring that is as laborious as for patients who are really immunodepressed, i.e. patients with a low count and a low diversity (zone 1). In addition, this makes it possible to distinguish between at least 2 categories of patients having a very high lymphocyte count. The first category (zone 5) has a low diversity which is associated with the presence of one or more clones, that may be due to a leukemia, a lymphoma, GVHD, an autoimmune disease, an allergy, a response to a vaccine or any other therapy and immunotherapy. The $2^{nd}$ category (zone 6) corresponds to a lymphocytosis, i.e. an expansion of the majority of the immune repertoire.

EXAMPLE 10

Strategy for Personalized Diagnosis in Oncology-Hematology

Figure 10:
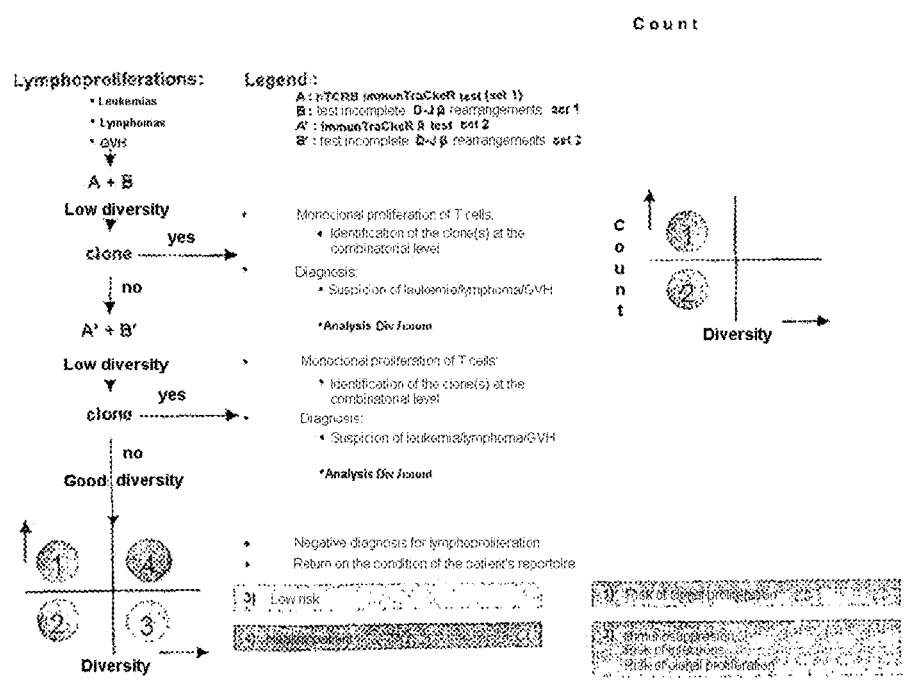

FIG. 10 presents a decision tree in oncology-hematology using LCD.

According to the scheme presented, two sets of primers are used sequentially (the test with the $2^{nd}$ set being optional) to detect the VJ and DJ rearrangements of the TRB. The primers of the $2^{nd}$ set are shifted compared with those of the $1^{st}$ set, in order to avoid allowing a clone to escape because of a polymorphism having appeared at the site of hybridization of the corresponding primer, or of a somatic hypermutation, etc.

This procedure makes it possible to perform a diagnosis with respect to the level of risk of lymphoproliferation and, at the same time, the level of risk of immunodeficiency (to be associated with the risk of infection).

EXAMPLE 11

Comparison of the Lymphocyte Diversity of Two Samples

Figure 11:
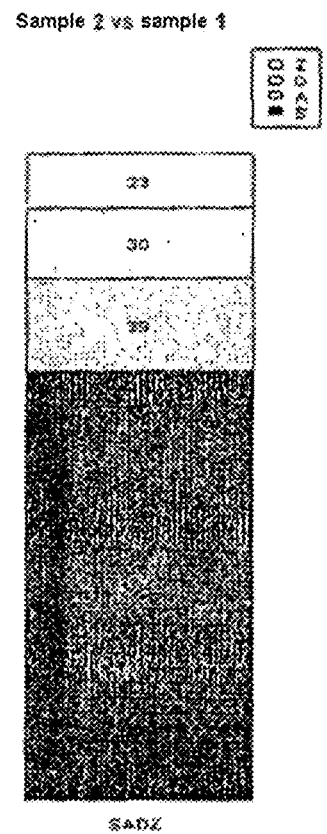
Figure 11:
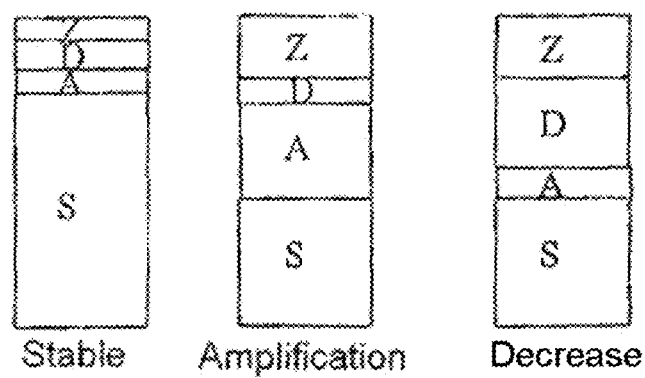

FIG. 11 shows a graph which makes it possible to compare two immune repertoires in order to identify the similarities or differences that may exist. Given below are the order of reading and the description of each component, and also a concrete example of the interpretation of the results.

The region S for "stable" represents the number of rearrangements observed in the two samples. The zone A for "appeared" represents the number of rearrangements observed in sample 2 but not in sample 1. The zone D for "disappeared" represents the number of rearrangements which are observed in sample 1 but not in sample 2. Finally, the zone Z for "never seen" represents the number of rearrangements which are observed neither in sample 1 nor in sample 2.

Interpretation: the high number of rearrangements observed in common (184) in the two samples indicates that the two repertoires appear to be identical.

Representing, on one graph, the sum of the appearances, amplification A, disappearance D, the nondetection Z and the detection S (for stable) of all the rearrangements between two immune mappings makes it possible, in one step and very visually, to determine whether a patient is undergoing reconstitution (there will be a lot of A and a low D) or whether said patient is becoming oriented toward an immunodeficiency phase (there will be a lot of D and a low A), or, finally, whether the repertoire is stable between the two mappings (there will be a lot of S).

Moreover, the method described here makes it possible, by relating the number of rearrangements that have appeared or disappeared to the time elapsed between the taking of the two samples, to obtain an indication regarding the speed of reconstitution or of reduction of a repertoire. This makes it possible in particular to compare the stimulant effect or, conversely, the immunosuppressive effect of a treatment.

EXAMPLE 12

Early Detection of (Oligo)Clonal Lymphoproliferation By Quantitative Multi-n-Plex PCR FIG. 12 shows diagrammatically a particular embodiment of the methods of the invention, in which the multi-n-plex PCRs are monitored in real time, in order to detect the presence of lymphoproliferation before any (optional) step of separating the amplicons by electrophoresis.

The PCR amplification is carried out in a real-time quantitative PCR machine, using, for example, the protocol described in example 2 above, with in addition a fluorescence measurement being carried out at each amplification cycle.

A specific reaction mixture, compatible both with the quantitative PCR and with the multi-n-plex PCR, was developed for this. The polymerase used is a long PCR enzyme such as HerculaseII or IProof. The major problem for setting up this reaction mixture is that SYBR green modifies the migration of gDNA in a nonlinear manner. The migration bias is in part proportional to the amount of SYBR green used, and in part dependent on the amount of the amplicon.

In the present case, the high degree of multiplexing and the variations in intensity (frequency) between the amplicons make it difficult to develop the real-time PCR.

The inventors determined the amount of SYBR green sufficient to have enough fluorescent signal for the qPCR (FIGS. 12a and 12b): the reaction uses as a base the same reaction mixture as that presented above, with, in addition, SYBR green in an amount greater than 0.4×, final concentration, in a reaction volume of 25 μl (i.e. 1 μl at 10× initial concentration) and less than 2×, final concentration, with preferably a 1× final concentration. This amount is considered to be a maximum since, if this amount is too large, the SYBR green causes a bias in the migration, not to mention the inhibition of multiplex PCR which was observed if the amount is greater than 1.5×, final concentration.

Figure 12A:
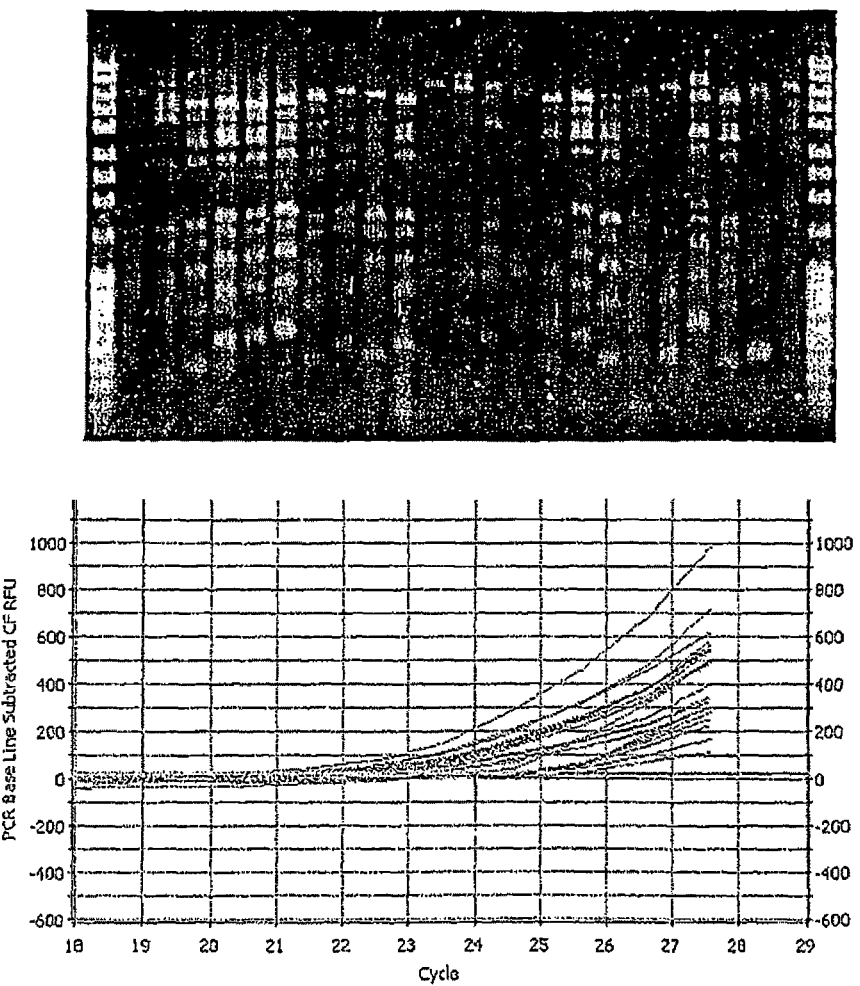
Figure 12B:
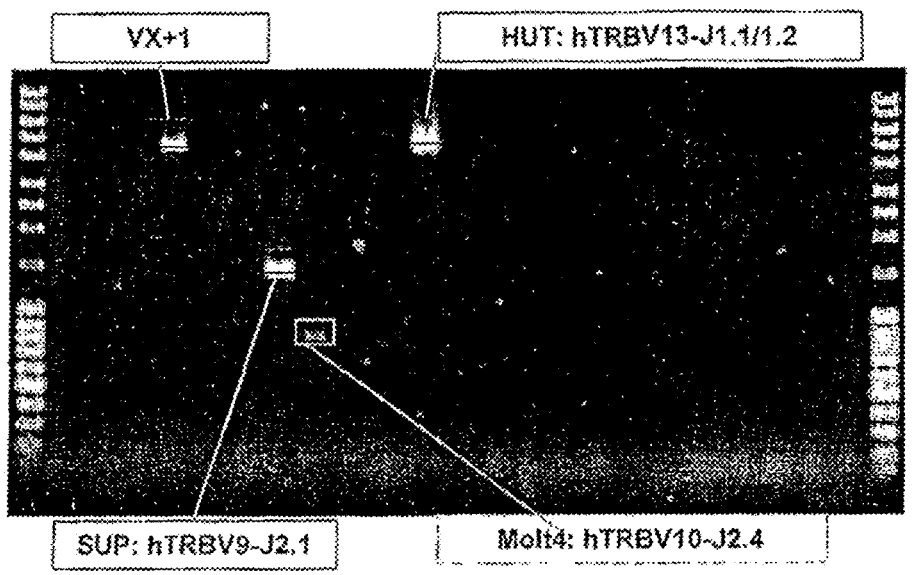
Figure 12B:
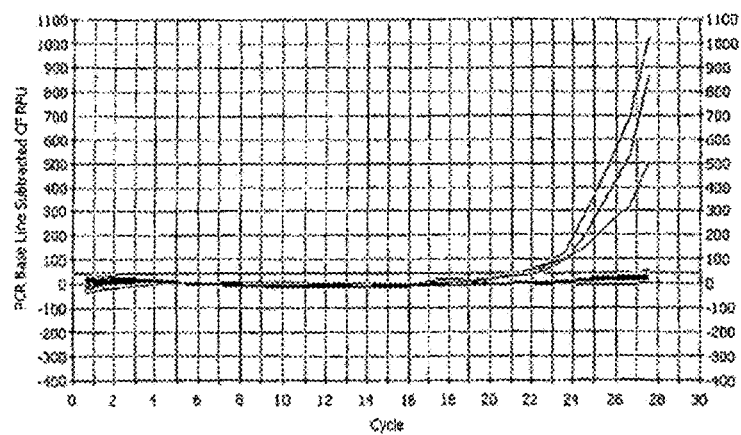
Figure 12C:
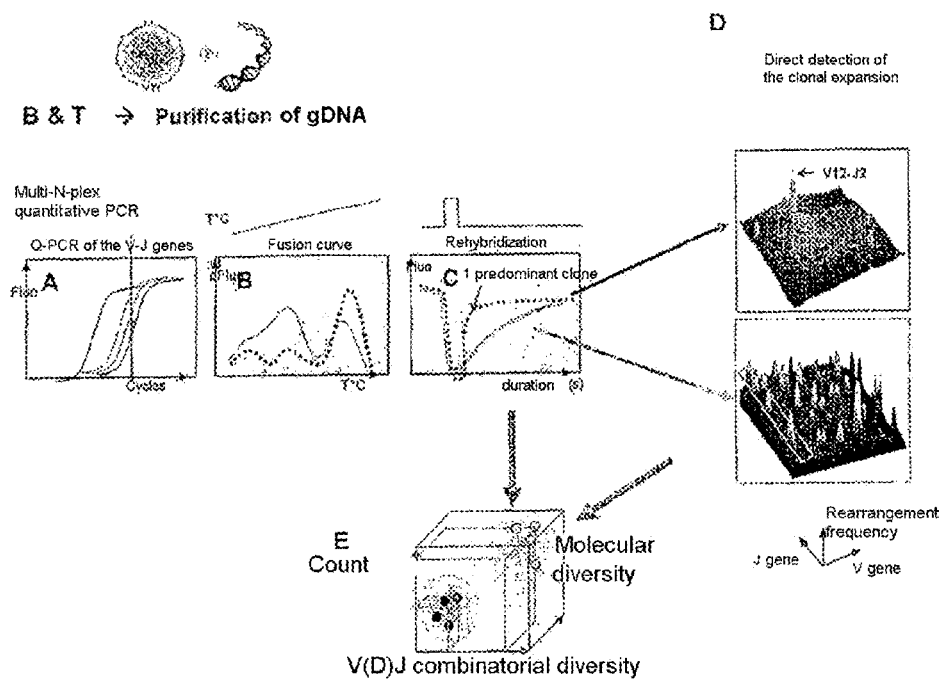

In the cases where the multi-n-plex PCRs are carried out with one primer specific for a V family and at least two primers specific for the J genes, this step, represented in graph A of FIG. 12c, makes it possible to detect the presence of a predominant V family (the signal detected corresponds to the sum of all the V-J rearrangements of the V family studied, of the Q-PCR tube in question).

There are several types of expected results:
DIVERSIFIED IMMUNE REPERTOIRE: In a healthy thymus or PBMC sample, using 50 ng of gDNA per Q-PCR, all the V families are generally detected using 20 cycles and up to a maximum of 27 cycles.

In a sample containing no lymphocyte, no signal is detected between 20 and 27 cycles.
REPERTOIRE COMPRISING ONE or MORE PREDOMINANT T OR B CLONE(S): In a sample containing predominantly one V-(D)-J clone, the curve corresponding to this V-gene family emerges between 20 and 27 cycles, but the curves corresponding to the other families are detected beyond cycles. This makes it possible to distinguish a V family predominantly represented in a sample.

Similarly, if n V families are present in large amount in the sample, we detect n curves in the 20-27-cycle window, and the other V families are detected later, >27 cycles, or even are not detected at all.

This makes it possible to have, in real time and in less than 2 hours, a diagnosis of lymphoproliferation with respect to 1 V family at the genomic level, using the multi-n-plex PCR technique.

Graph B of FIG. 12c illustrates the optional step of analyzing the melting curve. This step makes it possible to confirm the presence of a predominant amplicon in a PCR tube in one melting curve phase: increase in temperature from 40° C. to 95° C. (temperature for total dehybridization of the DNA). During this phase, the fluorescence in the tube is measured continually. If the curve contains several peaks of similar sizes, this means that there is not a predominant amplicon; if, conversely, one predominant peak is observed, this supports the fact that an amplicon is predominant in the PCR tube in question.

Graph C of FIG. 12c shows schematically the measurement of the molecular diversity. This step allows an additional confirmation of the presence of a predominant amplicon in one PCR tube through the measurement of the molecular diversity produced by the combination between the junctional diversity (CDR3), the combinatorial diversity (V-J) and the diversity derived from the somatic hypermutations.

Briefly, after having brought the temperature very rapidly down to 30° C. or below, this step consists in measuring the rate of rehybridization of the amplicons at constant temperature in one PCR tube, by measuring the re-emission of fluorescence.
In the case of a large "molecular" diversity, the number of different amplicons in one PCR tube is high and the rehybridization of said amplicons is slow (of the order of several couples of seconds, or even minutes) (solid curve). If, conversely, there is only one predominant amplicon (with one given V-J rearrangement, one given CDR3 region and given somatic hypermutations), the rehybridization of this amplicon is rapid (of the order of a second), which then produces a more vertical curve, such as that represented as dots.

In summary, this rehybridization step can be informative for measuring the order of magnitude of the "molecular" diversity of a sample, without the need to migrate the PCR products. The greater the molecular diversity, the smaller the sum of the director coefficients of the curves for each V family.

Overall, the 3 steps A/B/C make it possible to use the properties of the Q-PCR for identifying the presence of one or more overrepresented V families, without migrating the multi-n-plex PCR product.

However, it is not possible to determine the name of the J gene overrepresented, nor to measure the combinatorial diversity. If the scientist wishes to have this additional information, he or she must separate the PCR products and analyze the intensity of the bands corresponding to each of the rearrangements (graph D of FIG. 12c).

Graph E of FIG. 12c shows a graphic summary of the count as a function of the combinatorial and molecular diversity: if the lymphocyte count of the sample is known (measured independently of this experiment by conventional counting or by cytometry), it is possible to produce a three-dimensional graph with the V-J combinatorial diversity (by measuring the sum of the V-J rearrangements detected) and the molecular diversity (by measuring the sum of the director coefficients of the slopes of the V-gene families). Finally, this method makes it possible to obtain a better characterization of a patient, according to the diversity of the immune repertoire thereof.

In conclusion, this method makes it possible to monitor, with an unequalled degree of finesse, the change in immune diversity following a treatment. It is in particular possible to diagnose a degree of immunodeficiency very early.

EXAMPLE 13

Measurement of the Efficacy of a Treatment

Figure 13:
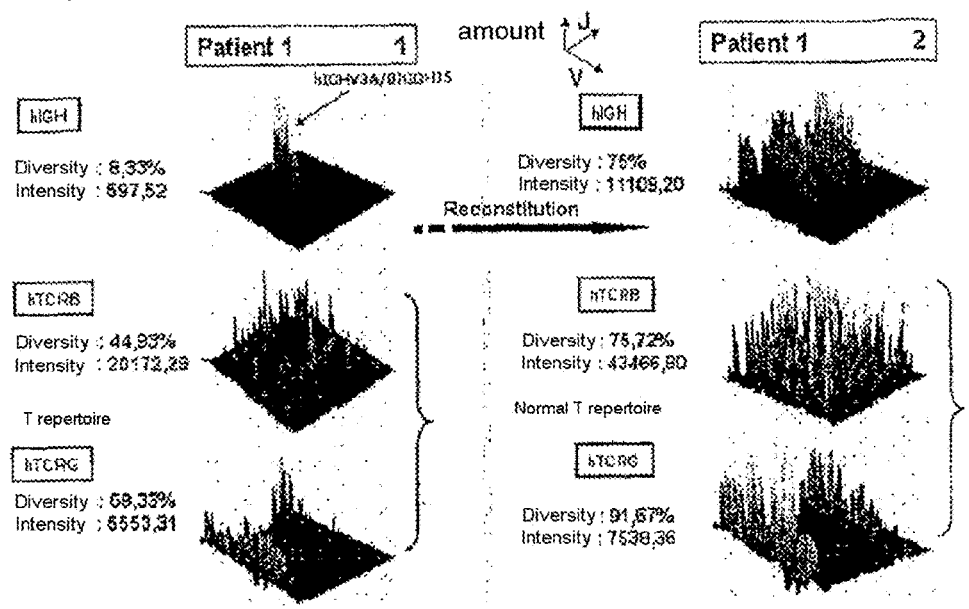
Figure 13:
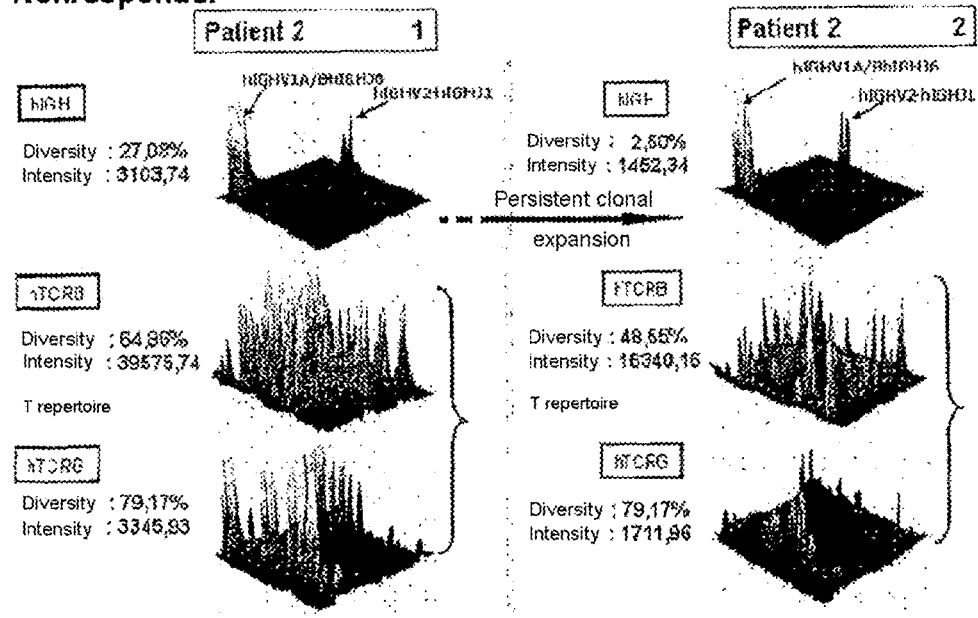

FIG. 13 presents two examples of analysis of the IgH and TCR repertoires at various times, in order to monitor the change in these repertoires in patients, in response to a treatment.

In the case of a B-cell chronic lymphoid leukemia (B-CLL), this pathological condition is diagnosed by identifying a strong signal for one or only a few B clones. The resolvent approach developed by the invention makes it possible to identify the name of the V and J gene, without needing to sequence the PCR product. This is particularly advantageous for monitoring the residual disease. FIG. 13 presents two situations: one prognosis which is positive (patient 1), the other being negative (patient 2). Specifically, if the treatment is effective (responding patient), the test measures an increase in the IgH combinatorial diversity, and also a stability, or even an increase, of the chains of TCRb and TCRg. Conversely, for the nonresponding (NR) patients, the diversity of one repertoire, or even of the 3 repertoires, decreases. The patient is more immunodepressed (immunosuppressed) after the treatment.

In the present case, the graphs are the result of the measurements of combinatorial diversity of the IgH, TCRb and TCRg chains.

These results show how this approach makes it possible to have the results of several tests in a single step starting from a single sample of less than 1 ml of blood: diagnosing CLL, identifying which B or T population originates from the lymphoproliferation, identifying the clone(s) involved by virtue of the V-J rearrangement thereof in order to be capable of monitoring it between various organs, and, where appropriate, finding the origin of the pathological condition. Moreover, the characterization of the predominant clone(s) enables longitudinal monitoring of the pathological condition, making it possible, in the end, to measure both the presence and the impact of the residual disease on the immune system. Added to this, in parallel, is the fine measurement of the degree of reconstitution of the immune repertoire as a function of the treatment of the patient: by virtue of this type of test, it is possible to rationally evaluate the overall degree of immunodeficiency of the patient and to correlate it with the level of infectious risk.

This method is therefore advantageous in several respects:
Facilitating patient classification.
Diagnosing and characterizing a B or T clone through the name of the V-J rearrangement thereof, in particular by simultaneously analyzing all the T and B lymphocyte repertoires.
Providing a prognosis for the progression of a pathological condition according to the V-J clone(s) involved in the pathological condition.
Monitoring the residual disease and making a comparison with the V-J combinatorial diversity.
Refining the monitoring of the progression of patients who have lymphocytosis.
Comparing the pathological condition between various sample sources: blood, spleen, lymph node, and endeavoring to specify, if possible, "the origin of the pathological condition" by quantifying the presence of the V-J clone between these various populations.
Moving toward a correlation of the infectious risk with the lympocyte count/diversity (LCD) level of each patient.

EXAMPLE 14

Distribution of Patients According to their TCR/Ig Diversity and their Count

Figure 14:
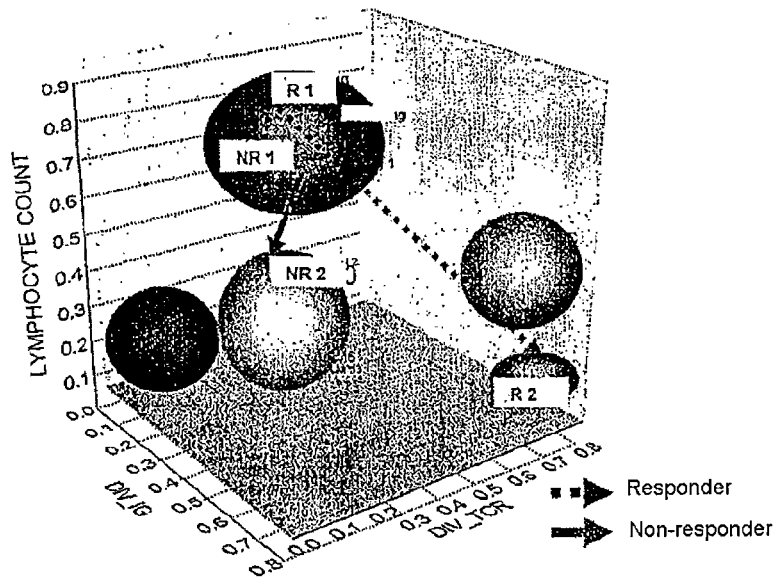

FIG. 14 shows a three-dimensional representation of the LCD (lymphocyte count/diversity). This graph groups together the measurement of diversity of the B lymphocytes and T lymphocytes, and also the count, as % or as absolute value, of the number of lymphocytes present in the sample.

The responding patient goes from a zone at risk (with a high count (approximately 80%), a low IgH diversity (8%) and a medium or even low diversity for the TCR (44%)) to a zone at lower risk, close to the PBMC samples (healthy control), with a decrease in the count (20%), and reconstitution of the IgH diversity (75%), the TCRb diversity (75%) and the TCRg diversity (90%).

Conversely, a nonresponding (NR) patient remains in the zone at risk and undergoes an overall immunosuppression (decrease in the count, which does not result from the efficacy of the treatment, contrary to what the clinician might believe if he or she looked only at this marker), and a decrease in the IgH, TCRb and TCRg repertoire.

This illustrates the paradox of the count, sole use of which can result in interpretation errors. Specifically, it is important to note that the lymphocyte count between these two samples does not change in the same way as the diversity of the combinatorial repertoire. It is therefore particularly advantageous to couple the count information and the repertoire diversity information in order to judge the real state of health of the patient. Specifically, in the present case, the leukocyte count goes from 78% to 21%, whereas the V-J combinatorial diversity goes from 8% to 75%. This approach makes it possible to verify, in a single step, and less expensively, that the patient in question has benefited from a good degree of reconstitution of the immune repertoire and that there is less risk of said patient experiencing an infectious disease. It should be noted that this is coherent with the decrease in CD19/CD5 cells indicating the presence of LCC, which goes from 84% to 4%.

EXAMPLE 15

Figure 15:
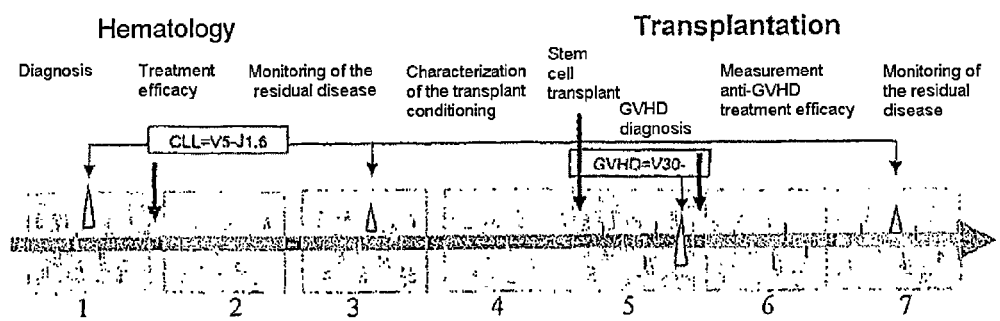

Dynamic Immunomonitoring from Initial Diagnosis to Monitoring of a Stem Cell Transplant FIG. 15 presents, in diagrammatic form, the application of the method of the invention to the monitoring of the reconstitution of the immune repertoire in a patient having undergone a stem cell (marrow) transplant.

Step 1: Measurement of the immune diversity, initial diagnosis, detection of the clone(s) of T cells or of B cells (darker clones).
Step 2: Evaluation of the efficacy of the treatment.
Step 3: Monitoring of the residual disease.
Step 4: Evaluation of the preparation of the repertoire of the recipient patient (conditioning of the transplant).
Step 5: Measurement of the reconstitution of the V-J diversity of the patient and early diagnosis in the event of GVHD (graph versus host disease).
Step 6: Evaluation of the efficacy of the treatment.
Step 7: Monitoring of the residual disease.

The longitudinal study of a patient by means of the method represented here allows a personalized treatment suitable for each situation.

The result of the test presented here makes it possible to measure the degree of severity of the disease and to be as sure as possible that the treatment is effective, by avoiding treating patients who would be non-responders to the treatment. The immune repertoire is here used as a general biomarker of the state of health of an individual. It is used on two levels: 1/for evaluating the patient's infectious risk, 2/while at the same time monitoring in a resolvent manner any T or B lymphocyte clones that may be the signature of a pathological condition. By virtue of a longitudinal study carried out on successive blood samples taken from a patient, it is thus possible to monitor the level of the immune repertoire throughout the treatment in order to be sure that the latter has indeed been effective and that the patient conserves a diversified immune repertoire in order to defend himself or herself against bacterial or viral infections. This dynamic diagnosis allows the clinician to adapt the treatment to his or her patient as well as possible, by proposing said patient the appropriate medicament at the correct dose and at the correct time.

Another advantage of the principle of the prior diagnostic test is to avoid giving too much treatment to a "responding" patient for whom the treatment at the minimum dose is effective.

EXAMPLE 16

Monitoring of an Ex Vivo Treatment Against GVHD

Figure 16:
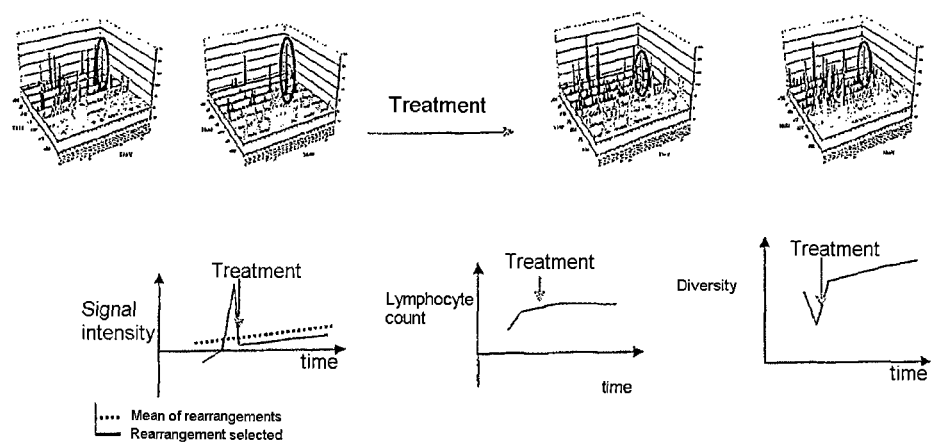

The four mappings in FIG. 16 illustrate steps 5 and 6 of the previous figure. The four mappings represent the diversity of the immune repertoire measured using samples from the same patient at two times before the treatment (approximately 200 and 250 days), and two times post-treatment (approximately 300 and 600 days). The results concerning these four samples are represented according to the intensity, the count and the diversity.

1. The decrease in the diversity of the repertoire corresponds well to the appearance of a clone. The ex vivo treatment appears to have inhibited the clonal expansion (which represents close to 10% of the combinatorial repertoire monitored). The intensity corresponding to this rearrangement is systematically greater than the average intensity of the rearrangements.

2. The proportion of lymphocytes in the PBMCs (count) reaches its maximum around D300, and then decreases slightly around D600.

3. The degree of combinatorial diversity follows a reverse tendency. The increase in the proportion of T lymphocytes does not correspond to an increase in the diversity. Contrary to what would be expected, the diversity decreases between point 1 and point 2.

The ex vivo treatment appears to have reversed the tendency. The reconstitution takes place in two phases: the repertoire rapidly recovers a degree of diversity of 35% around D300, and then the reconstitution is slower and reaches approximately 40% around D600.

These results therefore show a repertoire at the periphery that is initially restricted in comparison with positive controls on a healthy thymus repertoire and on four healthy donors. The use of the method of the invention makes it possible to measure that, after D600, the degree of reconstitution of the TCR repertoire is close to that of the healthy donors. This approach therefore makes it possible to evaluate the efficacy of a treatment and to see its impact on the immune reconstitution kinetics. Finally, the use of the method of the present invention made it possible to verify that the profile of the combinatorial repertoire of the donors could be conserved on a long-term basis in the recipient, hence the fact that more systematic attention should be given to the analysis of the repertoire of donors in order to explain the change in an allograft over time.

The method presented here is therefore a particularly advantageous tool for clinicians who perform bone marrow grafts, since it makes it possible, inter alia, to describe and monitor clonal expansions corresponding to a Graft Versus Host (GVH) in the recipient. It also makes it possible to obtain better monitoring of the reconstitution of the repertoire post-bone-marrow-graft. The clinician will then be able to adjust the treatment in a personalized manner, by measuring the GVH/GVL ratio with greater finesse by virtue of the monitoring of the V-J combinatorial diversity.

EXAMPLE 17

Development of Humanized Transgenic Animals (Having a Human Immune Repertoire)

Figure 17:
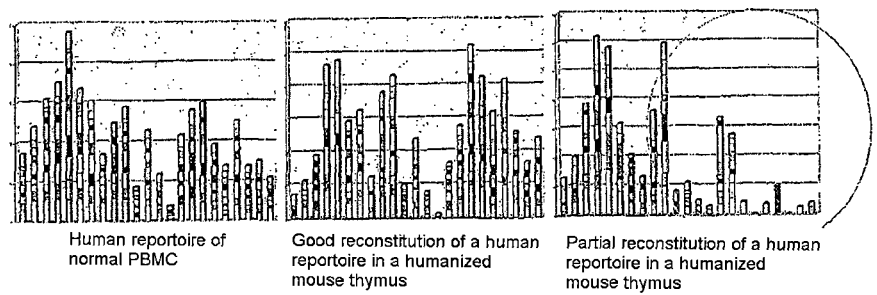

The results are presented in FIG. 17.

The present method makes it possible to evaluate, with the human TRB ImmunTraCkeR kit, the quality of reconstitution of the immune repertoire of a "humanized" transgenic mouse. In this example, the biological sample studied is derived from the spleen of an "immunodeficient mouse" (which does not have immune cells), having received an injection of CD34+ cells. These cells have the ability to diversify and to reconstitute an immune system. The method makes it possible to represent the diversity of the V-J repertoire in a two-dimensional graph. Each histogram corresponds to a V family and, within a histogram, the subdivisions correspond to a given J gene. The lowest subdivision of each histogram corresponds, in this example, to J2.7 and the highest corresponds to J1.1. It is possible to screen the "humanized" mice having an immune repertoire that is completely reconstituted (graph on the right), from the mice having a well-diversified repertoire (graph in the center), with a distribution of rearrangements that is close to that observed in a sample of human PBMC (graph on the left).

EXAMPLE 18

Use of the Method as a Tool for Screening Molecules In Vitro

Figure 18:
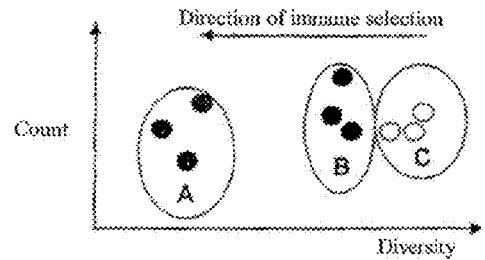

The study represented by FIG. 18 shows the evaluation of the effectiveness of an epitope (an antigen) in the case of the development of a treatment (vaccine), by measuring the decrease in diversity of the immune repertoire of a sample containing T lymphocytes. It is shown that, the more the diversity decreases, the greater the selection of the epitope-specific lymphocytes.

In this figure, three cases are represented:
A: The epitope tested results in a considerable lymphocyte selection, as indicated by the decrease in the diversity.
B: The epitope tested is not very selective, as can be observed by comparison with a negative control.
C: Negative control.

This epitope screening test makes it possible to identify the epitopes that stimulate the immune repertoire. It is possible to correlate the number of peaks (number of T clones) with the efficiency of selection and of activation of the immune repertoire.

FIG. 18 is derived from a qualitative and quantitative study of the murine TCRbeta repertoire using genomic DNA. By using the primers described in example 21 below (mouse TRB ImmunTraCkeR kit) to obtain the measurement of the mTRBV-J combinatorial diversity and of the intensity and the homogeneity of the repertoire, it is possible to evaluate, on this animal model, the efficacy of various vaccine protocols.

In another case of evaluation of the effectiveness of an epitope, illustrated by FIG. 18, the model for which the T repertoire is studied corresponds to an in vitro culture of lymphocytes. In this case, the study of the diversity of the T repertoire on samples of gDNA, originating from an in vitro lymphocyte culture, makes it possible to measure the clonal expansion of certain TCR alpha, beta, gamma and delta and hIgH genes following antigen presentation by presenting cells.

Of course, in addition to the selection of the antigen for inducing a selective immune response, there is the ability to identify the best method of injection (injection number and frequency, injection site and dose).

FIG. 18 illustrates another use of the method presented herein. Specifically, the epitope selection can be an undesired event during the development of new therapeutic approaches. In this case, it is important to evaluate the immunotoxicity (immunotoxicology) in order to eliminate the proteins which induce an unexpected activation of the immune system. This makes it possible to screen molecules, such as monoclonal or polyclonal antibodies for therapeutic purposes, so as to be sure that they do not induce an inappropriate lymphocyte activation.

Thus, the method presented herein is a particularly advantageous tool for preclinical and clinical research, as a tool for evaluating new therapeutic, and in particular vaccine, approaches. Whether on cells in culture, in the animal model or in humans, the object of the tool thus described is to provide a verdict on the quality of the expected impact on the immune system, either through a specific activation or through an absence of activation.

By extension, it is possible to perform quality control on the immune repertoire by monitoring one or more clone(s)

EXAMPLE 19

Comparison with Other Existing Technologies

Figure 19:
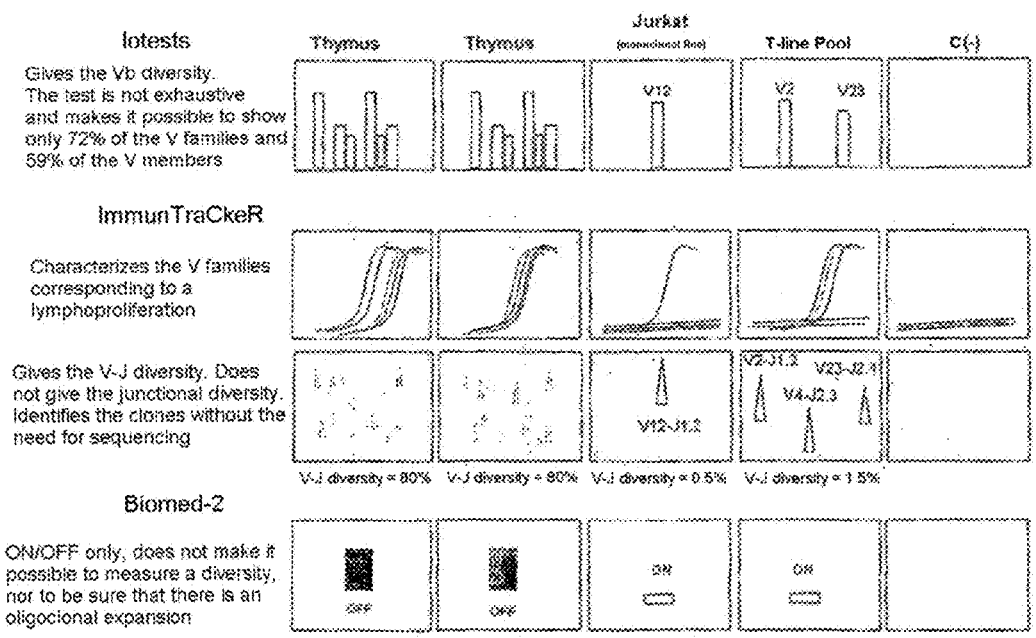

FIG. 19 shows the summary of the results describing the comparison of various techniques for immunomonitoring of the immune cell repertoires. Various samples were studied by each of the techniques. The cell samples were treated in a controlled manner in order to prevent any bias due to the preparation of the sample.

Two samples called "Thymus", corresponding to thymus-derived cells, were tested. The thymus is the organ where the maturation and selection of certain immune cells takes place. These samples are chosen since they are made up of a diversified repertoire not representing clonality, with numerous immune cells having various rearrangements (polyclonality) being present.

Two other samples were chosen to represent a cell population much less diverse than for thymus samples: the "Jurkat" sample which corresponds to the Jurkat cell line (monoclonality) and also the "T-line pool" sample which corresponds to a mixture, in known proportions, of three cell lines (oligoclonality). Finally, a sample called "C(−)" corresponds to a negative control, which is a cell mixture that does not comprise immune cells.

In addition to the present method with the human TRB "ImmunTraCkeR" kit in accordance with the invention, two techniques which make it possible to provide various pieces of information on the quality of the immune repertoire were studied. Firstly, the "Iotests" cell test (the company Beckmann Coulter), which is based on Vbeta-repertoire antigen recognition, using flow cytometry, by means of a kit of specific antibodies; this test makes it possible to identify the presence of 72% of families and 59% of the V members. Secondly, a "Biomed-2" molecular biology test (Biomed-2 European consortium), which is based on multiplex PCR approaches according to a principle different than the present invention, which makes it possible to identify whether there is a very highly represented clone in a given sample.

The analysis of the results observed makes it possible to identify that the "ImmunTraCkeR" test makes it possible to identify, in real-time PCR measurement, whether the sample is clonal ("Jurkat"), oligoclonal ("T-line pool") or polyclonal ("Thymus"). The analysis also shows that analysis of the amplicons (rearrangements amplified according to the "ImmunTraCkeR" method) makes it possible to observe precisely which clones are present in terms of Vx-Jy rearrangement, without a sequencing step, whether for the "Jurkat", oligoclonal ("T-line pool") or polyclonal ("Thymus") sample. The representativeness of the diversity of the combinations observed is given as a percentage (relative to a theoretical diversity where 100% of the Vx-Jy rearrangements would be observed).

The "Biomed-2" test clearly makes it possible to identify the very predominant presence of a clone in the sample. The "Biomed-2" test does not make it possible to distinguish between the presence of one or of a few clones if this case occurs, and this test will have a signature showing that the sample is clonal even if there is oligoclonality ("T-line pool"): the test is positive ("On") in the two cases.

The "Iotests" test, which is a test carried out using fresh cells, makes it possible to distinguish clonality from oligoclonality and from polyclonality. However, unlike the "ImmunTraCkeR" test, only the Vbeta segments are studied. In addition, since the Vbeta antibodies are not exhaustive in the antibody kit of this test, the V4 rearrangement is not observed, whereas it is observed with the "ImmunTraCkeR" test.

The results of this study presented in FIG. 19 show that the "ImmunTraCkeR" test has a greater technical capacity than the other two tests evaluated for analyzing immune repertoires and that, consequently, this test enables a more extended study of immune repertoires.

EXAMPLE 20

Protocol for Production of hTCRB Tests

Figure 20:
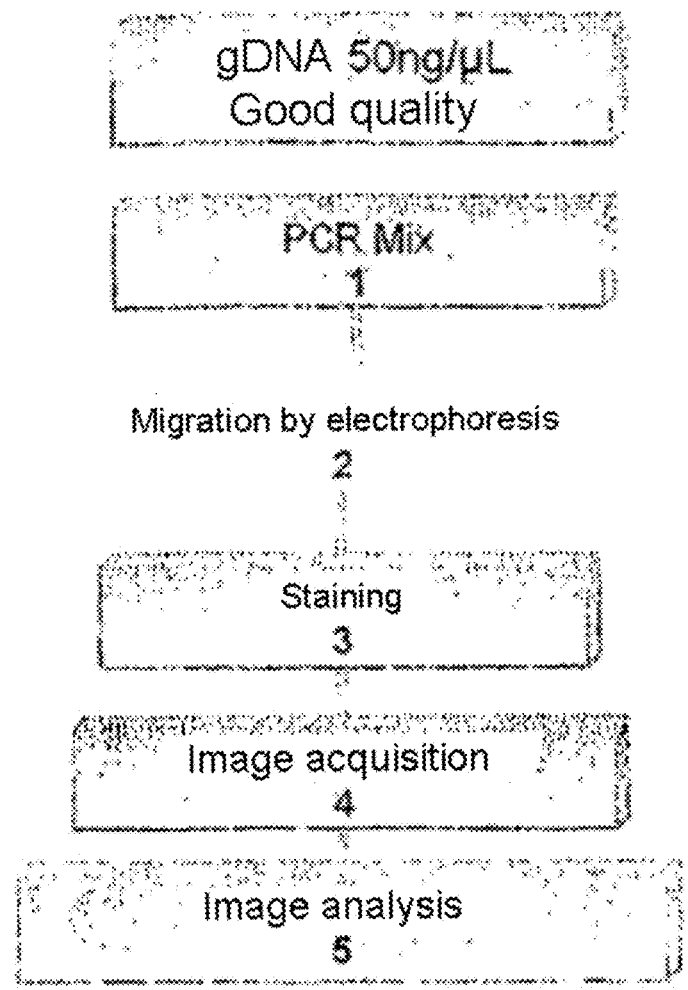

In order to use the method which is described in this document, and to carry out analyses with one of the "ImmunTraCkeR" kits under good conditions, in addition to monitoring the steps for carrying out the test (presented in FIG. 20), it is preferable to have produced the test by following a production protocol and according to good production practice.

In order to carry out a controlled production of kits for performing hTRbeta tests (or human TRbeta "ImmunTraCkeR" kit), it is necessary to be sure that the individual who must carry out production of the test for use, ultimately, in a study on samples, adheres to the various steps stated hereinafter according to the desired use.

Production of 12 hTRBeta Tests
Preparation of the "Oligo Mix"
Preparation of the Material
One Greiner plate (support)
Three 8-well arrays+stoppers
Microtubes of 0.5 mL and 1.5 mL
Pipettes, tips
Sterile $H_2O$
EB
Dilution of the Vβs:
100 μM to 20 μM
Calculation: 20×Vf/100=Vi
Therefore, in a 0.5 mL microtube: Vi μL of oligo at 100 μM+(Vf−Vi) of EB.
20 μM to 3.5 μM
Calculation of the volume necessary for the production of 12 kits+10%: 12*1.67=20.04+10%=22 μL
Calculation: 3.5×22/20=3.86 μL
Therefore, in a 0.5 mL microtube: 3.85 μL of oligo at 20 μM+18.15 μL of $H_2O$
Dilution of bc1do2 & 2S7do1:
100 μM to 20 μM
Calculation: 20×Vf/100=Vi
Therefore, in a 0.5 mL microtube: Vi μL of oligo at 100 μM+(Vf−Vi) of EB.
20 μM to 3.5 μM
Calculation of the volume necessary for the production of 12 kits+10%: 23*12*1.67=461+10%=507.1 μL
Calculation: 3.5×507.1/20=88.74 μL
In a 1.5 mL Eppendorf tube: 88.74 μL of oligo at 20 μM+418.36 μL of $H_2O$
Distribution of the oligos Bc1do2 & 2S7do1
Pool of Bc1do2 and 2S7do1 diluted to 3.5 μM in a sterile hemolysis tube.
Distribute 44.1 μL of this pool into each 0.5 mL microtube containing the diluted Vβs.
Mix by drawing up and down, vortex vigorously and then centrifuge briefly.
Distribution of oligos Vβ-Bc1do2-2S7do1

Distribute 66 μL of the "Vβ-Bc1do2-2S7do1" mix into the 8-well arrays, maintaining the following Vβ order:

Array n°1: Vβ2up2, Vβ3up2, Vβ4up_ex, Vβ5pool, Vβ6pool, Vβ7pool, Vβ9up_ex, Vβ10pool Array n°2: Vβ11up_ex, Vβ12pool, Vβ13up1, Vβ14up_ex, Vβ15up_ex, Vβ16up1, Vβ18up1, Vβ19up2

Array n°3: Vβ20-1up_ex, Vβ24up_ex, Vβ25up_int, Vβ27up2, Vβ28up_G, Vβ29up_G, Vβ30up1

Preparation of the Kits
Preparation of the Material
Three Greiner plates (support)
3*12 8-well arrays+stoppers
Pipettes, tips
Production of 12 Tests Using the multichannel pipette, 5 μL of mix of arrays 1 to 3 (vol/well=64 μL) are distributed into each well of the corresponding 12 arrays.

For a batch of n tests, at least two tests will be used to control the quality and the conformity of the production. Among the various controls performed throughout the production so as to enable traceability and control of any drifting on a batch, the functional controls which make it possible to verify the quality before validation of the batch are important. In this respect, FIG. 21 proposes examples on three samples of control of a test derived from a production batch. These three samples are those on which a systematic control is carried out during productions. The results are systematically compared with the preceding results in order to identify any difference. Each new result makes it possible to refine the tendency and the acceptable upper and lower limits for it to be possible for the tests to be used in a study of immune repertoire.

Figure 21:
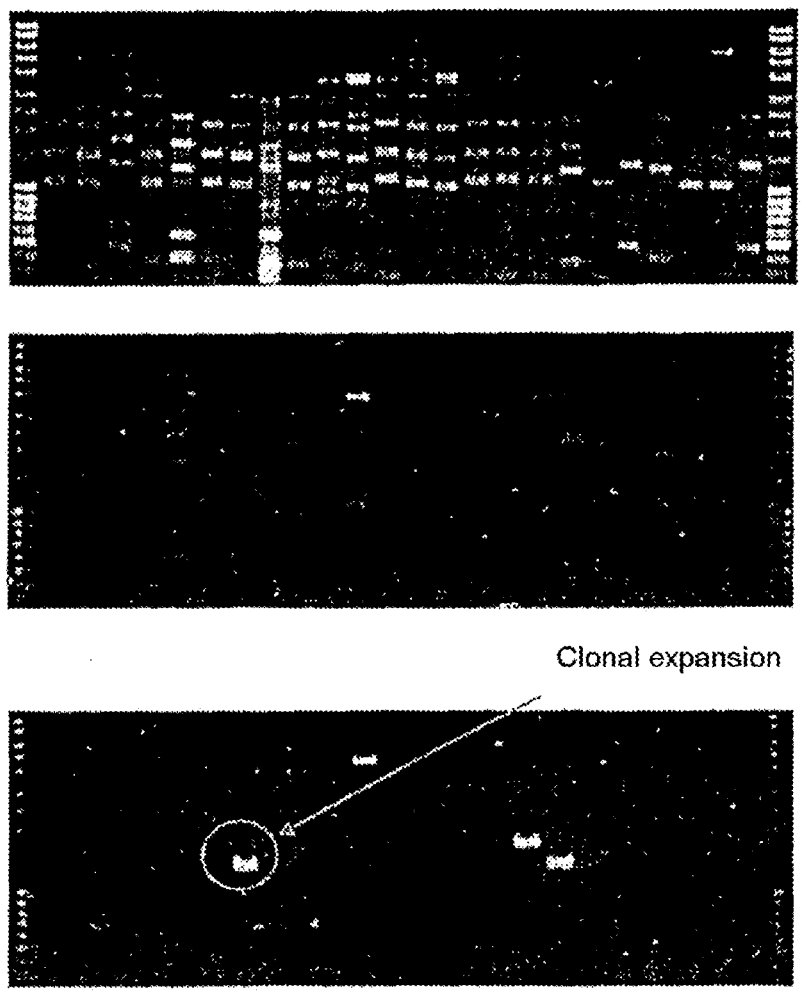

FIG. 21 represents, from top to bottom, the expected result for a thymus immune repertoire (polyclonality), an immune repertoire when the sample comprises only one very predominant clone (clonality) and, finally, an immune repertoire when the sample comprises several clones (oligoclonality).

The protocol above can be adapted for producing mouse TRB tests with the kit of oligonucleotides as described in example 21 hereinafter, and also for any other test production.

EXAMPLE 21

Application of the Method to the Analysis of the TRB Locus in Mice

The protocols and methods described in the present text can be adapted to the study of the murine TRB repertoire, using the primers described in the table below.

TABLE 15

| Name of gene | Oligo-nucleotide name | Size (nt) | Distance with the end of the V gene in bp | Sequence | SEQ ID No | Oligo-nucleotide orientation |
|---|---|---|---|---|---|---|
| TRBV1 | mTRBV1up1 | 23 | 153 | GTGGCTGTTCACTCTGCGGAGTC | 99 | SENSE |
| TRBV2 | mTRBV2up1 | 28 | 135 | TCAAAAACTTATGGACAATCAGACTGCC | 100 | SENSE |
| TRBV3 | mTRBV3up1 | 26 | 292 | CAGGACCCAAAGTCTTACAGATCCCA | 101 | SENSE |
| TRBV4 | mTRBV4up1 | 25 | 124 | TTGTAAACGAAACAGTTCCAAGGCG | 102 | SENSE |
| TRBV5 | mTRBV5up1 | 24 | 227 | TTGGAATGTGAGCAACATCTGGGA | 103 | SENSE |
| TRBV12 | mTRBV12up1 | 25 | 105 | CCCAGCAGATTCTCAGTCCAACAGT | 104 | SENSE |
| TRBV13 | mTRBV13up1 | 22 | 287 | TGGAGGCTGCAGTCACCCAAAG | 105 | SENSE |
| TRBV14 | mTRBV14up1 | 28 | 130 | GTTATAGATAATTCACAGTTGCCCTCGG | 106 | SENSE |
| TRBV15 | mTRBV15up1 | 24 | 362 | TTCCGTGTTCATAACTCCACAGCG | 107 | SENSE |
| TRBV16 | mTRBV16up1 | 23 | 62 | CTGAAGATCCAGAGCACGCAACC | 108 | SENSE |
| TRBV17 | mTRBV17up1 | 25 | 108 | TTTTGAGAAGTTCCAATCCAGTCGG | 109 | SENSE |
| TRBV19 | mTRBV19up1 | 27 | 113 | CGATCTATCTGAAGGCTATGATGCGTC | 110 | SENSE |
| TRBV20 | mTRBV20up1 | 25 | 199 | CTGTAGCTTGGTATCGTCAATCGCC | 111 | SENSE |
| TRBV23 | mTRBV23up1 | 27 | 376 | AACACACCCAAATAATTTTCCTTGCTG | 112 | SENSE |
| TRBV24 | mTRBV24up1 | 27 | 61 | TGGAAATCCTATCCTCTGAAGAAGACG | 113 | SENSE |
| TRBV26 | mTRBV26up1 | 24 | 395 | TCTTTGACCTGGAGATTGCCAACC | 114 | SENSE |
| TRBV29 | mTRBV29up1 | 24 | 99 | ATACAGGGTCTCACGGAAGAAGCG | 115 | SENSE |
| TRBV30 | mTRBV30up2 | 23 | 155 | ATGGCAACTGCAAATGAAGGCTC | 116 | SENSE |
| TRBV31 | mTRBV31up1 | 24 | 73 | ACGACCAATTCATCCTAAGCACGG | 117 | SENSE |

TABLE 15-continued

| Gene name | Oligo- nucleotide name | Size (bp) | Distance with the start of the J gene in bp | | | Oligo- nucleotide orientation |
|---|---|---|---|---|---|---|
| TRBJ1.7 | mTRBJ1.7do1 | 26 | 2315 | GCATGGCTATTTGAAACAGTGGCTCT | 118 | ANTISENSE |
| TRBJ2.7 | mTRBJ2.7do1 | 22 | 241 | CCTTGTCCTGGCTTGCGAGAGA | 119 | ANTISENSE |

EXAMPLE 22

Examples of Results Obtained by Quantitative PCR Analysis of the Combinatorial Immune Repertoire on Genomic DNA The use of quantitative PCR according to the invention makes it possible to rapidly classify a patient in one of the following three categories: healthy (as regards the condition of said patient's immune system), lymphoproliferation or lymphopenia. Real-time PCR makes it possible to have results in 2-3 hours instead of 5 hours for an analysis by "non-real-time" PCR requiring migration of the amplification products. Ultimately, this increase in speed of return will make it possible to carry out health monitoring on patients.

Figure 22A:
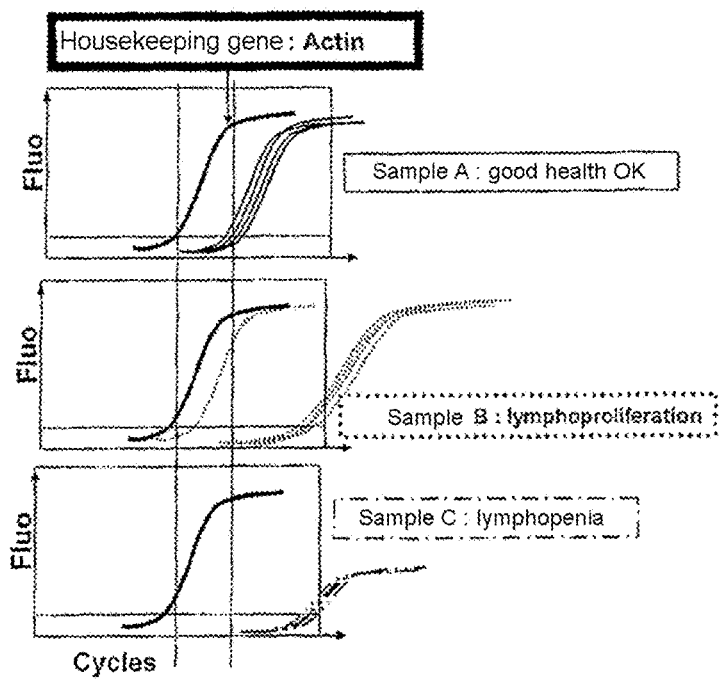
Figure 22B:
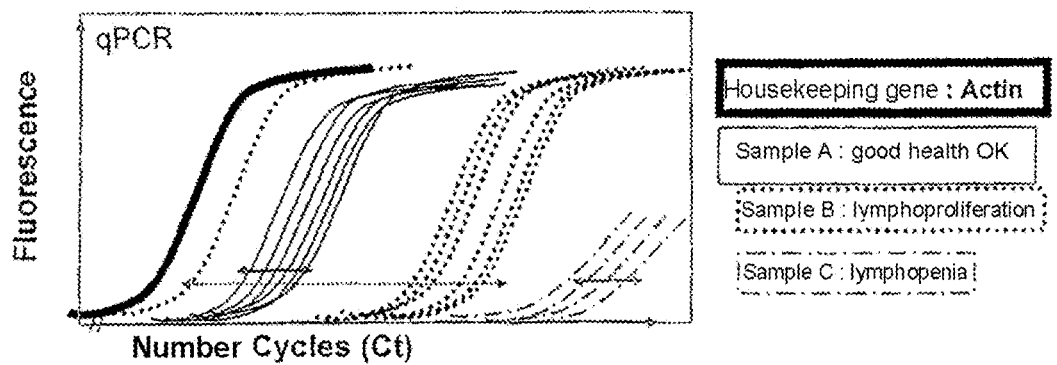

The three situations are illustrated in FIG. 22. FIG. 22a presents a diagram of the three separate situations; FIG. 22b presents a summarizing diagram of the three situations. N.B.: other than for the control gene (in this example, the Actin gene), each curve corresponds to the PCR amplification of the sum of the rearrangements of a given V gene with all the J genes monitored.

The first situation (sample A) is that of a "healthy" individual, where all the amplifications are detected grouped together, in a Ct range of less than five cycles, this being the case between two and six cycles after the detection of the housekeeping gene.

The second diagram of FIG. 22a is characteristic of a "lymphoproliferation" (sample B), where at least one amplification of a V gene is detected earlier than the group of the other curves (which corresponds to a monoclonality if one curve "emerges" before the others, and to an oligoclonality if it is the case of a few curves). Depending on the degree of lymphoproliferation, this (or these few) curve(s) will be more or less close to the curve of the Actin gene (the greater the degree of lymphoproliferation, the closer said curve(s) will be; the detection may even be observed before the housekeeping gene); conversely, the detection of the other rearrangements will occur later when the degree of lymphoproliferation is greater (the curves are therefore shifted to the right). Observation: if the lymphoproliferation is monoclonal, the amplification of the corresponding rearrangement may be detected at the same time as the actin (in certain cases, in particular if the amplification efficiency of the corresponding primers is greater than that of the pair of primers for the actin gene, this detection might be before the actin). If the lymphoproliferation is monoclonal, the other rearrangements will be virtually undetected, or be detected after a high cycle number (more than five cycles after the detection of the predominant rearrangement).

In the event of early detection of a rearrangement not present among the ten rearrangements normally most represented, there is a suspicion of clonality, and it is necessary to monitor the patient in order to confirm or refute this risk.

The third diagram of FIG. 22a represents a case of "lymphopenia" (sample C): despite detection of the control gene (for example, actin) at a cycle number similar to the healthy individuals, demonstrating a comparable amount of gDNA and an absence of PCR inhibition, the detection of the rearrangements is very late. This is the sign of a very small presence of rearrangements, which shows that there are very few lymphocytes in the sample.

EXAMPLE 23

Interpretation of the Results Obtained by QPCR

Direct Identification, by Quantitative PCR, of a Lack of Lymphocyte Diversity Associated with a Lymphopenia The inventors defined two novel indices for interpreting the results obtained by means of the methods according to the invention, in particular for identifying a lack of lymphocyte diversity, in particular associated with a lymphopenia.

The first index, referred to herein as "divpenia ratio", is calculated in the following way:

"divpenia ratio"=[cycle of emergence of the actin quality control]/[mean (or median) of the cycles of emergence of the V rearrangements of the sample].

Of course, this index, the objective of which is to easily identify a lack of diversity, can be adapted by those skilled in the art to any control gene other than actin. In the present case, a ratio of less than 0.78, and more particularly less than 0.74 (measured by QPCR), is an indicator of a low combinatorial immune diversity (situation described herein as "divpenia").

This index, measured in the three situations presented in example 22 above, gives the following results:

Sample A "Normal"

"divpenia ratio"=20 cycles (Ct Actin)/Mean (or median) rearrangements 25 cycles=0.80.

Sample C "Lymphopenia"

"divpenia ratio"=20 cycles/28 cycles=0.71.

Other means of identifying a lymphopenia by QPCR: in the case where the two samples show detection of the control gene at the same number of cycles, another means of identifying a lymphopenia is to directly subtract the mean of the number of cycles for detection of the rearrangements of a sample of a "healthy" individual from the mean of the individual tested. In this example, between sample A (healthy) and sample C, a difference in the mean Cts of 28−25=3 cycles of mean difference is observed, i.e. approximately $2^3$=8 times less signal detected on average in the lymphopenic patient.

Identification of a Lymphoproliferation Directly by QPCR

In a given sample, lymphoproliferation (of a lymphocyte) is associated with increased detection of the corresponding V-J rearrangement. In QPCR this consists in detecting the corresponding V gene from a very low number of QPCR cycles onward. The greater the lymphoproliferation of this lymphocyte, the greater the proportion of the sample represented by the lymphocyte. As a result, the detection of the corresponding rearrangement takes place at a cycle number close to the Actin gene (or even before, cf. observation in example 22). Conversely, the other rearrangements of the sample are less frequent and their detection requires a greater number of QPCR cycles. In the end, this results in an increase in the difference between the Cts corresponding to the detection of the first and of the last rearrangements detected. If this difference (delta Ct) is greater than n cycles, this indicates the presence of a lymphoproliferation, which is all the greater, the larger this delta is.

This approach therefore makes it possible to detect the presence of a lymphoproliferation by QPCR and characterize the name of the V family involved. To identify the V-J rearrangement, it is sufficient to subsequently migrate the QPCR products and to characterize it according to the expected size.

N.B.: given knowledge of the list of the ten TRB rearrangements predominantly detected in the PBMCs, it is also possible, in certain cases, to have suspicions of "emerging" clonality if families of TRBV genes not present in this list are detected.

*$\Delta Ct$ index=[$Ct$max]−[$Ct$min] for a sample.

In practice, it is considered that there is no lymphoproliferation if $\Delta Ct$ <6 cycles and that a $\Delta Ct$ index >6 cycles indicates lymphoproliferation of a clone, which then represents at least 10% of the lymphocytes of the sample.

Samples A and C:

$\Delta Ct = 27 - 24 = 3$ cycles.

Sample B:

$\Delta Ct = 30 - 23 = 7$ cycles, which clearly indicates a lymphoproliferation.

N.B.: it is preferable to use a ratio for measuring the lack of diversity and a difference in Ct for identifying a clone, or vice versa, in order to avoid errors and to be able to work in a standardized manner with respect to the amount of genomic DNA of the sample, which is measured by detection of the control gene (housekeeping gene or the like).

The table below describes the detection, by quantitative PCR, of the cycles for emergence (Ct) of the first ten V genes detected, on three different PBMC samples. This table gives the Ctmax (last PCR product detected), the Ctmin (rearrangement detected first), the Delta Ct between Ctmax and Ctmin, the median of the Cts of the sample (excluding CQ actin) the mean of the Cts of the sample (excluding Ct Actin), the "divpenia" ratio between Ct Actin and the median or the mean of the Cts.

| Genes | Ct cycles | Indices | Value | Interpretation |
|---|---|---|---|---|
| PBMC Per | | | | |
| QC Actin | 22.02 | | | |
| BV4 | 24.18 | | | |
| BV24 | 24.28 | CtMax | 29.32 | |
| BV20 | 24.46 | CtMin | 24.18 | |
| BV27 | 24.56 | Delta Ct Max − Min | 5.14 | Very low risk of lymphoproliferation |
| BV6 | 24.7 | | | |
| BV5 | 25.53 | Median Ct | 26.13 | |
| BV7 | 25.72 | divpenia ratio [Ct actin]/[Median Ct] | 0.842709529 | Low risk of divpenia |
| BV30 | 25.95 | Mean Ct | 26.29 | |
| BV12 | 26 | divpenia ratio [Ct actin]/[Mean Ct] | 0.837580829 | Low risk of divpenia |
| BV15 | 26.07 | | | |
| BBMC Br | | | | |
| QC Actin | 19.99 | | | |
| BV20 | 23.7 | | | |
| BV6 | 24.17 | CtMax | 28.5 | |
| BV5 | 24.26 | CtMin | 23.7 | |
| BV24 | 24.48 | Delta Ct Max − Min | 4.8 | Very low risk of lymphoproliferation |
| BV7 | 24.59 | | | |
| BV27 | 24.63 | Median Ct | 25.27 | |
| BV7 | 24.65 | divpenia ratio [Ct actin]/[Median Ct] | 0.791056589 | Low risk of divpenia |
| BV30 | 24.7 | Mean Ct | 25.54 | |
| BV12 | 24.72 | divpenia ratio [Ct actin]/[Mean Ct] | 0.782693814 | Low risk of divpenia |
| BV15 | 24.93 | | | |
| PBMC SH | | | | |
| QC Actin | 23.45 | | | |
| BV20 | 23.51 | | | |
| BV6 | 23.77 | CtMax | 27.56 | |
| BV4 | 23.83 | CtMin | 23.51 | |
| BV5 | 24.54 | Delta Ct Max − Min | 4.05 | Very low risk of lymphoproliferation |
| BV30 | 24.72 | | | |
| BV28 | 24.91 | Median Ct | 25.79 | |
| BV7 | 24.98 | divpenia ratio [Ct actin]/[Median Ct] | 0.909267158 | Low risk of divpenia |

| Genes | Ct cycles | Indices | Value | Interpretation |
|---|---|---|---|---|
| BV27 | 24.98 | Mean Ct BV | 25.73 | |
| BV9 | 25.32 | detection divpenia ratio [Ct actin]/[Mean Ct] | 0.911387485 | Low risk of divpenia |
| BV24 | 25.45 | | | |

The following table illustrates the detection of a lymphoproliferation and the appearance of an associated lack of diversity ("divpenia"): each analysis is carried out at a constant amount of gDNA (50 ng of gDNA per PCR reaction), on samples composed of a distribution of PBMCs diluted, respectively, in 10%, 50%, 80% and 100% of T SUP cell lines (having a TRBV9 rearrangement).

| Gene | Ct | Index | Value | Interpretation |
|---|---|---|---|---|
| PBMC 90% + SUP 10% | | | | |
| CQi | 22.96 | | | |
| BV9 | 23.75 | | | |
| BV5 | 26.2 | CtMax | 30.47 | |
| BV20 | 26.2 | CtMin | 23.75 | |
| BV6 | 26.5 | Delta Ct Max – Min | 6.72 | Moderate risk of lymphoproliferation |
| BV27 | 26.67 | | | |
| BV4 | 26.69 | Median Ct | 27.85 | |
| BV3 | 26.84 | Divpenia ratio [Ct actin]/[Median Ct] | 0.824416517 | Low risk of divpenia |
| BV19 | 27.07 | Mean Ct | 27.66695652 | |
| BV30 | 27.11 | Divpenia ratio [Ct actin]/[Mean Ct] | 0.829870824 | Low risk of divpenia |
| BV24 | 27.53 | | | |
| BV2 | 27.71 | | | |
| BV12 | 27.85 | | | |
| BV10 | 27.98 | | | |
| BV18 | 28.04 | | | |
| BV11 | 28.09 | | | |
| BV29 | 28.11 | | | |
| BV7 | 28.12 | | | |
| BV14 | 28.44 | | | |
| BV25 | 28.6 | | | |
| BV15 | 29 | | | |
| BV28 | 29.38 | | | |
| BV13 | 29.99 | | | |
| BV16 | 30.47 | | | |
| PBMC 50% + SUP 50% (clone of TRBV9) | | | | |
| CQi | 23.03 | | | |
| BV9 | 22.12 | | | |
| BV5 | 24.54 | CtMax | 30.77 | |
| BV20 | 24.55 | CtMin | 22.12 | |
| BV19 | 25.73 | Delta Ct Max – Min | 8.65 | High risk of lymphoproliferation |
| BV24 | 25.84 | | | |
| BV7 | 26.05 | Median Ct | 27.22 | |
| BV4 | 26.36 | Divpenia ratio [Ct actin]/[Median Ct] | 0.846069067 | |
| BV10 | 26.69 | Mean Ct | 27.23130435 | |
| BV30 | 26.75 | Divpenia ratio [Ct actin]/[Mean Ct] | 0.845717844 | Low risk of divpenia |
| BV11 | 26.98 | | | |
| BV3 | 27.05 | | | |
| BV27 | 27.22 | | | |
| BV18 | 27.39 | | | |
| BV12 | 27.43 | | | |
| BV25 | 27.66 | | | |
| BV6 | 28.13 | | | |
| BV14 | 28.16 | | | |
| BV29 | 28.56 | | | |
| BV28 | 28.87 | | | |
| BV13 | 29.24 | | | |
| BV2 | 29.72 | | | |
| BV16 | 30.51 | | | |
| BV15 | 30.77 | | | |
| PBMC 20% + SUP 80% (clone of TRBV9) | | | | |
| CQi | 23.01 | | | |
| BV9 | 21.23 | | | |
| BV5 | 25.25 | CtMax | 31.1 | |
| BV20 | 25.9 | CtMin | 21.23 | |
| BV24 | 26.45 | Delta Ct Max – Min | 9.87 | Very high risk of lymphoproliferation |
| BV4 | 27.31 | | | |
| BV6 | 27.33 | Median Ct | 28.03 | |
| BV3 | 27.43 | Divpenia ratio [Ct actin]/[Median Ct] | 0.820906172 | |
| BV27 | 27.45 | Mean Ct | 27.89782609 | |
| BV11 | 27.75 | Divpenia ratio [Ct actin]/[Mean Ct] | 0.825 | Low risk of divpenia |
| BV12 | 27.79 | | | |
| BV30 | 27.89 | | | |
| BV29 | 28.03 | | | |
| BV19 | 28.09 | | | |
| BV7 | 28.19 | | | |
| BV18 | 28.38 | | | |
| BV2 | 28.43 | | | |
| BV10 | 28.82 | | | |
| BV13 | 29.16 | | | |
| BV14 | 29.21 | | | |
| BV15 | 29.36 | | | |
| BV25 | 30.27 | | | |
| BV28 | 30.83 | | | |
| BV16 | 31.1 | | | |
| PBMC 0% + SUP 100% (clone of TRBV9) | | | | |
| CQi | 23.62 | | | |
| BV9 | 21.03 | | | |
| BV5 | 25.35 | CtMax | 34.89 | |
| BV24 | 27.06 | CtMin | 21.03 | |
| BV14 | 30.24 | Delta Ct Max – Min | 13.86 | Very high risk of lymphoproliferation |
| BV18 | 30.53 | | | |
| BV20 | 30.91 | Median Ct | 32.38 | |
| BV10 | 31.39 | Divpenia ratio [Ct actin]/[Median Ct] | 0.729462631 | |
| BV11 | 31.92 | Mean Ct | 31.53913043 | |
| BV4 | 32.1 | Divpenia ratio [Ct actin]/[Mean Ct] | 0.749 | High risk of divpenia |
| BV12 | 32.14 | | | |
| BV19 | 32.28 | | | |
| BV6 | 32.38 | | | |
| BV27 | 32.46 | | | |
| BV15 | 32.58 | | | |
| BV25 | 32.59 | | | |
| BV2 | 32.79 | | | |
| BV16 | 32.9 | | | |
| BV7 | 33.05 | | | |
| BV30 | 33.6 | | | |
| BV13 | 34.13 | | | |
| BV3 | 34.2 | | | |
| BV28 | 34.88 | | | |
| BV29 | 34.89 | | | |

EXAMPLE 24

Example of Results in Vaccinology Combination of the Measurement of the Number of Regulatory T Lymphocytes and Immune Repertoire This example goes deeper into what has already been presented in example 18 above.

By virtue of the method of the invention, the inventors were able to observe that, when an individual has an initial combinatorial diversity >50%, the observation of a decrease in combinatorial diversity combined with a decrease in detection of regulatory T cells or of CD25++ cells is an indicator of the vaccination efficacy.

Figure 23:
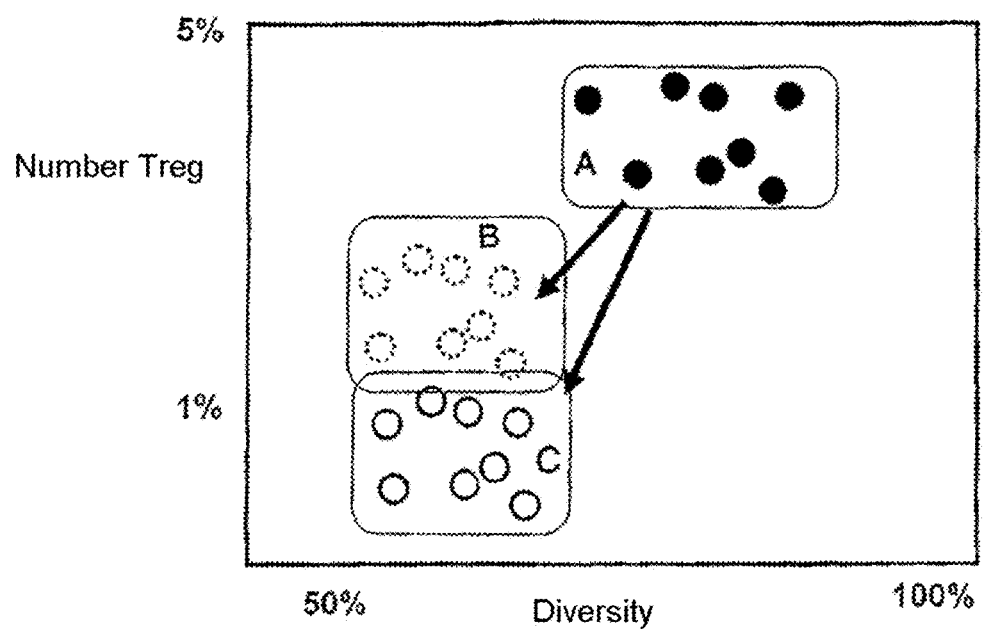

This is illustrated in FIG. 23, which shows a graph of the measurement of the number of regulatory T lymphocytes as a function of the immunity diversity of the T lymphocytes. Each point corresponds to an individual (the individuals in this example being mice). The graph shows three groups of individuals: A/before vaccination or injection of PBS (=negative control), B/after vaccination with vaccination protocol n°1, C/after vaccination with vaccination protocol n°2.

As already observed in example 18, the vaccination of mice having a normal immune diversity (>70% combinatorial diversity) induces a decrease in the diversity. This decrease in the diversity is, in addition, in combination with a decrease in the number of regulatory T lymphocytes and CD4+25++ cells. In the situation presented, it is possible to distinguish differences between the two vaccination protocols in terms of their impact on the immune system. From a functional point of view, the mice suffering from cancer and having received protocol n°2 (group C) have a greater survival than the mice having received protocol n°1. These results appear to indicate that it is possible to predict the vaccine efficacy by combining the measurement of the immune diversity with the measurement of the number of regulatory T lymphocytes. This therefore makes it possible to evaluate and, optionally, to compare the efficacy of various vaccine protocols, in order to test the effect of all the factors involved, such as, for example, the nature of the adjuvant, the type of vaccine (peptides, recombinant, etc.), the dose, the method of administration and/or the site of injection, the frequency of administration, etc.

The overall observation of the results shows that, in general, vaccinating mice makes it possible to make the % of the populations and the diversity of the mice within the same group more homogeneous. On the graphs, this corresponds to a larger "surface area" for the PBS control groups than for the groups of vaccinated mice. This is because, for the nontreated control mice, large differences are observed both in terms of the phenotypes and in terms of the combinatorial diversity. After vaccination, the distribution of the phenotype of the lymphocyte populations studied and also the combinatorial diversity of the repertoire are more homogeneous within the same group of mice.

A vaccine protocol which induces a two-fold decrease in the number of regulatory T lymphocytes in a lymph node, in the spleen or at the periphery, combined with a decrease in the immune diversity of more than 10%, and preferably more than 15%, relative to the group before vaccination or to a control group, will, a priori, be an effective protocol. N.B.: according to the observations made by the inventors, the greater the decrease in these two biomarkers, the greater the effect of the vaccination protocol on the immune system. The measurement of the lymphocyte diversity, combined, where appropriate, with the measurement of the number of regulatory T lymphocytes, therefore makes it possible to select a more effective vaccination protocol from various protocols.

Along the same lines, any strategy aimed at transiently decreasing the amount of regulatory T cells in the organism would make it possible to increase vaccine and antitumor efficacy.

REFERENCES

Aude-Garcia, C., Gallagher, M., Marche, P. N., and Jouvin-Marche E. (2001). Preferential ADV-AJ association during recombination in the mouse T-cell receptor alpha/delta locus. Immunogenetics 52, 224-230.

Baum, P. D., and McCune, J. M. (2006). Direct measurement of T-cell receptor repertoire with AmpliCot, Nat Methods 3, 895-901.

Baum, T. P. Hierle, V., Pasqual, N., Bellahcene, F., Chaume, D., Lefranc, M. P., Jouvin-Marche, E., Marche, P. N., and Demongeot, J. (2006). IMGT/GeneInfo: T cell receptor gamma TRG and delta TRD genes in database give access to all TR potential V(D)J recombinations. BMC Bioinformatics 7, 224.

Baum, T. P., Pasqual, N., Thuderoz, F., Hierle, V., Chaume, D., Lefranc, M. P., Jouvin-Marche, E., Marche, P. N., and Demongeot, J. (2004). IMGT/GeneInfo: enhancing V(D)J recombination database accessibility. Nucleic Acids Res 32, D51-54.

Berek. C., Griffiths, G. M., and Milstein, C. (1985). Molecular events during maturation of the immune response to oxazolone. Nature 316, 412-418.

Bogue, M., Gilfillan, S., Benoist, C., and Mathis, D. (1992). Regulation of N-region diversity in antigen receptors through thymocyte differentiation and thymus ontogeny. Proc Natl Acad Sci USA 89, 11011-11015.

Bonarius, H. P., Baas, F., Remmerswaal, E. B., van Lier, R. A., ten Berge, I. J., Tak, P. P., and de Vries, N. (2006). Monitoring the T-cell receptor repertoire at single-clone resolution. PLoS ONE 1, e55.

Cabaniols, J. P., Fazilleau, N., Casrouge, A., Kourilsky, P., and Kanellopoulos, J. M. (2001). Most alpha/beta T cell receptor diversity is due to terminal deoxynucleotidyl transferase. J Exp Med 194, 1385-1390.

Chaudhuri, J., Tian, M., Khoung, C., Chua, K., Pinaud, E., and Alt, F. W. (2003). Transcription-targeted DNA deamination by the AID antibody diversification enzyme. Nature 422, 726-730.

Cochet, M., Pannetier, C., Regnault, A., Darche, S., Leclerc, C., and Kourilsky, P. (1992). Molecular detection and in vivo analysis of the specific T cell response to a protein antigen. Eur J Immunol 22, 2639-2647.

Davis, M. M., and Bjorkman, P. J. (1988). T-cell antigen receptor genes and T-cell recognition. Nature 334, 395-402.

Douek, D. C., McFarland, R. D., Keiser, P. H., Gage, E. A., Massey, J. M., Haynes, B. F., Polis, M. A., Haase, A. T., Feinberg, M. B., Sullivan, J. L. et al. (1998). Changes in thymic function with age and during the treatment of HIV infection. Nature 396, 690-695.

Fugmann, S. D., Lee, A. I., Shockett, P. E., Villey, I. J., and Schatz, D. G. (2000). The RAG proteins and V(D)J recombination: complexes, ends, and transposition. Annu Rev Immunol 18, 495-527.

Fuschiotti, P., Pasqual, N., Hierle, V., Borel, E., London, J., Marche, P. N., and Jouvin-Marche, E. (2007). Analysis of the TCR alpha-chain rearrangement profile in human T lymphocytes. Mol Immunol 44, 3380-3388.

Hamblin, T. J., Davis, Z., Gardiner, A., Oscier, D. G., and Stevenson, F. K. (1999). Unmutated Ig V(H) genes are associated with a more aggressive form of chronic lymphocytic leukemia. Blood 94, 1848-1854.
Huang, C., and Kanagawa, O. (2001). Ordered and coordinated rearrangement of the TCR alpha locus: role of secondary rearrangement in thymic selection. J. Immunol 166, 2597-2601.
Jouvin-Marche, E., Aude-Garcia, C., Candeias, S., Borel, E., Hachemi-Rachedi, S., Gahery-Segard, H., Cazenave, P. A., and Marche, P. N. (1998). Differential chronology of TCRADV2 gene use by alpha and delta chains of the mouse TCR. Eur J Immunol 28, 818-827.
Kotani, A., Okazaki, I. M., Muramatsu, M., Kinoshita, K., Begum, N. A., Nakajima, T., Saito, H., and Honjo, T. (2005). A target selection of somatic hypermutations is regulated similarly between T and B cells upon activation-induced cytidine deaminase expression. Proc Natl Acad Sci USA 102, 4506-4511.
Lang. R., Pfeffer, K., Wagner, H., and Heeg, K. (1997). A rapid method for semiquantitative analysis of the human V beta-repertoire using TaqManR PCR. J Immunol Methods 203, 181-192.
Lefrancs, *The Immunoglobulin Facts Book* 2001.
Lefrancs, *The T cell receptor Facts Book* 2001.
Oprea, M., and Kepler, T. B. (1999). Genetic plasticity of V genes under somatic hypermutation: statistical analyses using a new resampling-based methodology. Genome Res 9, 1294-1304.
Pannetier, C., Even, J., and Kourilsky, P. (1995). T-cell repertoire diversity and clonal expansions in normal and clinical samples. Immunol Today 16, 176-181.
Pasqual, N., Gallagher, M., Aude-Garcia, C., Loiodice, M., Thuderoz, F., Demongeot, J., Ceredig, R., Marche, P. N., and Jouvin-Marche, E. (2002). Quantitative and qualitative changes in V-J alpha rearrangements during mouse thymocytes differentiation: implication for a limited T cell receptor alpha chain repertoire. J Exp Med 196, 1163-1173.
Pham, T., Belzer, M., Church, J. A., Kitchen, C., Wilson, C. M., Douglas, S. D., Geng, Y., Silva, M., Mitchell, R. M., and Krogstad, P. (2003). Assessment of thymic activity in human immunodeficiency virus-negative and -positive adolescents by real-time PCR quantitation of T-cell receptor rearrangement excision circles. Clin Diagn Lab Immunol 10, 323-328.
Rytkonen, M. A., Hurwitz, J. L., Thompson, S. D., and Pelkonen, J. (1996). Restricted onset of T cell receptor alpha gene rearrangement in fetal and neonatal thymocytes. Eur J Immunol 26, 1892-1896.
Van den Beemd, van Dongen et al. (2000), "Flow cytometric detection of clonality in mature T-cell malignancies by use of a Vb antibody kit", ISAC
Wang. F., Huang, C. Y., and Kanagawa, O. (1998). Rapid deletion of rearranged T cell antigen receptor (TCR) Valpha-Jalpha segment by secondary rearrangement in the thymus: role of continuous rearrangement of TCR alpha chain gene and positive selection in the T cell repertoire formation. Proc Natl Acad Sci USA 95, 11834-11839.

The invention claimed is:

1. A method of in vitro analysis of the diversity of the repertoire of T and/or B lymphocytes of an individual, from genomic DNA originating from a biological sample from said individual, comprising the following steps:
   (A) amplifying fragments of said genomic DNA by at least one multi-n-plex polymerase chain reaction (PCR) with n≥2, carried out with n different pairs of primers in a single reaction,
   wherein
   (i) each of the n different pairs of primers consists of a sense primer which specifically hybridizes upstream of and/or in a given V or D gene and an antisense primer which specifically hybridizes downstream of and/or in a given J gene;
   (ii) at least two of the n different pairs of primers comprise
      (a) a first pair of a common sense primer and a first antisense primer, and a second pair of the common sense primer and a second antisense primer, wherein the first and second antisense primers are different, or
      (b) a first pair of a first sense primer and a common antisense primer, and a second pair of a second sense primer and the common antisense primer, wherein the first and second sense primers are different;
   (iii) the primers are thermodynamically compatible; and
   (iv) the primers are chosen in such a way that the fragments amplified with the first pair of primers can be distinguished from the fragments amplified with the second pair of primers;
   (B) detecting the amplification products obtained in step A;
   (C) analyzing the diversity of the repertoire of T and/or B lymphocytes of said individual by analyzing the diversity of the amplification products detected in step (B), wherein the diversity of the amplification products detected in step (B) corresponds to the diversity of the repertoire of T and/or B lymphocytes of said individual.

2. The method as claimed in claim 1, wherein the analyzing step comprises analyzing the combinatorial diversity of the V(D)J rearrangements of at least one genetic locus selected from the group consisting of TRA, TRB, TRG, TRD, IgH, IgK and IgL loci.

3. The method as claimed in claim 1, in which at least one primer of each pair of primers is labeled.

4. The method as claimed in claim 1, in which
   step (B) comprises a step of real-time measurement of the amplification of the DNA fragments by obtaining one amplification curve per amplification reaction, and
   in step (C)
   (i) if one two or three amplification curves exhibit(s) a shift compared with the other amplification curves, such that the other amplification curves exhibit a point of inflexion at least 2 cycles after the point of inflexion of the first amplification curve, or show(s) no amplification, the result indicates the presence of clonal or oligoclonal lymphoproliferation; or (ii) if all the amplification curves exhibit a point of inflexion at the same cycle, or with a maximum shift of 2 or 3 amplification cycles, the result makes it possible to discard the indication of lymphoproliferation of a clone resulting from one of the rearrangements corresponding to the amplified fragments.

5. The method as claimed in claim 4, further comprising a step of confirmation of lymphoproliferation, by continuous measurement of fluorescence in each tube during an increase in temperature between 40° C. and 95° C., the observation of a predominant peak being indicative of the presence of a predominant amplicon and therefore of a lymphoproliferation, whereas the observation of several peaks of similar sizes indicates lymphocyte diversity.

6. The method as claimed in claim 4, further comprising a step of measuring molecular diversity of the rearrangements observed, by measuring the molecular diversity of amplicons from the amplification by:
(i) after dehybridization of the amplicons at 95° C., reducing the temperature of the amplification products to 30° C. or below;
(ii) measuring fluorescence continually during rehybridization of the amplicons;
(iii) determining the molecular diversity of the amplicons based on the rate of rehybridization.

7. The method as claimed in claim 1, in which step (B) of detection of the amplification products comprises a step of separation of said products according to their size.

8. The method as claimed in claim 1, in which the pairs of primers used in each multi-n-plex PCR reaction with n≥2 are configured so that at least some of the products of the amplification with one pair of primers have sizes that are different than those of the products of the amplification with the other pair(s) of primers.

9. The method as claimed in claim 1, in which the at least two of the n different pairs of primers comprise (a) the first pair of the common sense primer and the first antisense primer, and the second pair of the common sense primer and the second antisense primer, wherein
the common sense primer specifically hybridizes upstream of and/or in the given V gene.

10. The method as claimed in claim 9, in which the fragments of said genomic DNA are amplified by at least two multi-2-plex PCRs, each of which is carried out with two different pairs of primers, wherein
the two different pairs of primers consists of the first pair of the common sense primer and the first antisense primer, and the second pair of the common sense primer and the second antisense primer, and
the common sense primer specifically hybridizes upstream of and/or in the given V gene.

11. The method as claimed in claim 1, in which the at least two of the n different pairs of primers comprise (b) the first pair of the first sense primer and the common antisense primer, and the second pair of a second sense primer and the common antisense primer, wherein
the sense primers specifically hybridize upstream of and/or in the given V gene.

12. The method as claimed in claim 1, wherein the analyzing step comprises analyzing rearrangements of TRB locus, and
(i) the at least two pairs of primers comprise (a) the first pair of the common sense primer and the first antisense primer, and the second pair of the common sense primer and a second antisense primer, in which the common sense primer specifically hybridizes upstream of and/or in the given V gene;
(ii) the two antisense primers specifically hybridize downstream of and/or in two genes $J_y$, and $J_z$ belonging to two distinct groups of J genes of the TRB locus; and
(iii) the distance between the region of hybridization of the antisense primer specific for the $J_y$ gene and the start of said $J_y$ gene is greater than the distance between the region of hybridization of the antisense primer specific for the $J_z$ gene and the start of the first J gene of the group of genes of said $J_z$ gene.

13. The method as claimed in claim 12, wherein the analyzing step comprises analyzing rearrangements of human TRB locus, and the at least two of the n different pairs of primers comprise (a) the first pair of the common sense primer and the first antisense primer, and the second pair of the common sense primer and a second antisense primer, in which
the first antisense primer is primer hTRBJ1.6 having a sequence of SEQ ID NO: 1, the second antisense primer is primer hTRBJ2.7 having a sequence of SEQ ID NO: 2, and the common sense primer specifically hybridizes upstream of and/or in the given V gene.

14. The method as claimed in claim 12, wherein the analyzing step comprises analyzing V(D)J rearrangements of human TRB locus, and the at least two of the n different pairs of primers comprise (a) the first pair of the common sense primer and the first antisense primer, and the second pair of the common sense primer and a second antisense primer, in which
the first antisense primer is primer hTRBJ1.6 having a sequence of SEQ ID NO: 1, the second antisense primer is primer hTRBJ2.7 having a sequence of SEQ ID NO: 2, and the common sense primer is hTRBV primer selected from the group consisting of primers having sequence of SEQ ID NO: 3-24.

15. The method as claimed in claim 1, wherein the analyzing step comprises detecting incomplete D-J rearrangements in a genetic locus chosen from TRB and IgH loci.

16. The method as claimed in claim 15, wherein the analyzing step comprises analyzing incomplete DJ rearrangements of human TRB locus, and:
(i) the at least two pairs of primers comprise (a) the first pair of the common sense primer and the first antisense primer, and the second pair of the common sense primer and a second antisense primer, in which the common sense primer which specifically hybridizes upstream of and/or in the given D gene;
(ii) the two antisense primers specifically hybridize downstream of and/or in two genes $J_y$ and $J_z$ belonging to two distinct groups of J genes of the TRB locus; and
(iii) the distance between the region of the hybridization of the antisense primer specific for the $J_y$ gene and the start of said $J_y$ gene is greater than the distance between the region of hybridization of the antisense primer specific for the $J_z$ gene and the start of the first J gene of the group of genes of said $J_z$ gene.

17. The method as claimed in claim 16, wherein the analyzing step comprises analyzing incomplete rearrangements of the TRB locus, and the at least two of the n different pairs of primers comprise (a) the first pair of the common sense primer and the first antisense primer, and the second pair of the common sense primer and a second antisense primer, in which the common sense primer specifically hybridizes upstream of and/or in the given D gene, the first antisense primer is primer hTRBJ1.6 having a sequence of SEQ ID NO: 1, and the second antisense primer is primer hTRBJ2.7 having a sequence of SEQ ID NO: 2.

18. The method as claimed in claim 16, wherein the analyzing step comprises analyzing all incomplete rearrangements of the human TRB locus, the fragments of said genomic DNA are amplified by
 (i) a multi-2-plex PCR, which is carried out with two different pairs of primers, consisting of (a) the first pair of the common sense primer and the first antisense primer, and the second pair of the common sense primer and the second antisense primer, in which
  the first antisense primer is primer hTRBJ1.6 having a sequence of SEQ ID NO: 1, the second antisense primer is primer hTRBJ2.7 having a sequence of SEQ ID NO: 2, and the common sense primer is hTRBD1 primer, and
 (ii) a simple multiplex PCR using a pair of primers consisting of the primer hTRBJ2.7 and hTRBD2 primer, and
 each of the hTRBD1 and hTRBD2 primers is selected from the group consisting of primers having sequences of SEQ ID NO: 26-29.

19. A method of analyzing a combinatorial diversity of the rearrangements of TRB locus in an individual, comprising the method as claimed in claim 12, and further analyzing incomplete rearrangements of the TRB locus by
 (D) amplifying the fragments of said genomic DNA by at least one second multi-n-plex PCR with n≥2 in a single reaction, wherein
  the at least two pairs of primers of the second multi-n-plex PCR comprise (a) a third pair of a second common sense primer and a third antisense primer, and a fourth pair of the second common sense primer and a fourth antisense primer, in which the second common sense primer which specifically hybridizes upstream of and/or in the given D gene;
  the third and fourth antisense primers specifically hybridize downstream of and/or in two genes $J_y$ and $J_z$ belonging to two distinct groups of J genes of the TRB locus; and
  the distance between the region of the hybridization of the antisense primer specific for the $J_y$ gene and the start of said $J_y$ gene is greater than the distance between the region of hybridization of the antisense primer specific for the $J_z$ gene and the start of the first J gene of the group of genes of said $J_z$ gene;
 (E) detecting the amplification products obtained in step (D);
 (F) analyzing the diversity of the repertoire of T and/or B lymphocytes of said individual by analyzing the diversity of the amplification products detected in step (E), wherein the diversity of the amplification products detected in step (E) corresponds to the diversity of the repertoire of T and/or B lymphocytes of said individual.

20. The method as claimed in claim 1, wherein the analyzing step comprises analyzing rearrangements of 95% of the J genes of human TRA locus with a given V gene of the same locus, in which, in step (A), 6 multi-2-plex PCRs or 3 multi-4-plex PCRs are carried out with primers comprising one or two pair(s) of antisense primers selected from the group consisting of pairs
 (i) SEQ ID NO: 30 and SEQ ID NO: 31;
 (ii) SEQ ID NO: 32 and SEQ ID NO: 33;
 (iii) SEQ ID NO: 34 and SEQ ID NO: 35;
 (iv) SEQ ID NO: 36 and SEQ ID NO: 37;
 (v) SEQ ID NO: 38 and SEQ ID NO: 39; and
 (vi) SEQ ID NO: 40 and SEQ ID NO: 41.

21. A method as claimed in claim 20, wherein the analyzing step further comprises analyzing diversity of the VJ rearrangements of the TRA locus, wherein the 6 multi-2-plex PCRs or 3 multi-4-plex PCRs are carried out with at least three primers which hybridize upstream of and/or in three distinct V genes, each located in a distinct region of the locus.

22. The method as claimed in claim 20, in which at least one primer which hybridizes upstream of and/or in a V gene of the TRA locus is selected from the group consisting of primers having sequences of SEQ ID NO: 42-61.

23. The method as claimed in claim 1, wherein the analyzing step comprises analyzing the rearrangements of all the J genes of human TRG locus with at least 2 given genes $V_x$ and $V_y$ of the same locus, and
 the fragments of said genomic DNA are amplified by a multi-2-plex PCR, carried out with two different pairs of primers consisting of (b) the first pair of the first sense primer and the common antisense primer, and the second pair of the second sense primer and the common antisense primer, in which
  the first and second sense primers hybridize upstream of and/or in said $V_x$ and $V_y$ genes, and the common antisense primer is a primer hTRGJdo2 having a sequence of SEQ ID NO: 62.

24. The method as claimed in claim 23, in which at least one primer which hybridizes upstream of and/or in a V gene of the human TRG locus is selected from the group consisting of primers having sequences of SEQ ID No: 63-66.

25. The method as claimed in claim 1, wherein the analyzing step comprises analyzing the rearrangements of all the J genes of the human TRD locus with a given V gene of the same locus, and
 the fragments of said genomic DNA are amplified by a multi-2-plex PCR, carried out with two different pairs of primers consisting of (a) the first pair of the common sense primer and the first antisense primer, and the second pair of the common sense primer and the second antisense primer, in which
  the common sense primer hybridizes upstream of and/or in said V gene, and the antisense primers are primer hTRDJ1do5 having a sequence of SEQ ID NO: 67 and primer hTRDJ3do2 having a sequence of SEQ ID NO: 68.

26. The method as claimed in claim 25, wherein the analyzing step further comprises analyzing the VJ rearrangements of the TRD locus, and the fragments of said genomic DNA are amplified by carrying out 24 multi-n-plex PCRs with using combinations of at least 3 primers, each combination of primers comprising the hTRDJ1do5 and hTRDJ3do2 antisense primers and at least one primer selected from the group consising of primers having sequences of SEQ ID NO: 69-84.

27. The method as claimed in claim 1, wherein the analyzing step comprises analyzing the rearrangements of all the J genes of human IgH locus with at least 2 given genes $V_x$ and $V_y$ of the same locus, uand
 the fragments of said genomic DNA are amplified by a multi-2-plex PCR, carried out with two different pairs of primers consisting of (b) the first pair of the first sense primer and the common antisense primer, and the second pair of the second sense primer and the common antisense primer, in which the first and second sense primers hybridize upstream of and/or in said $V_x$ and $V_y$ genes, and the common antisense primer hybridizes downstream of and/or in IgHJ6 gene.

28. The method as claimed in claim 27, in which the antisense primer is hIgHJ6do2 primer having a sequence of SEQ ID NO: 85.

29. The method as claimed in claim 27, in which at least one primer which hybridizes upstream of and/or in a V gene of the human IgH locus is selected from the group consisting of primers having sequences of SEQ ID NO: 86-91.

30. The method as claimed in claim 15, wherein the analyzing step comprises analyzing incomplete rearrangements of the human IgH locus, and the at least two pairs of primers comprise (b) the first pair of the first sense primer and the common antisense primer, and the second pair of the second sense primer and the common antisense primer, the common antisense primer specifically hybridizes downstream of and/or in a given J gene, and the sense primers hybridize upstream of and/or in a given D gene of the human igH locus.

31. The method as claimed in claim 30, in which the common antisense primer is hIgHJ6do2 primer having a sequence of SEQ ID NO: 85.

32. The method as claimed in claim 30, in which at least one sense primer is selected from the group consisting of primers having sequences of SEQ ID NO: 92-98.

33. The method as claimed in claim 1, wherein the analyzing step comprises analyzing combinatorial diversity of the V(D)J rearrangements of at least two genetic loci selected from the group consisting of the TRA, TRB, TRG, TRD, IgH, IgK and IgL loci.

34. The method as claimed in claim 33, wherein the analyzing step comprises analyzing the combinatorial diversity of the V(D)J rearrangements of the TRB locus and the combinatorial diversity of the VJ rearrangements of the TRG locus or of the TRD locus.

35. The method as claimed in claim 33, wherein the analyzing step further comprises analyzing the combinatorial diversity of the V(D)J rearrangements of the IgH locus.

36. The method as claimed in claim 1, in which the multin-plex PCR reactions are carried out with a polymerase, wherein
(i) the polymerase is configured to amplify fragments of twenty kb or more;
(ii) the elongation rate of the polymerase is at least 1 kb/minute; and
(iii) the polymerase does not introduce more than one error per kb, on average.

37. The method as claimed in claim 7, in which step (C) comprises a step of processing data obtained by separating the amplicons according to their size, said processing being carried out by means of a computer and making it possible to assign, to each amplicon observed, a name of the corresponding V(D)J rearrangement.

38. The method as claimed in claim 37, in which the processing of the data also integrates the intensity of the signal of each of the amplicons observed, and quantify a relative frequency of the corresponding V(D)J rearrangement.

39. The method as claimed in claim 37, in which step (B) comprises acquiring data concerning the size of the amplicons and, for each one, the intensity of the signal, and step (C) comprises the following steps:
(i) identifying each amplicon, by determining the V(D)J rearrangement to which it corresponds, as a function of its size;
(ii) from the intensity of the signal of each amplicon, determining the proportion of starting genomic DNA having the corresponding V(D)J rearrangement;
(iii) analyzing the results in the form of a three-dimensional graph showing the $V_x$ genes or the families of $V_x$ genes along one axis, the $J_y$ genes along another axis, and the frequency of the $V_x J_y$ rearrangements along the third axis.

40. A method of determining, in vitro, a degree of immunodeficiency of an individual, comprising the following steps:
(A) using a biological sample from said individual, performing a lymphocyte count;
(B) using the same sample or another sample taken from the same individual at the same time, determining the degree of combinatorial diversity of the repertoire of lymphocytes of said individual, by implementing a method as claimed in claim 1;
(C) combining the data obtained in steps (A) and (B), and determining the degree of immunodeficiency based on the lymphocyte count and the degree of combinatorial diversity.

41. The method as claimed in claim 40, further comprising a step of interpreting the combination obtained in step (C), based on a graph which assigns a level of risk at least to 4 zones (i)-(iv):
(i) low count (<1000 Ly/µL) and low V-J combinatorial diversity (<40%): high infectious risk and a high risk of mortality owing to infection;
(ii) low count (<1000 Ly/µL) but normal V-J combinatorial diversity (>65%): low infectious risk;
(iii) normal count (1000-3200 Ly/µL) and low V-J combinatorial diversity (<40%): medium infectious risk;
(iv) normal count (1000-3200 Ly/µL) and normal V-J combinatorial diversity (>65%): the immune repertoire is healthy.

42. The method as claimed in claim 41, in which the graph further comprises 2 zones (v)-(vi):
(v) count above normal (>3200 Ly/µL) and low V-J combinatorial diversity (<40%): high lymphoproliferative risk;
(vi) count above normal (>3200 Ly/µL) and normal V-J combinatorial diversity (>65%): medium lymphoproliferative risk.

43. The method as claimed in claim 40, in which step (B) comprises the determination of degree of combinatorial diversity of the repertoire of T lymphocytes and B lymphocytes of said individual.

44. The method as claimed in claim 43, in which, in step (C), the data are examined by means of a three-dimensional graph showing the degree of immunoglobulin diversity on one axis, the degree of TCR diversity on another axis, and the lymphocyte count on a third axis.

45. A method of monitoring the change in the diversity of the repertoire of T and/or B lymphocytes of an individual, comprising
(A) measuring diversity of the repertoire of lymphocytes of said individual, by the method as claimed in claim 38, using two samples from said individual, taken at two different dates; and
(B) comparing the two samples by determining:
(i) how many rearrangements are observed in the two samples;
(ii) how many rearrangements are observed in the more recent sample but not in the older sample;
(iii) how many rearrangements are observed in the older sample but not in the more recent sample; and (iv) how many rearrangements are not observed in either of the samples.

46. A method of evaluating the efficacy of a vaccination protocol, comprising the steps of:
(A) measuring the amount and the diversity of lymphocytes before and after said vaccination protocol, using a method as claimed in claim 1;
(B) comparing the measurements carried out in step (A); and
(C) interpreting the results, wherein a decrease in lymphocyte diversity of at least 10% after vaccination, indicating that the vaccination protocol was effective.

47. The method as claimed in claim 46, in which the amount of regulatory T lymphocytes before and after vaccination is also measured in step (A), and in which, in step (C), a decrease by a factor of ≥2 in the number of regulatory T lymphocytes following the vaccination indicates that the protocol was effective.

48. The method of claim 1, wherein the analyzing step comprises analyzing the diversity of the rearrangements of the IgH locus of an individual, wherein, in step A,
(i) a first multi-n-plex PCR with n≥2 is carried out with n different pairs of primers, at least two of which comprise (b) the first pair of the first sense primer and the common antisense primer, and the second pair of the second sense primer and the common antisense primer, wherein the first and second sense primers are different, the two sense primers hybridize upstream of and/or in two given $V_x$ and $V_y$ genes of the human IgH locus, and the common antisense primer hybridizes downstream of and/or in IgHJ6 gene; and
(ii) a second multi-n-plex PCR with n≥2 is carried out with n different pairs of primers, at least two of which comprise (b) the first pair of the first sense primer and the common antisense primer, and the second pair of the second sense primer and the common antisense primer, wherein the first and second sense primers are different, the common antisense primer which specifically hybridizes downstream of and/or in a given J gene, and the two sense primers specifically hybridize upstream of and/or in two different D genes.

49. A method of monitoring the change in the diversity of the repertoire of T and/or B lymphocytes of an individual, comprising
(A) measuring the diversity of the repertoire of lymphocytes of said individual, by the method as claimed in claim 37, using two samples from said individual, taken at two different dates;
(B) comparing the two samples by determining the signals that are differentially observed in the two samples.

50. The method of claim 49, wherein the samples are compared by determining the signals that are observed with a different intensity in the second sample compared to the first sample.

51. The method as claimed in claim 1, wherein each of the different pairs of primers allow amplification of at least two DNA fragments of at least two different chromosomal rearrangements.

* * * * *